(12) United States Patent
North et al.

(10) Patent No.: US 7,386,348 B2
(45) Date of Patent: Jun. 10, 2008

(54) PATIENT INTERACTIVE NEUROSTIMULATION SYSTEM AND METHOD

(75) Inventors: Richard Boydston North, Baltimore, MD (US); Jeffrey Mark Sieracki, Silver Spring, MD (US); Kim Randal Fowler, Baltimore, MD (US); Lon Hodges Holland, Olney, MD (US)

(73) Assignee: Medtronic, Inc., Minneapolis, MN (US)

( * ) Notice: Subject to any disclaimer, the term of this patent is extended or adjusted under 35 U.S.C. 154(b) by 735 days.

(21) Appl. No.: 10/669,392

(22) Filed: Sep. 24, 2003

(65) Prior Publication Data

US 2004/0059395 A1 Mar. 25, 2004

Related U.S. Application Data

(63) Continuation of application No. 09/732,759, filed on Dec. 11, 2000, now Pat. No. 6,654,642, which is a continuation-in-part of application No. 09/408,129, filed on Sep. 29, 1999, now Pat. No. 6,308,102.

(51) Int. Cl.
*A61N 1/36* (2006.01)

(52) U.S. Cl. ...................................... 607/46

(58) Field of Classification Search ................. 607/46, 607/48, 55–57
See application file for complete search history.

(56) References Cited

U.S. PATENT DOCUMENTS

| 4,520,825 A | 6/1985 | Thompson et al. |
|---|---|---|
| 4,735,204 A | 4/1988 | Sussman et al. |
| 4,784,142 A | 11/1988 | Liss et al. |
| 4,803,988 A | 2/1989 | Thomson |
| 4,813,418 A | 3/1989 | Harris |
| 4,958,632 A | 9/1990 | Duggan |
| 4,977,895 A | 12/1990 | Tannenbaum |
| 5,002,053 A | 3/1991 | Garcia-Rill et al. |
| 5,014,705 A | 5/1991 | Graupe et al. |

(Continued)

FOREIGN PATENT DOCUMENTS

| WO | WO 97/43002 | 11/1997 |
|---|---|---|
| WO | WO 98/29160 | 7/1998 |

OTHER PUBLICATIONS

Robin et al., "A New Implantable Microstimulator Dedicated to Selective Stimulation of the Bladder," Proceedings—19th International Conference—IEEE/EMBS Oct. 30-Nov. 2, 1997, Chicago, IL, pp. 1792-1795.

(Continued)

*Primary Examiner*—George R. Evanisko
(74) *Attorney, Agent, or Firm*—Shumaker & Sieffert, PA

(57) ABSTRACT

A fully automated computer controlled system is provided for adjustment of neurostimulation implants used in pain therapy and in treating neurological dysfunction which includes a patient interactive computer, and a universal transmitter interface integrally embedded in the patient interactive computer or built into the antenna which is capable of stimulating any type of implanted neurostimulation devices by imitating programming codes. The patient interacts with the system through the patient interactive computer. The universal transmitter interface includes a direct digital synthesizer, a transistor circuitry driving the antenna in ON-OFF fashion and a gating unit for driving the transistor circuitry under control of the processing means in the patient-interactive computer. Alternatively, the universal transmitting interface includes a balanced modulator for modulation of the carrier signal generated at the direct digital synthesizer.

39 Claims, 29 Drawing Sheets

U.S. PATENT DOCUMENTS

| | | | |
|---|---|---|---|
| 5,033,469 | A | 7/1991 | Brodard |
| 5,052,391 | A | 10/1991 | Silberstone et al. |
| 5,081,989 | A | 1/1992 | Graupe et al. |
| 5,092,329 | A | 3/1992 | Graupe et al. |
| 5,117,826 | A | 6/1992 | Bartelt et al. |
| 5,143,089 | A | 9/1992 | Alt |
| 5,159,926 | A | 11/1992 | Ljungstroem |
| 5,215,086 | A | 6/1993 | Terry, Jr. et al. |
| 5,314,458 | A | 5/1994 | Najafi et al. |
| 5,330,515 | A | 7/1994 | Rutecki et al. |
| 5,335,657 | A | 8/1994 | Terry, Jr. et al. |
| 5,350,414 | A | 9/1994 | Kolen |
| 5,354,320 | A | 10/1994 | Schaldach et al. |
| 5,370,672 | A * | 12/1994 | Fowler et al. ............... 607/58 |
| 5,387,231 | A | 2/1995 | Sporer |
| 5,417,719 | A | 5/1995 | Hull et al. |
| 5,423,877 | A | 6/1995 | Mackey |
| 5,443,486 | A | 8/1995 | Hrdlicka et al. |
| 5,458,625 | A | 10/1995 | Kendall |
| 5,458,626 | A | 10/1995 | Krause |
| 5,466,246 | A | 11/1995 | Silvian |
| 5,540,730 | A | 7/1996 | Terry, Jr. et al. |
| 5,569,166 | A | 10/1996 | Stone |
| 5,643,329 | A | 7/1997 | Solomonow et al. |
| 5,643,330 | A | 7/1997 | Holsheimer et al. |
| 5,653,739 | A | 8/1997 | Maurer et al. |
| 5,702,429 | A | 12/1997 | King |
| 5,716,377 | A | 2/1998 | Rise et al. |
| 5,725,564 | A | 3/1998 | Freed et al. |
| 5,755,736 | A | 5/1998 | Gillberg et al. |
| 5,807,397 | A | 9/1998 | Barreras |
| 5,843,139 | A | 12/1998 | Goedeke et al. |
| 5,843,142 | A | 12/1998 | Sultan |
| 5,893,883 | A * | 4/1999 | Torgerson et al. ............. 607/59 |
| 5,938,690 | A * | 8/1999 | Law et al. ..................... 607/46 |
| 6,175,764 | B1 | 1/2001 | Loeb et al. |
| 6,205,359 | B1 | 3/2001 | Boveja |
| 6,249,703 | B1 | 6/2001 | Stanton et al. |
| 6,308,100 | B1 | 10/2001 | Er et al. |
| 6,308,102 | B1 * | 10/2001 | Sieracki et al. ............... 607/59 |
| 6,321,117 | B1 | 11/2001 | Koshiol et al. |
| 6,381,496 | B1 | 4/2002 | Meadows et al. |
| 6,440,090 | B1 | 8/2002 | Schallhorn |
| 6,516,227 | B1 | 2/2003 | Meadows et al. |
| 6,564,807 | B1 | 5/2003 | Schulman et al. |
| 2002/0116036 | A1 | 8/2002 | Daignault, Jr. et al. |
| 2003/0028223 | A1 | 2/2003 | Olson |

OTHER PUBLICATIONS

North et al., "Spinal cord stimulation for chronic intractable pain," Spinal Cord Stimulation II, pp. 49-63, Darmstadt, Steinkopff, 1995.

North et al., "Artificial Neural Networks: Application to Electrical Stimulation of the Nervous System," (abstract) Stereotactic and Functional Neurosurgery 65:161, 1995.

North et al., "Artificial Neural Networks: application to electrical stimulation of the human nervous system," Neurosurgical Focus 2(1:):1-5, 1997.

North et al., "Patient-Interactive, Microprocessor-Controlled Neurological Stimulation System," Neuromodulation 1(4):185-193, 1998.

Fowler, K.R., "Neurological Stimulation System", Proceedings AAMI 21st Annual Meeting, Apr. 12-16, 1986, p. 27.

North et al., "Spinal Cord Stimulation for Chronic, Intractable Pain: Experience over Two Decades Clinical Study," Neurosurgery, vol. 32, No. 3, 1993, pp. 384-395.

North et al., "Spinal cord stimulation for chronic, intractable pain: superiority of 'multi-channel' devices," Pain, vol. 44, 1991, pp.119-130.

North et al., "Spinal Cord Stimulation for Chronic Pain," Functional Neurosurgery, vol. 6, No. 1, Jan. 1995, pp. 145-155.

North, R.B., "Spinal Cord Stimulation for Chronic, Intractable Pain," Electrical and Magnetic Stimulation of the Brain and Spinal Cord, 1993, pp. 289-301.

North, R.B., "The Role of Spinal Cord Stimulation in Contemporary Pain Management," APS Journal, vol. 2, No. 2, 1993, pp. 91-99.

Alo et al., "Computer Assisted and Patient Interactive Programming of Dual Octrode Spinal Cord Stimulation in the Treatment of Chronic Pain," Neuromodulation, vol. 1, No. 1, 1998, pp. 30-45.

Fowler et al., "Patient-interactive PC interface to implanted, multichannel stimulators," Proceedings of 39th Annual Conference on Engineering in Medicine and Biology, p. 380, 1986.

North et al., "Computer-Controlled, Patient-Interactive, Multichannel, Implanted Neurological Stimulators," Applied Neurophysiology 50:39-41, 1987.

North et al., Computer-controlled, multichannel, implanted neurological stimulation system: clinical assessment, Pain (Suppl.) 5:S83, 1990.

Fowler et al., "Computer-Optimized Neurological Stimulation," Proc. Ann. Internat. Conf. IEEE Engineering Medicine and Biology Soc., vol. 13, No. 4, pp. 1692-1693, 1991.

Fowler et al., "Computer-Optimized Neurostimulation," APL Technical Digest, vol. 12, No. 2, pp. 192-197, 1991.

North et al., "Patient-interactive, computer-controlled neurological stimulation system: clinical efficacy in spinal cord stimulator adjustment." Journal of Neurosurgery 76:967-972, 1992.

North et al., "Automated 'pain drawing' analysis by computer-controlled, patient-interactive neurological stimulation system," Pain 50:51-57, 1992.

North et al., "Computer-controlled, patient-interactive neurological stimulation system," (Abstract) Acta Neurochir 117:90, 1992.

North et al., "Patient-Interactive, Microprocessor-Controlled Neurological Stimulation System," (Abstract), Stereotactic and Functional Neurosurgery 62:309-315, 1994.

North et al., "Consensus Conference on the Neurosurgical Management of Pain," Neurosurgery 34:4, 756-761, 1994.

North et al., "A Prospective, Randomized Study of Spinal Cord Stimulation versus Reoperation for Failed Back Surgery Syndrome: Initial Results," Stereotact Funct Neurosurg 1994:62:267-272.

North et al., "Prognostic Value of Psychological Testing in Patients Undergoing Spinal Cord Stimulation: A Prospective Study," Neurosurgery, vol. 39, No. 2, 1996.

North et al., "Specificity of diagnostic nerve blocks: a prospective, randomized study of sciatica due to lumbosacral spin disease," Pain, 65, pp. 77-85, 1996.

North et al., "Automated, Patient-Interactive, Spinal Cord Stimulator Adjustment: A Randomized Controlled Trial," Neurosurgery 52:572-580, 2003.

Khalessi et al., "Automated, patient-interactive spinal cord stimulator adjustment: A cost-minimization analysis," Neurosurgery, vol. 53, No. 2, pp. 501-502, 2003.

"GenesisXP™ Neurostimulation Systems," Implantable Therapies for Chronic Pain and Neurological Disorders, http://www.ans-medical.com/physicians/GenesisXPSystem/XPOverview.cfm (2 pgs.) downloaded Dec. 3, 2002.

"PainDoc® Computerized Support System," Implantable Therapies for Chronic Pain and Neurological Disorders, http://www.ans-medical.com/physicians/PainDoc/PainDoc.html (1 pg.) downloaded Dec. 3, 2002.

"MultiStim®," Implantable Therapies for Chronic Pain and Neurological Disorders, http://www.ans-medical.com/physicians/RenewRFSystem/MultiStim.html (2 pgs.) downloaded Dec. 3, 2002.

"PC-Stim®," Implantable Therapies for Chronic Pain and Neurological Disorders, http://www.ans-medical.com/physicians/RenewRFSystem/PCStim.html (2 pgs.) downloaded Dec. 3, 2002.

"Renew® Neurostimulation System Overview," Implantable Therapies for Chronic Pain and Neurological Disorders, http://www.ans-medical.com/physicians/RenewRFSystem/SystemOverview.html (3 pgs.) downloaded Dec. 3, 2002.

* cited by examiner

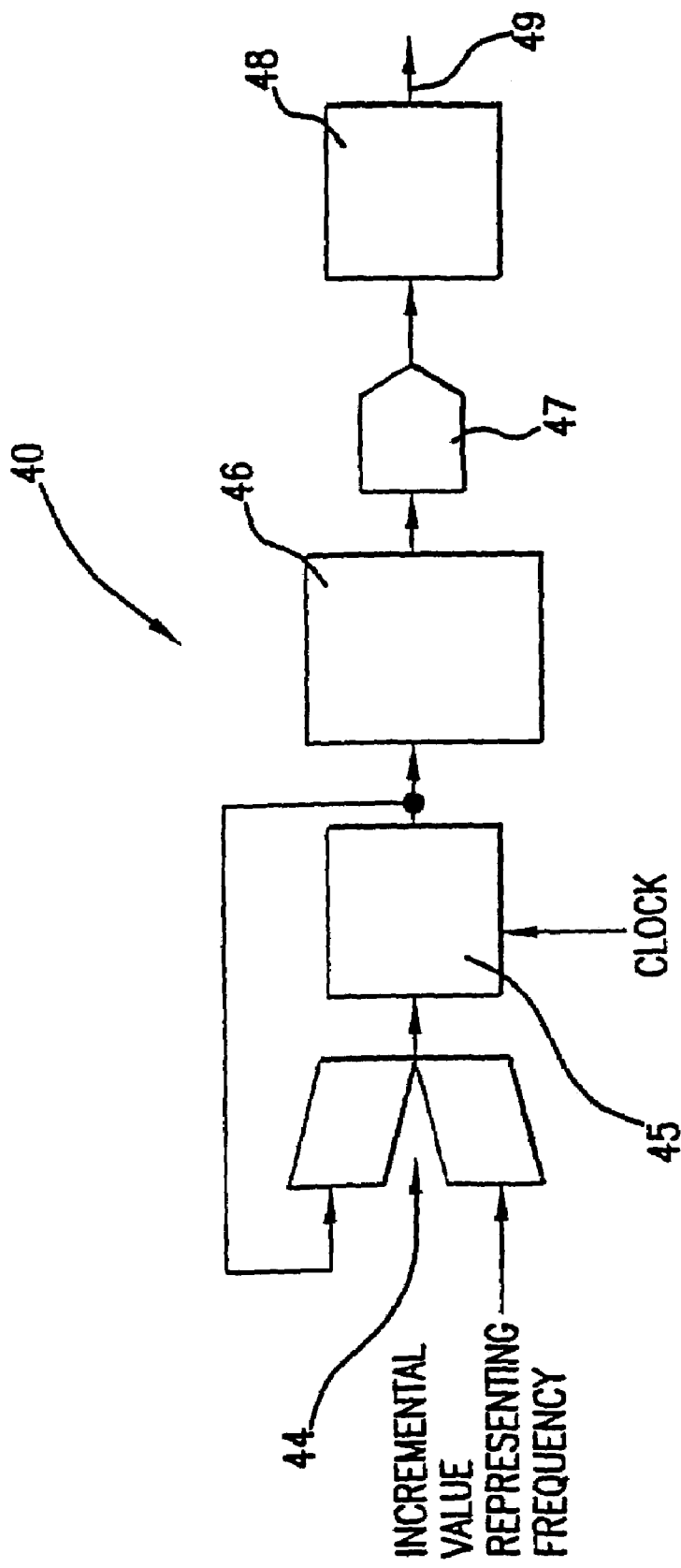

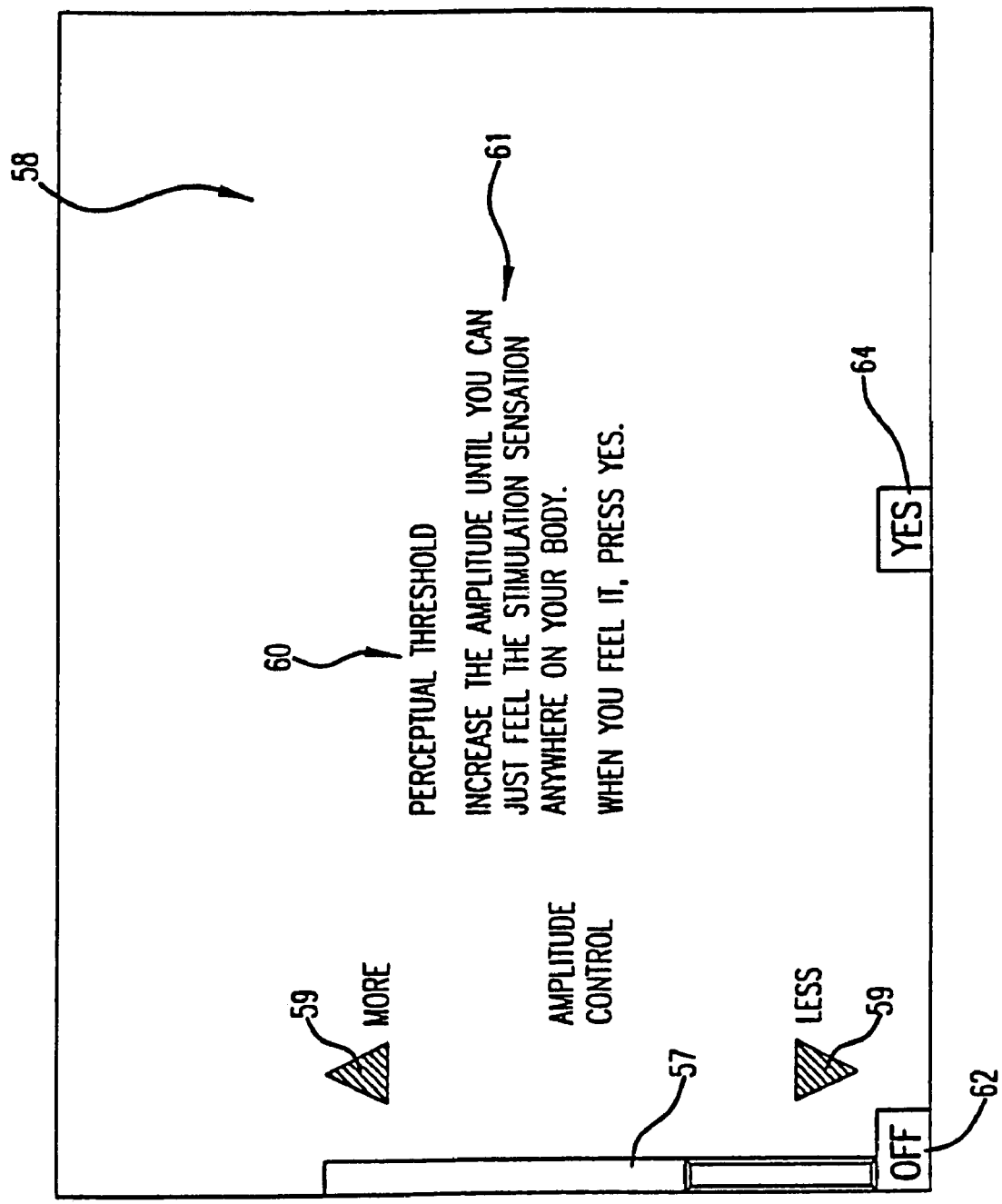

PATIENT INTERACTIVE NEUROSTIMULATION SYSTEM AND METHOD

This Patent Application is a continuation of U.S. application Ser. No. 09/732,759, filed Dec. 11, 2000, now U.S. Pat. No. 6,654,642, which is a continuation-in-part of U.S. application Ser. No. 09/408,129, filed Sep. 29, 1999. now U.S. Pat. No. 6,308,102. The entire content of each of the identified U.S. Applications is incorporated herein by reference.

FIELD OF THE INVENTION

The present invention relates to a fully automated patient interactive system for controlling neurostimulation, and more particularly, to a computer controlled system for automatic adjustment of neurostimulation implants used in pain therapy and in treating neurological dysfunction capable of automatically handling inconsistent patient data entries and unexpected conditions such as hardware failures.

Even more particularly, the present invention relates to a patient interactive system operated directly by the patient who may be safely and confidently left alone to work with the computer to obtain reliable data with the goal of maximizing pain relief while minimizing staff time demand. The novel system essentially replaces the physician, or physician's assistant, in the routine and tedious task of adjusting stimulation settings for the neurostimulation procedure.

Moreover, the present invention relates to a patient interactive system comprising a patient interactive pentop tablet computer which may include an RF (radio frequency) interface device integrally built in the pentop tablet computer or in the antenna in combination with patient interactive software and allows signal communication with neurostimulation implants using radio frequency telemetry.

Additionally, the present invention relates to a patient interactive system for controlling neurostimulation which includes a unified user interface in which the body outlines and the patient's drawings are input directly to the computer screen.

The present invention further relates to a patient interactive system having a "universal" transmitter for controlling implantable devices capable of imitating unique codes generated by proprietary neurostimulation systems thereby allowing the system of the present invention to work with a wide variety of implantable devices.

The present invention also relates to a method of controlling the neurostimulation in a neurological stimulation system for collecting data from a patient through a series of steps and further processing the collected data for optimization of the stimulus setting for the most effective pain relief and treatment.

PRIOR ART

Neurostimulators treat chronic pain by stimulating nerves, such as those of the spinal cord, with electrical pulses. Typically, neurostimulator systems comprise an external device which communicates with an implantable device through electromagnetic transmissions. The external device acts as a programmer for the implanted device by means of transmitting radio frequency codes to the implanted device to program its operation.

Neurostimulators have a number of parameters and adjustments that optimize the stimulation for each individual situation. Electrodes have multiple contacts that can have positive, negative, or off-polarity. Common configurations have 4, 8, or 16 electrode contacts within the stimulating bundle. Four electrodes can have 50 separate usable combinations of polarities. Eight electrodes can have 6050 separate usable combinations of polarities. Sixteen electrodes can have over 62,000,000 separate usable combinations of polarities. Beyond this, neurostimulators can set the frequency of stimulation between 1 Hz and 1500 Hz, set the pulse widths of stimulation between 10 and 1000 microseconds, and vary the amplitude of stimulation. These nearly inexhaustible adjustments quickly overwhelm the physical capabilities of medical staff to adjust stimulators through all settings for each patient.

To help with this concern, a computer-controlled neurological stimulation system, U.S. Pat. No. 5,370,672, was developed. The system provides efficient patient interaction, optimizes stimulation automatically, and delivers arbitrary and unique paradigms of stimulation. As shown in FIG. 1, an external transmitter 10 and implanted receiver 11 are RF coupled by an antenna 12. The external transmitter 10 is worn externally by the patient 13 to encode the stimulation parameters and the electrode selections, which are then transmitted to the implanted receiver 11 via the antenna 12. The implant decodes the transmitted information and generates the desired electrical pulses for stimulating electrodes 14 within the spinal column 15.

As shown in FIG. 2, the computer-controlled neurological stimulation system of the '672 patent includes a host computer 16, an interface enclosure 17 coupled by a cable 18 to the host computer 16, with an output line 19 coupled to an antenna 20. A graphic tablet 21 is connected by a serial line 22 to the host computer 16 which permits entry to the host computer 16 of the location of stimulation paresthesias and painful areas when a stylus 23 is manipulated over the tablet 21 by the patient. The tablet 21 has an overlay positioned on the top of the tablet 21 and contours of the body are drawn on the overlay. In operation, the physician initiates a session with the patient by calling up the appropriate programs in the host computer 16. The host computer 16 and interface enclosure 17 control one of several selective transmitters and cause the generation of various stimulation parameters such as frequency, pulse amplitude, width, and electrode combination. The patient at this time is directed via the graphics tablet 21 to interact with the host computer 16 and the interface enclosure 17 to adjust the stimulation amplitude as necessary and to sketch on the tablet 21 the areas of pain and the areas perceived by the patient to be experiencing paresthesias. While useful in reducing the workload of medical staff and automating the data collection, the system still has a number of limitations which include:

1. The patient has to look up to the monitor of the host computer 16 for instructions and then down at the graphics tablet 21 to draw responses and answers which presents a challenge in hand-eye coordination and slows data collection.
2. The overlay on the graphics tablet needs careful adjustment to accurately match its outlines of the body with the host computer's internal representation of those outlines. This calibration is also necessary to match the drawings made by the patient which represent areas of pain and stimulation paresthesia with the host computer's internal representation of the body.
3. The serial communications cable 18 between the host computer 16 and the transmitter enclosure 17 is prone to mechanical as well as electrical failure.
4. The patient is in physical contact with the transmitter interface enclosure 17 and the host computer 16, both of which are connected to electrical cords and wall outlets. These devices are powered by the building's AC power and consequently have a grounded connection that can provide a leakage path or short circuit to ground.

Another patient interactive computer based neurostimulation system is described in U.S. Pat. No. 5,938,690. This system can assist in the performance of pre-, intra-, and post-operative procedures relating to the determination and optimization of a patient's therapeutic regimen. The system is intended to record and process patient's responses to test stimulation patterns during the operation of placing the electrodes, so as to give the physician real-time information that can be used to effectively position the electrodes within the patient's body. The system also provides computer assisted post-operative presentation and assessment of stimulation settings.

Disadvantageously, the systems of prior art are not truly automated and require frequent attention by clinical staff during operation because either they do not provide automated patient interviews or their unsophisticated interview schemes are unable to automatically handle inconsistent patient data entries and unexpected conditions such as hardware failures.

Another shortcoming of the prior art neurostimulation systems is that each manufacturer of implanted devices generally has proprietary codes built on combinations of the modulation techniques to program the implantable devices. Consequently, each manufacturer has proprietary hardware, software, and systems to transmit the programming code. If a separate external system other than one provided by a manufacturer of implantable devices, communicates with an implantable device, the external system requires circuitry that emulates the proprietary system. Should the external system communicate with multiple different types of implantable devices, it must include separate circuitry to emulate each type of implant. As an example, in the system described in U.S. Pat. No. 5,938,690, a physician enters into the computer information related to electrode type and transmitter type. Thus, the system requires the transmitter to "learn" certain stored information, ensuring that the transmitter, electrodes and the system in its entirety are compatible. In each operation, the transmitter must be reset with respect to electrodes it is supposed to work with, and the transmitter may have to be replaced with another type if the adaptation is not possible due to incompatibility of the electrodes and the transmitter.

It is therefore clear that despite the advances and improvements in prior art systems for controlling neurostimulators, a novel system which is automated and "universal", i.e., compatible with a wide variety of different types of implantable devices is needed in the art of neurostimulation.

SUMMARY OF THE INVENTION

It is therefore an object of the present invention to provide a truly automated patient interactive system in which provisions are made allowing for effectively handling inconsistent patient data entries, if any, and unexpected conditions such as hardware failures, thus providing that the patient may be safely and confidently left alone to work with the computer and where reliable data can be attained without significant intervention by a human clinician during the procedure.

It is another object of the present invention to provide a patient interactive system having a "universal transmitter" adaptable substantially to all types of implanted devices, including both RF-powered and implantable pulse generators (IPG) with self-contained power sources.

It is a further object of the present invention to provide a patient interactive system for controlling neurostimulation, in which the body outline, instructions for the patient, and the patient's response are displayed and drawn on the same screen of the patient interface computer, thus avoiding hand-eye coordination problems.

It is another object of the present invention to provide a patient interactive system where the drawings are made by the patient directly on the computer screen, thereby making the data collection easier to use and speedier to collect.

It is still another object of the present invention to provide a patient interactive system having a unified structure which eliminates cables between various components, thereby greatly reducing possible-mechanical and electrical failure.

It is still a further object of the present invention to provide a patient interactive system employing a battery-powered pen top computer thereby eliminating leakage paths and short circuits to ground.

It is yet another object of the present invention to provide a patient interactive system, a method for controlling neurostimulation, and software stored in the patient interactive computer to operate the system for data collection, data processing, and optimization of stimulation settings for a particular patient and his/her problem.

In accordance with the present invention, a patient interactive system for controlling neurostimulation includes a plurality of neurological stimulator devices implanted in the body of a patient, a patient interactive computer with a display, a transmitter interface unit integrally embedded within the patient interactive computer or built-in the antenna, a stylus movable by the patient in response to the request displayed on the display of the patient interactive computer, a physician's desktop computer telemetrically communicating with the patient interactive computer, and operational software to run the system.

It is an essential and novel feature of the present invention that means are provided in the system which pre-sets consistency boundaries for data entered by the patient and which verify that the entered data fall within the consistency boundaries. If the consistency boundaries are exceeded, then the data entered are recycled, and the patient is asked to repeat a response, or the system is checked for hardware failure. This arrangement in the system of the present invention provides for full automation of operation, obtaining of reliable data, and safety for the patient, so that he/she may be confidently left alone to work with the system without intervention by a clinician.

It is also important that the system of the present invention is capable of studying the consistency behavior of the patient, and, if satisfactory, to avoid verification as to whether the boundaries are exceeded, thus providing for adaptation to each particular patient.

The neurological stimulator devices are adapted for receiving a specific one of a plurality of predetermined programming codes and responding to this code to provide electrical stimulation to nerve tissue in accordance with the programming code. It is essential that the transmitter interface unit embedded within the patient interactive computer or the antenna unit includes controlling means which are adapted to imitate any one of a plurality of predetermined programming codes and drive the transmitter interface unit to transmit the imitated specific predetermined code toward the neurological stimulator device thus providing for universality of the transmitter.

The system includes graphic means displaying screen graphics and screen worded messages for the patient (the message corresponding to the screen graphics) substantially simultaneously on the display of the patient interactive computer. The screen worded message describes to the patient an action expected from the same to operate the stylus in order to enter requested data into the patient interactive computer.

The screen graphics may present images of a human's body. Subsequently, the screen worded message requests the patient to outline, by means of the stylus, an area of the pain being experienced. The screen worded message may also request the patient to outline, by means of the stylus, a topography of paresthesias in response to electrical stimulation of the neurological stimulator devices by the specific predetermined programming code transmitted from the transmitter interface. The interior regions of graphical outlines may later be compared by the computer as part of the analysis to determine preferred stimulation settings. It is essential that the pain map and the topography of paresthesias are compared pixel by pixel rather than by any standard dermatomes in order to adapt the analysis accurately to the individual patient.

The screen graphics may also present a rating bar. The screen worded message constitutes a request for the patient to indicate on the rating bar (by means of the stylus) the degree of overlap of the area of the pain experienced and the topography of paresthesias.

Alternatively, the screen graphics may present a stimulation amplitude adjustment screen for threshold determination which includes an amplitude adjustment bar. In this mode the screen worded message requests the patient to increase the amplitude by sliding the stylus along the amplitude adjustment bar until the patient begins to feel a sensation that meets the stated criteria.

The system is capable of determination of a plurality of stimulation thresholds including the bilateral threshold, discomfort threshold, perceptual threshold, preferred level of pain relief threshold, area of interest threshold, and motor threshold. These parameters are further processed for obtaining an optimized stimulation setting for-a particular patient and his/her problem.

Briefly, the present invention is directed to a computer controlled system for fully automatic adjustment of a neurostimulation implant used in pain therapy and in treating neurological dysfunctions. The system as herein described has been found to fill a void in modern healthcare technology. The system's unique features dramatically decrease physician workload, increase productivity and increase efficiency of neurostimulators. The system is operated directly by the patient and substantially replaces the physician in the routine and tedious task of adjusting stimulation settings. The physician needs only to connect the patient to a patient interactive computer and select a protocol either on the physician's desktop computer or on the patient interactive computer 25. Thorough records are compiled during adjustment sessions and this data along with the optimum setting analysis results are available for post session review by a clinician.

The patient interactive computer is preferably a pentop tablet computer often including a transmitter interface which allows it to communicate with neurostimulation implants using radio frequency telemetry. (In the alternative, the transmitter interface may be embedded in the antenna.) The patient interactive computer and/or the physician's computer contain patient interactive software that has evolved out of extended periods of clinical research. The system may communicate using an infrared link with a printer for generating hard copy reports or with a desktop PC in the physician's office for providing patient data. The patient interactive computer also may communicate with a remote computer server through a telephone line, to obtain value added services or software updates.

The transmitter interface includes:
- a control interface unit communicating with the patient interactive computer to transmit data defining which one of a plurality of the predetermined programming codes has to be generated within the transmitter interface unit;
- a data memory unit adapted to store a plurality of parameters for the multiplicity of specific predetermined programming codes;
- a direct digital synthesizer interfacing with the control interface unit and receiving data from it;
- a programmable clock unit interfacing with the control interface unit and receiving data therefrom for clocking the direct digital synthesizer;
- a programmable gain/amplitude control unit interfacing with the control interface unit and receiving data from it; and
- a radio frequency amplifier coupled to an output of the direct digital synthesizer and amplifying an output signal received therefrom to be transmitted to the neurological stimulator device.

An alternative embodiment to the use of a radio frequency amplifier which in certain instances may not be an efficient method of driving the antenna, an alternative approach is taken for the transmitter interface unit. In the alternative embodiment, the transmitter interface unit comprises a control interface unit communicating with the patient interactive computer to interchange the data defined by the processing means of the patient interactive computer. A data memory system is adapted to store a plurality of parameters for the proprietary programming codes. Further a direct digital synthesizer (DDS) interfacing with the control interface unit for receiving data therefrom and outputting a carrier signal in response thereto is provided. A transistor circuitry is operatively coupled to the antenna for driving the antenna in on/off fashion. Finally a driving unit interfacing with the direct digital synthesizer is provided for generating gating pulses supplied to the transistor circuitry to drive such in a manner defined by the processing means within the patient interactive computer.

The driving unit may include either an analog comparator receiving at one input thereof the carrier signal (in analog form) from the DDS and comparing the carrier signal with a reference signal supplied to another input of the analog comparator. Alternatively, the driving unit includes a digital comparator receiving at one input thereof a carrier signal (in digital form) from the DDS and comparing the carrier signal to a reference code which is indicative of the width of a gating pulse to be output from the comparator. The output of the comparator (either digital or analog) is coupled to the transistor circuitry which in turn, drives the antenna.

Preferably, the transistor circuitry is an H-bridge which may include multiple inputs independently driven by the driving unit. Several implementations of the H-bridge circuit are contemplated in the scope of the present invention. In order to drive inputs of the H-bridge circuit independently, either multiple comparators are employed in the universal transmitter, or a single comparator with multiple outputs is used to supply gating control signals to the respective inputs of the H-bridge circuit.

In another alternative embodiment, the universal transmitter interface unit includes a balanced modulator for modulating the carrier signal. In this implementation, a combination of analog and digital techniques is used to provide a flexible and versatile modulation of the carrier signal generated at the digital direct synthesizer. In this embodiment, the transmitter interface unit further includes a low pass filter coupled between the output of the digital-to-analog converter (DAC) of the direct digital synthesizer and a first input of the modulator unit. A digital comparator having first and second inputs and coupled by the first input thereof to the output of the phase accumulator of the direct digital synthesizer and by the second input thereof to the control interface unit is included. A switching mechanism is incorporated for intermittently connecting a second input of the modulator unit to the output of the digital comparator and an output of the control interface unit.

In operation, a physician enters information about a patient into the system through either the physician's desktop computer or the patient interactive computers and chooses an optimization protocol from the available menu of the protocols. The patient interactive computer is then left in the hands of the patient for a fully automated session for the chosen optimization protocol.

A typical stimulation session involves a repeated cycle through the following steps:

1. Patient interactive computer automatically sets implant stimulation parameters;
2. Patient adjusts amplitude to meet one or more predefined criteria thresholds;
3. Patient draws area of stimulation coverage on a body outline;
4. Patient rates effectiveness of the setting on a 100 mm scale;
5. Patient interactive computer turns off stimulation and waits for stimulation sensation to clear;
6. Process proceeds again with a new stimulation setting until the session is finished.

The menu of optimization protocols referred to as testing/procedures before the data analysis may include the following operations in a predetermined combination thereof for a specific testing procedure:

1. A patient controlled amplitude adjustment procedure allowing the patient to adjust stimulation level to meet amplitude threshold;
2. Entry of an area of the pain experienced overlapped with an image of a human's body displayed on the display of the patient interactive computer;
3. Entry of a topography of paresthesias in response to the electrical stimulation overlapped with the image of the human's body displayed on the display of the patient interactive computer;
4. Entry of data corresponding to a degree of overlapping of the area of the pain experienced and the topography of paresthesias;
5. Establishing a pause between switching from one protocol to another;
6. Determination of 'multiple thresholds'.

For example, a bilateral optimization protocol would include collecting data from amplitude adjustment procedure (operation #1), collecting drawings (operations #2-4), collecting data related to patient ratings for the bilateral threshold with stimulation parameter selected in some particular fashion (operation #6). In some cases, the software allows a multi-level body-region entry by sequentially entering previous and successive measures of identical nature with reference to the image of the body displayed on the display of the patient interactive computer with the body-regions previously drawn displayed for the reference.

Preferably, when data entered fails to be consistent with expected or estimated data the patient is requested to redo the entry procedure.

Data collected for each stimulation setting is compared against data for other settings and against the previously entered pain drawing. A list of best settings is produced and sorted in rank order by the physician chosen criteria. The best settings may be printed in report format or they may be programmed automatically into an advanced patient stimulator as "presets", which present stimulation prescriptions that the patient may select electronically (the selection of a "pre-set" may be done even if the patient is not in the clinician's office).

The collected data may be transferred between many patient interactive computers. The data may be re-analyzed or used as the basis for further patient testing on other patient interactive computers, or it may be simply stored in a common data base for the center. Patient data and implant information can be transferred to remote data servers.

These and other novel features and advantages of this invention will be fully understood from the following Detailed Description and the accompanying Drawings.

BRIEF DESCRIPTION OF THE DRAWINGS

FIG. 6 is a block diagram of a direct digital synthesizer;

FIGS. 8A and 8B illustrate an amplitude adjustment screen with the screen shown in FIG. 8A drawn from the prototype neurostimulation system, while the screen shown in FIG. 8B is built using the Windows style control and text preferred for a commercial version;

DETAILED DESCRIPTION OF THE PREFERRED EMBODIMENTS

Figure 1:
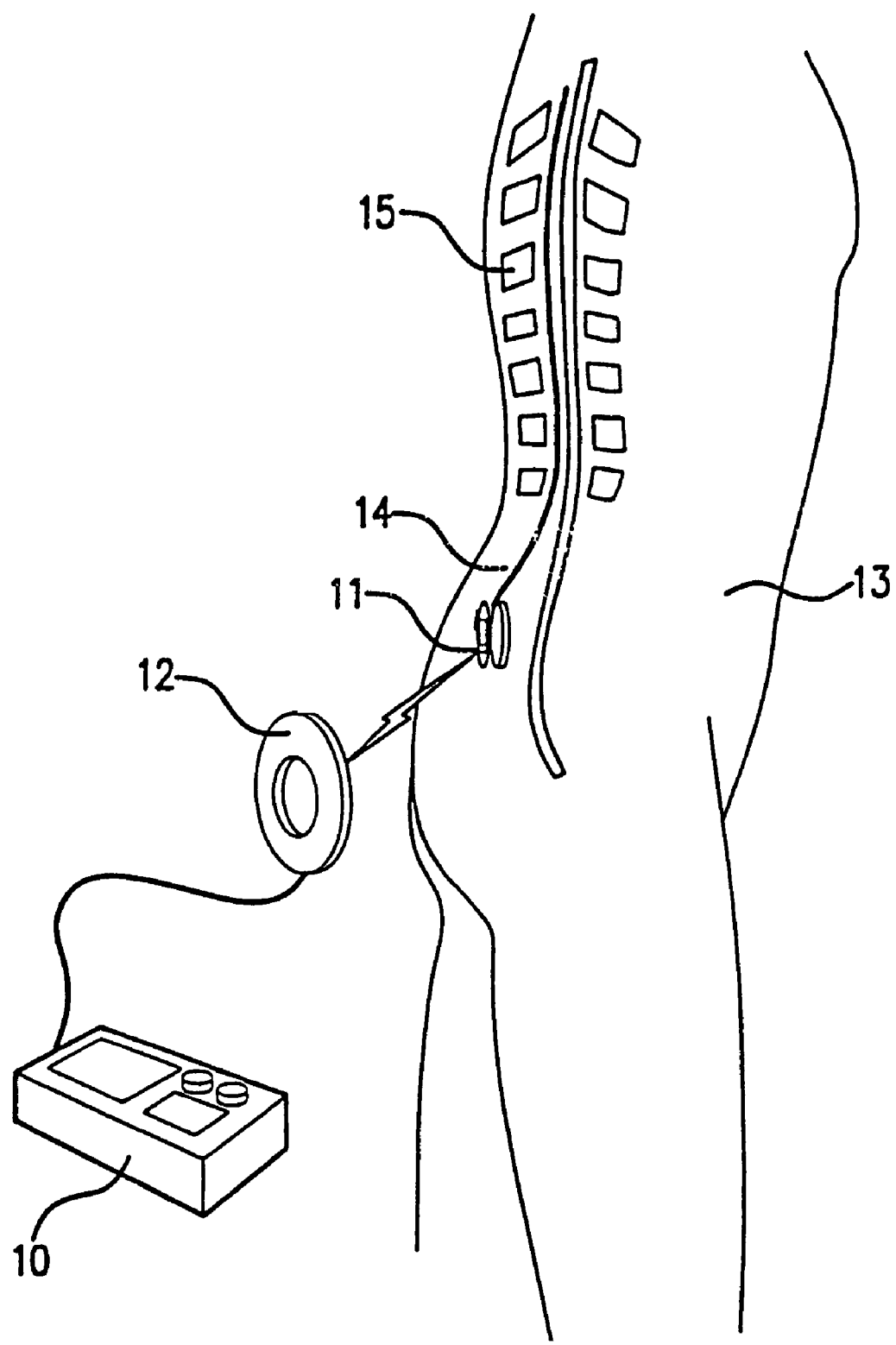
FIG. 1 is a scheme for neurological stimulation as is well-known in the prior art.
Figure 2:
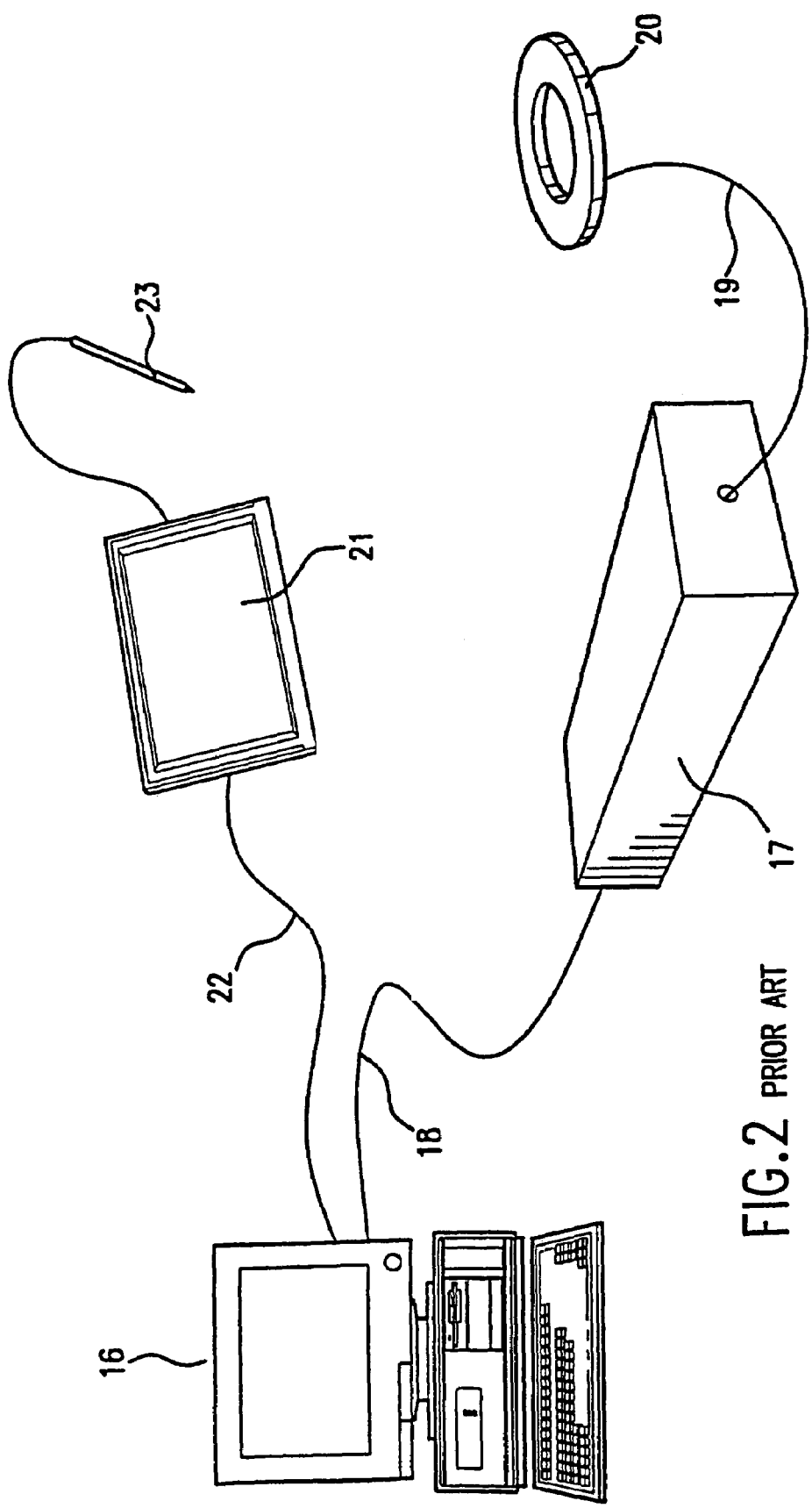
FIG. 2 illustrates the hardware of the computer controlled neurological stimulation system of the prior art.
Figure 3:
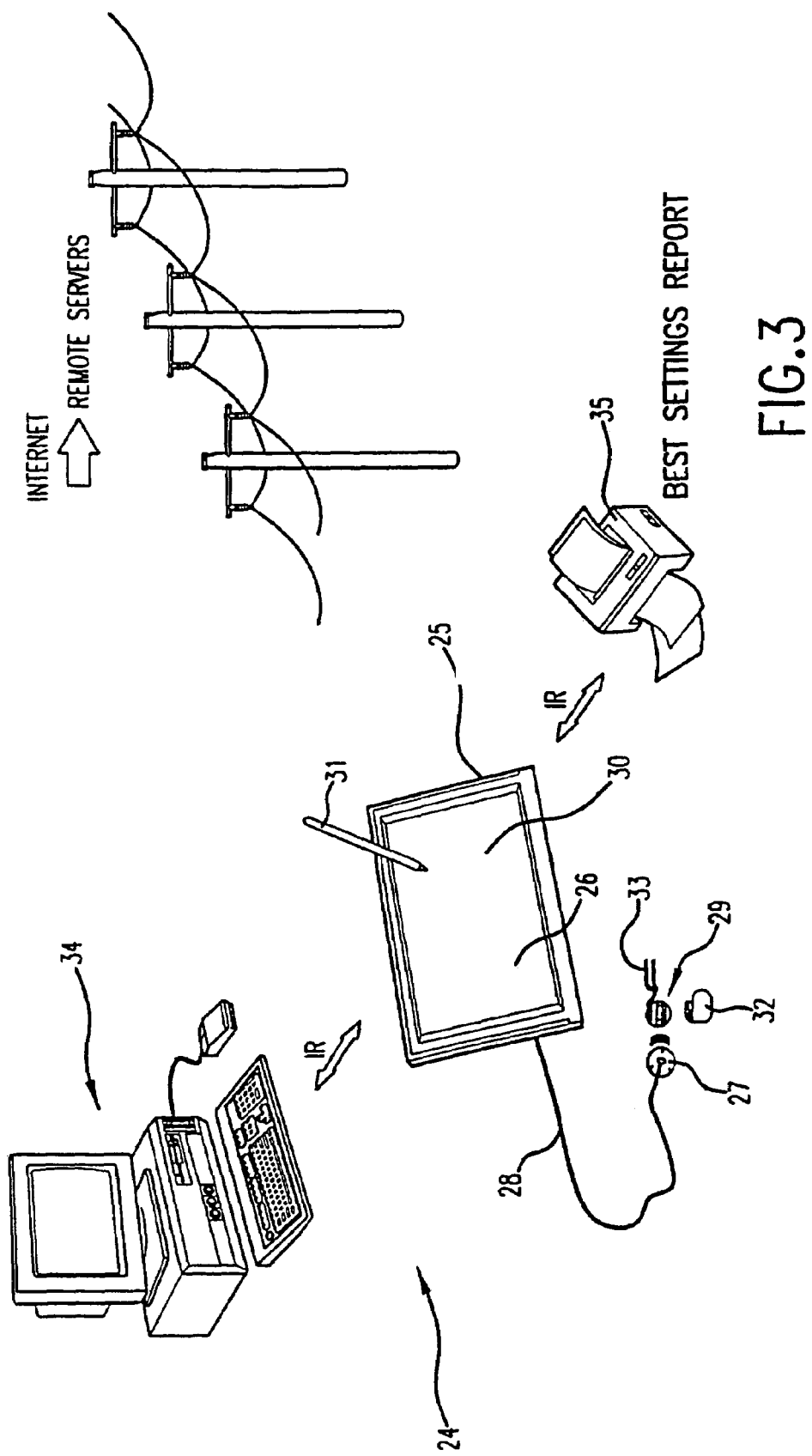
FIG. 3 illustrates a hardware for a patient interactive system for controlling neurostimulation of the present invention.
Figure 4A:
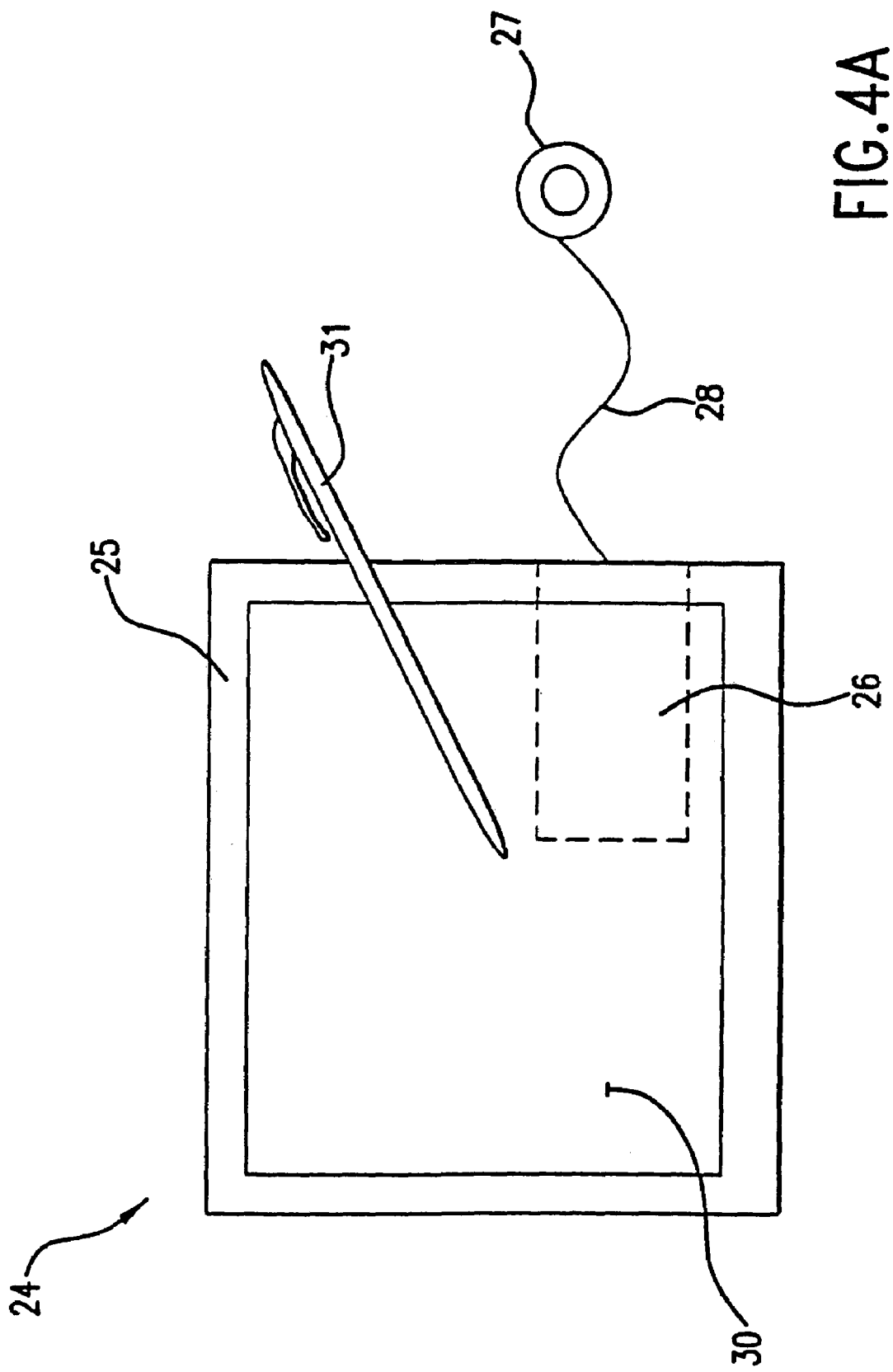
FIG. 4A is a block diagram of the patient interactive system for controlling neurostimulation of the present invention.
Figure 4B:
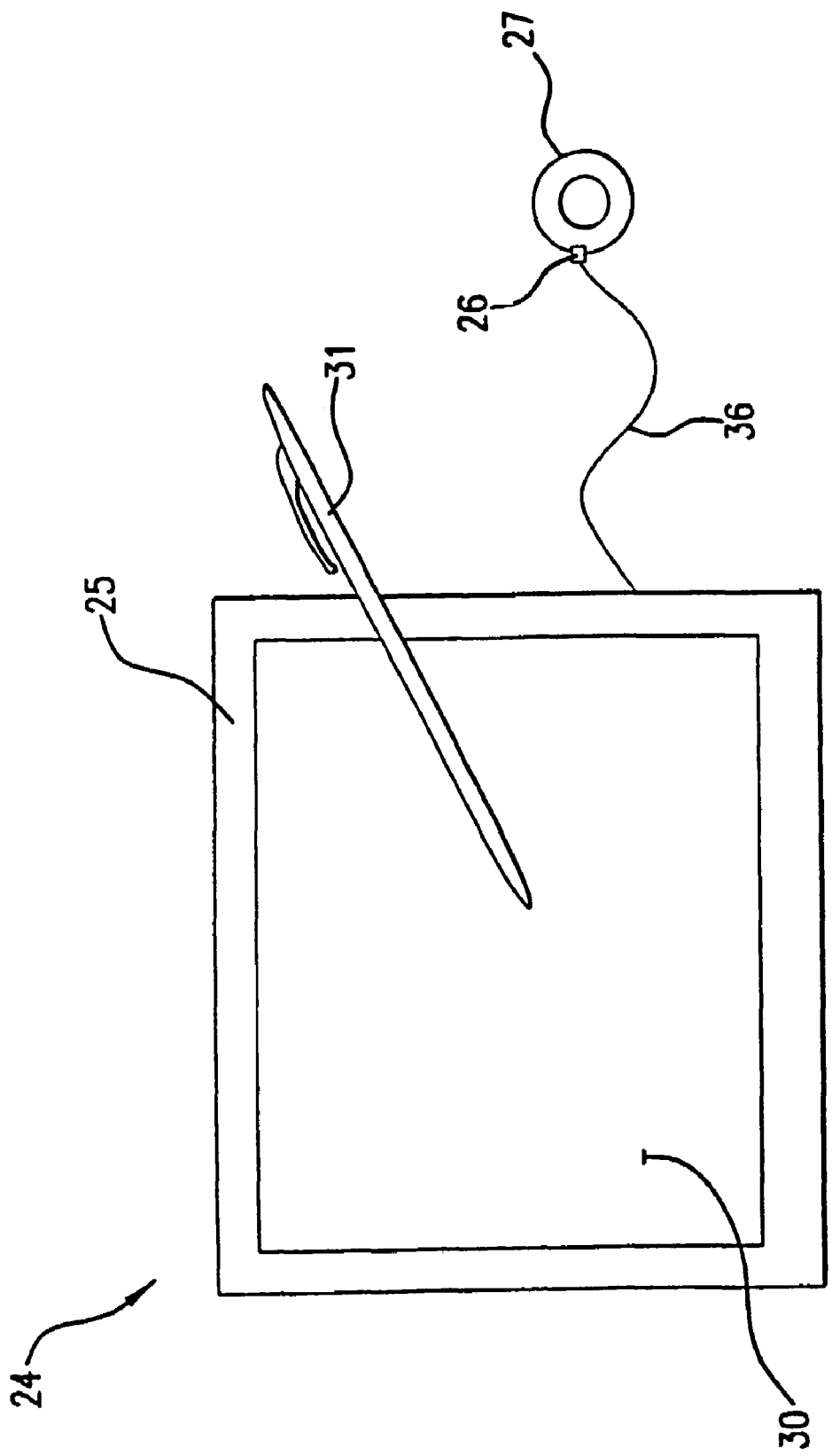
FIG. 4B is a block diagram of an alternative embodiment of the system of the present invention.

Referring to FIG. 3, a patient interactive system 24 of the present invention provides a computer controlled system for automatic adjustment of neurostimulation implants used in pain therapy and in treating neurological dysfunctions. The system 24 includes a patient interactive computer 25, which is preferably a pentop tablet computer, a transmitter interface unit 26 embedded either within the patient interactive computer 25 (as shown in FIG. 4A) or in antenna 27 (as shown in FIG. 4B). The antenna 27 is coupled to the transmitter interface unit 26 embedded in the computer 25 through a communication channel which may be a PCMCIA bus 28. This serves the function of a radio frequency (RF) link between the transmitter interface unit 26 and neurological spinal cord stimulation (SCS) implants 29. As shown in FIG. 4B, the transmitter interface 26 built into the antenna 27 communicates with the computer through the antenna cable, which may be a USB bus.

The patient interactive computer 25 includes a display 30 displaying images and messages for the patient and accepting the feedback from the patient. This then provides a mechanism for direct communication between the patient and the patient's interactive computer 25. A stylus 31 provides for entry of the patient's response into the patient interactive computer 25.

The patient interactive computer 25 with the transmitter interface unit 26 and the patient interactive software (which altogether comprise the present invention) are collectively termed the neurological stimulation system (NSS). The NSS controls the associated implanted receiver 32 and the electrodes 33 of the neurological stimulator implant 29.

The system of the present invention further includes a physician's desktop computer 34 which communicates with the patient interactive computer 25 telemetrically, preferably through an IR (infrared) link. The patient interactive computer 25 can also communicate using an infrared link with a printer 35 for generating hard copy reports. Additionally, by using a telephone line, the patient interactive computer 25 may also communicate with an internet web site or any remote computer server to obtain value added services or software updates.

FIGS. 4A and 4B show the patient interactive system of the present invention as a self-contained unit comprising the pentop patient interactive computer 25, transmitter interface unit 26, and antenna 27 communicating with the transmitter interface unit 26 through the communication bus 28 and the stylus 31. The transmitter interface unit 26 integrally embedded in the computer 25 or in the antenna 27 includes RF circuitry generating coded signals transmitted through the antenna 27 to the implants 29.

Direct electrical spinal cord stimulation (SCS) is considered an effective therapy for pain relief and is accomplished by implanting neurological stimulation devices into predetermined areas over the spinal cord and stimulating them with electrical pulses of a predetermined frequency, amplitude, and pulse width.

As shown in FIG. 3, the implant 29 comprises the radio frequency receiver 32, a lead, and an array of electrodes 33. The lead may be the insulated carrier for several electrodes. The lead is displayed in the epidural space using a percutaneous needle entry technique or open surgery. The lead contains a plurality of wires from each electrode for connection to the implanted radio frequency receiver 32.

An electrode 33 is the active conductive area of the lead and typically, are formed of platinum-iridium alloy. For providing neurostimulation, a plurality of pairs of positive and negative electrodes 33 are used. As it is known to those skilled in the art, more than two electrodes are preferred to be involved in SCS, which are usually called an electrode array. These electrodes can be programmed independently to be negative, positive, or off which allows electrical fields to be generated across contacts on each individual lead, as well as across the two opposing leads to create desirable paresthesias.

An array of electrodes used in the present invention may be arranged in a so-called guarded electrode array which is a selection of three adjacent electrodes where the electrode in the middle or center has an opposite polarity from the other two electrodes. Preferably, the middle electrode is negative, and constitutes a guarded cathode, or a split anode. The so-called across the lead guarded cathode can be also used in which the negative electrode is on one lead, and the two nearest electrodes on the contralateral lead are positive. It is clear to those skilled in the art that a plurality of stimulation settings (or programs) exist, each of which determines electrode activation including the number of electrodes activated, the polarity of electrodes, frequency, pulse width, and amplitude.

Four electrodes may have 50 separate usable combinations of polarities. Eight electrodes may have 6,050 separate valid combinations of polarities. Sixteen electrodes can have over 62,000,000 separate usable combinations of polarities. Beyond this possible adjustment, neurostimulators can set frequency of stimulation between 1 Hz and 1500 Hz, set the pulse width of stimulation between 10 and 1000 microseconds and vary the amplitude of stimulation. Without the computerized system for controlling neurostimulation which would be capable of collecting and processing all these combinations in a rapid and organized fashion, the physical capabilities of medical staff to adjust stimulators for each patient would be very quickly overwhelmed. The system of the present invention due to its unique features, allows for quick and efficient collection of data, processing the collected data and adjustment of the neurostimulation settings to each patient for each particular situation.

As each implant 29 is adapted for responding to a particular proprietary programming code, it is an important feature of the present invention that the transmitter interface unit 26 of the present invention be capable of generating and transmitting any one of a plurality of existing proprietary programming codes, thereby making the system of the present invention a "universal system" for being capable of adaptation to a wide variety of implants 29 implanted into the patient. The approach that has been taken in the prior art is that should the system communicate with multiple different types of implantable devices, it must have a specific circuitry to emulate types of transmitters. The manner of emulating different types of transmitters in the subject invention is to provide a programmable circuit that generates arbitrary waveforms. These arbitrary waveforms can then imitate the proprietary codes generated by the proprietary systems. Thus, a separate system can communicate with each type of implantable device by using the programmable circuit that generates arbitrary waveforms.

The system of the present invention achieves arbitrary waveforms by modulating carrier signals with a direct digital synthesizer and programmable control, thereby providing for a universal transmitter within the system. Therefore, the system of the present invention can be considered a "universal" patient interface having a transmitter that can generate any one of the different proprietary pulse codes since it can imitate any one of the proprietary transmitters and thus can communicate with any type of the implanted receivers for implant devices, including RF-powered implants as well as implantable pulse generators (IPGs) with self-contained power sources.

Figure 5:
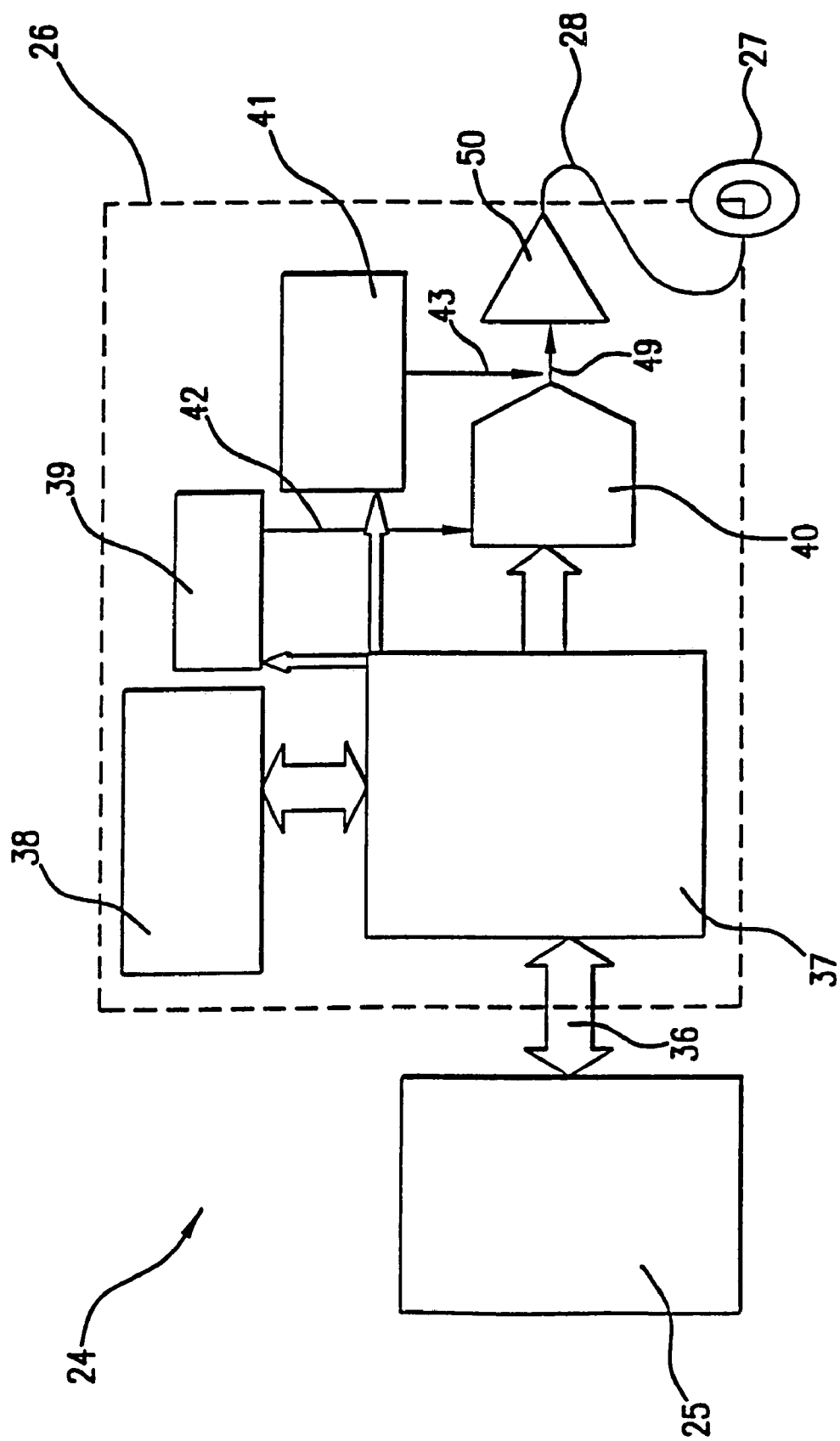
FIG. 5 is a block diagram of the universal transmitter interface unit for generating arbitrary waveforms and programming codes for communicating with implantable devices.

The transmitter interface unit 26, also referred to as universal transmitter, as shown in FIG. 5, is integrally embedded into the patient interactive computer 25 and communicates therewith through the communication channel 36 that may be a parallel bus, a PCMCIA bus, a serial interface like RF232 link, or a local area network. If the transmitter interface 26 is built into the antenna 27, the antenna cable serves as communication channel between the RF interface 26 and the host computer.

The communication channel 36 serves for transmitting data between the patient interactive computer 25 and the transmitter interface unit 26 in both directions. The patient interactive computer 25 stores and runs the software developed for interaction with the patient and constitutes the novel subject of the present invention. The software will be described in detail in further paragraphs.

The patient interactive computer 25 also holds the data that is being passed back and forth through the communication channel 36 which are the descriptions of what kind of pulse code the universal transmitter is to generate. Basically, the patient interactive computer 25 by means of transmitting the data to the universal transmitter describes to the transmitter interface unit how it is going to generate pulse codes which will then translate the instructions to the implanted receiver 32 internal the patient's body that will generate the appropriate stimulus pattern, i.e., how many and which of the electrode combinations are going to be involved, their polarities, amplitudes, frequencies of the pulses, and width thereof as well as how many pulses to produce.

The transmitter interface unit of the present invention is envisioned in several embodiments. In one of the embodiments, best shown in FIGS. 5 and 6, the transmitter interface unit, or the universal transmitter, 26 includes control interface circuitry 37 directly communicating with the patient interactive computer 25 for receiving and transmitting data therebetween. The control interface circuitry 37 may be built on the basis of microprocessor, or microcontroller, or programmable logic-like FPGA, PLD, ASIC, or reconfigurable computer logic. Any other implementation of the control interface circuitry for the universal transmitter are also contemplated in the scope of the present invention.

The control interface circuitry 37 interfaces with data memory 38 which stores the variety of pulse parameters that are to be generated. The data memory may be any kind of memory known to those skilled in the art, including SRAM, EEPROM, UVPROM, SDRAM, DRAM, etc. Since the present invention allows a variety of frequencies, pulse widths, amplitude, that will allow physicians to provide unique stimulation paradigms with the patient and that provide better or wider treatment paradigms, the data memory unit 38 is necessary within the universal transmitter 26 for holding the various different pulse frequencies, pulse widths, pulse amplitude, etc.

In essence, the data memory 38 serves the function of a look-up table. When the patient interactive computer 25 "describes" to the control interface circuitry 37 what type of implants 29 the universal transmitter is to actuate, what kind of the electrical simulation pulses it is to transmit, and how many pulses are to be transmitted, the control interface circuitry 37 communicates with the data memory 38 and receives therefrom data concerning stimulation pulse parameters.

In response to the data received from the data memory 38, the control interface circuitry 37 interfaces with the programmable clock 39, direct digital synthesizer 40, and feeds data to the programmable gain/amplitude control unit 41. When the control interface circuit 37 receives an appropriate data packet from the data memory circuit 38, it programs the programmable clock 39, i.e., the control interface circuitry 37 sets a specific frequency range that then drives and clocks the direct digital synthesizer 40.

The programmable gain/amplitude control 41 provides the mechanism for amplitude modulation of the carrier signal. In essence, the programmable gain/amplitude control 41 generates the desired amplitude envelope around the carrier signal. Additionally, the programmable gain/amplitude control 41 can invert the polarity of the signal to effect a phase reversion, thus providing phase encoding of the programming wave form.

The direct digital synthesizer 40 generates a continuous sine wave according to the control interface circuitry 37 instructions. The control interface circuitry 37 simultaneously programs and controls the gain in the programmable gain/amplitude control 41. By putting the appropriate amplitude modulation around the carrier signal generated by the direct digital synthesizer 40, the system achieves amplitude modulation. The phase encoding, as discussed in previous paragraphs, is achieved by inverting the gain, so that the universal transmitter provides various types of modulation of the carrier's signal. By clocking the direct digital synthesizer 40 by means of the programmable clock 39 through the bus 42, the direct digital synthesizer 40 generates frequency encoding in addition to amplitude modulation with the programmable clock 39 providing wide frequency bandwidth.

A direct digital synthesizer often can generate only one or two decades of frequency bandwidths. Changing the clock frequency, the center point of the bandwidth of the direct digital synthesizer 40 may be offset. If the clock frequency changes by a factor of ten, then the center point of the direct digital synthesizer 40 bandwidth is displaced by a factor of ten. This allows the direct digital synthesizer 40 to generate carrier frequency that varies content of kilohertz to tens of megahertz. The programmable gain/amplitude control 41 interfaces the direct digital synthesizer 40 through the communication channel 43.

As shown in FIG. 6, the direct digital synchronization 40 includes a binary adder 44, receiving two binary values on the input thereof which represent frequency, a D-type register 45 coupled to the output of the binary adder 44, a look-up table 46 containing a sine wave connected to the output of the phase accumulator consisting of the binary adder 44 and the D-type register 45, a digital-to-analog converter 47 receiving instantaneous amplitude value of the sine wave from the look-up table 46, a low pass filter 48 receiving the stepped analog output from the digital-to-analog converter 47, and outputting filtered output in the form of a continuous sine wave.

Interface circuitry 37 of the universal transmitter 26 presents an incremental value that is inversely proportional to frequency received from the data memory 38. This incremental value is continuously added to the phase received from the output of the D-type register 45, thereby generating an address vector into the look-up table 46 that contains a single cycle of a pure sine wave. The output from the look-up table 46 presents an instantaneous value of the amplitude of the sine wave to the digital-to-analog converter 47.

The instantaneous phase number at the output of the D-type register 45 in combination with the incremental value representing frequency received from the control interface circuitry 37 becomes that vector for the look-up table 46. The direct digital synthesizer 40 finally filters the resulting analog signal from the digital-to-analog converter 47 with the low pass filter 48. The continuous sine wave from the output of the low pass filter 48 is then modulated by means of the programmable gain/amplitude control unit 41 as it was described in previous paragraphs. In this manner, the carrier signal from the direct digital synthesizer 40 properly modulated, i.e., amplitude modulated, phase modulated, frequency modulated, or any combination of those modulations, is supplied through the communication channel 49 to a radio frequency amplifier 50 which amplifies the output signal of the universal transmitter 26 and drives the antenna 27.

As described in previous paragraphs, the universal transmitter 26 of the present invention generates arbitrary waveforms to program and communicate with implantable devices 29. Therefore, the universal transmitter replaces numerous proprietary designs with a single programmable design which arises from a unique combination of programmable control, direct digital synthesis, gain control, and clock control.

Briefly summarizing the above discussion, the universal transmitter generates any of a plurality of proprietary programming codes for the implantable devices by means of interfacing the control interface circuitry 37 with the patient interactive computer 25 to receive commands therefrom and data to prepare a specific program waveform. The control interface circuitry 37 then controls the direct digital synthesizer 40, the programmable clock 39, and the programmable gain/amplitude control unit 41 to generate the specific required programming waveform and pattern to properly stimulate the implantable devices 29.

In a number of environments, use of the RF amplifier 50 of FIG. 5 may fail to provide an efficient method to drive the antenna 27. In order to drive the antenna 27 in a more efficient fashion an alternative design of the transmitter interface unit 200, best shown in FIG. 15, may be employed which includes:

control interface circuitry 37 interfacing with the patient interactive computer 25, data memory 38 which stores pulse parameters such as frequency, width of the pulses, amplitude, rate of repetition, etc., a direct digital synthesizer 210 (which may differ from the direct digital synthesizer 40 of FIGS. 5 and 6), a transistor circuitry 220 for driving the antenna 27 in ON/OFF fashion, and a driving unit 230 generating gating pulses for driving the transistor circuitry 220.

Figure 16:
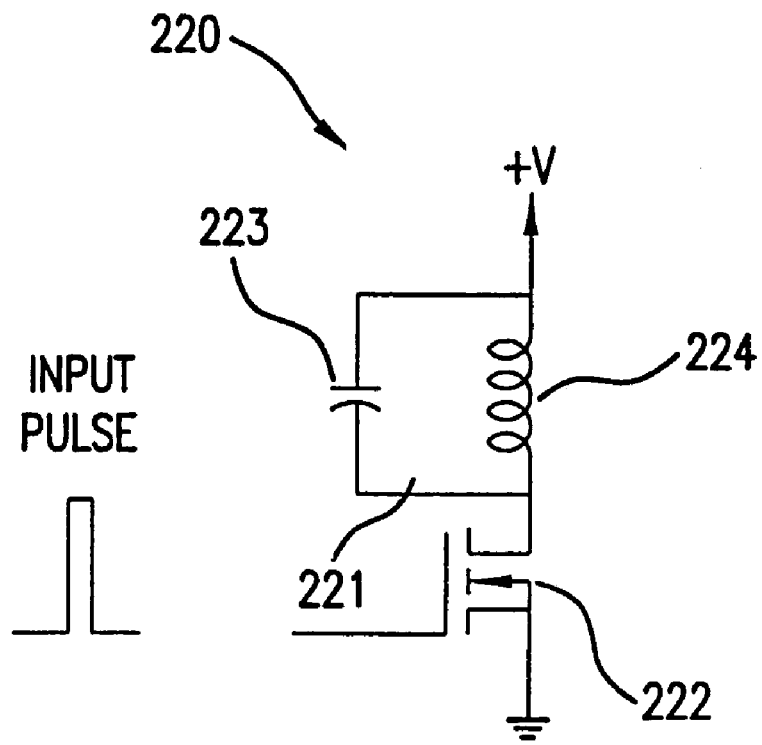
FIG. 16 shows a schematic of a tuned tank circuit for generating an RF field for driving the antenna.
Figure 16A:
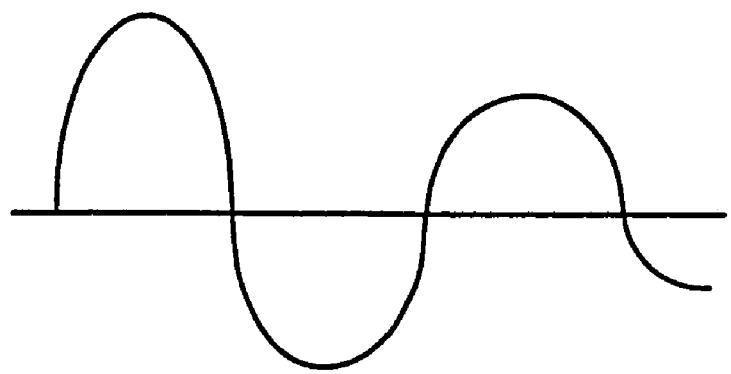
FIG. 16A is a diagram showing an output across RF coil of FIG. 16.

Several embodiments of the transistor circuitry 220 are envisioned for driving the antenna 27 in ON/OFF fashion. As shown in FIG. 16, a tuned tank circuit 221 includes a transistor 222 (gated MOSFET) with the parallel tuned LC circuit having the capacitor 223 and the inductance 224 which is the coil of the antenna 27. Once the input pulse (gating pulse) is supplied to the gated MOSFET, the transistor 222 oscillates with a characteristic relaxation frequency determined by the parameters of the LC circuit. Since the tuned LC circuit is used as collector load of the transistor 222, an output (bursts of current) shown in FIG. 16A appears across RF coils 224 of the antenna 27. The tuned tank circuit 221 uses the fewest components and is inexpensive but may not be as efficient as other transistor circuitries 220 contemplated in the scope of the present invention and described in further paragraphs.

Figure 17:
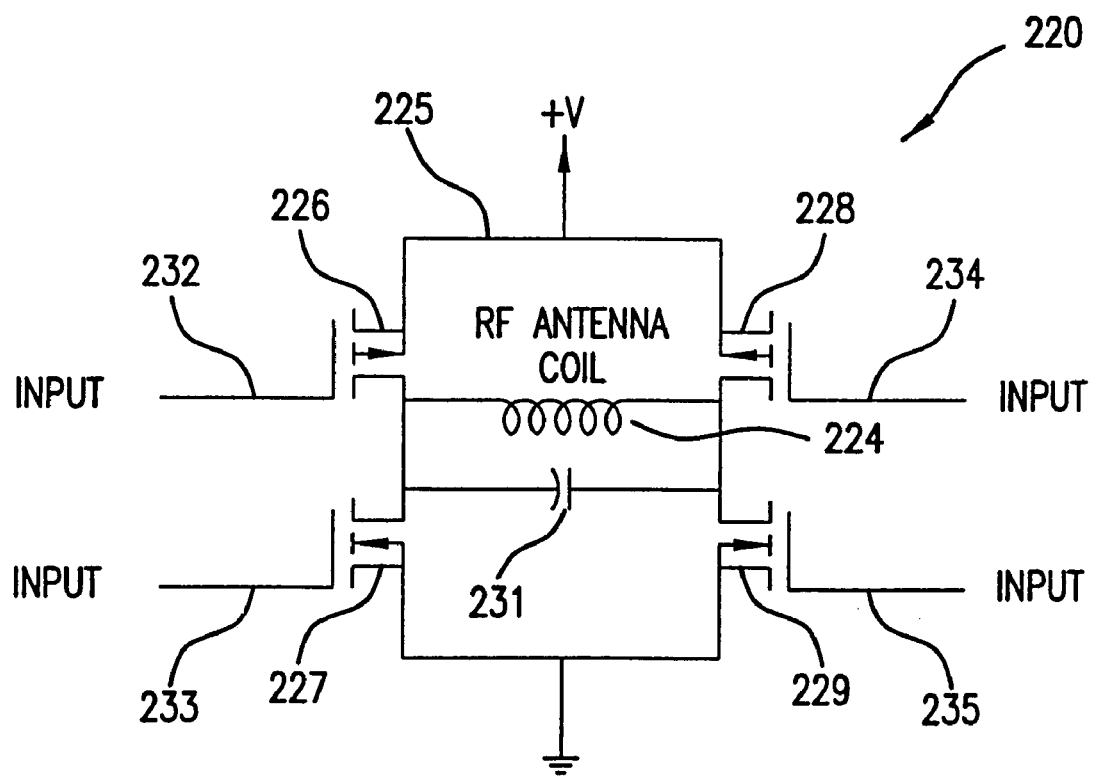
FIG. 17 is a schematic of an H-bridge circuit for generating an RF field for driving the antenna.

FIG. 17 shows another transistor circuitry 220 that produces RF energy for driving the antenna 27 using the H-bridge configuration 225. The H-bridge configuration 225 employs four transistors 226-229 (gated MOSFETs) with the RF antenna coil 224 of the antenna 27 coupled between the transistors 226 and 228 in parallel with the capacitance 231. As can be seen, each of the transistors 226-229 is gated independently via four separate inputs 232-235.

By turning the inputs 232 and 235 simultaneously momentarily ON and then OFF followed by turning the inputs 233 and 234 simultaneously in a similar manner, the current flow through the RF coil 224 generates RF energy. In this manner, the antenna 27 is driven in ON/OFF fashion to transmit programming codes to the neurological stimulation devices implanted in the body of a patient to provide electrical stimulation to the nervous tissue in accordance with a prescribed protocol.

Figure 18:
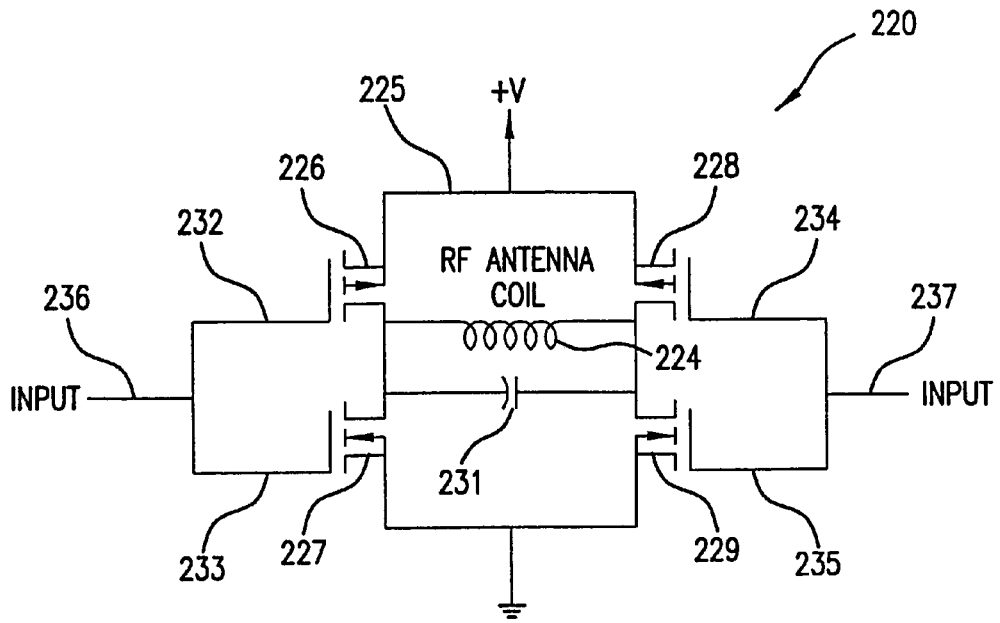
FIG. 18 is an alternative H-bridge circuit for generating an RF field for driving the antenna.

Independent sequencing of the four inputs 232-235 of the H-bridge 225 provides for highly efficient operation. In order to reduce the number of components necessary to drive the antenna 27, the inputs 232 and 233 may be combined into a single input 236 as shown in FIG. 18, and inputs 234 and 235 of FIG. 17 may be combined into input 237. In this embodiment, the inputs 236 and 237 are driven as two independent inputs to generate the RF field across the antenna coil 224. The efficiency of the circuitry shown in FIG. 18 is sufficient to drive the antenna 27 although lower than the efficiency of operation of the H-bridge circuit 225 shown in FIG. 17. The H-bridge with two independent inputs 236 and 237 in certain instances may also suffer from short circuit crossover transients which may occur through each transistor pair (236 and 237) or (238 and 239) when one transmitter in each pair is turning ON and the other is turning OFF; as is well known to those skilled in the art.

Figure 19:
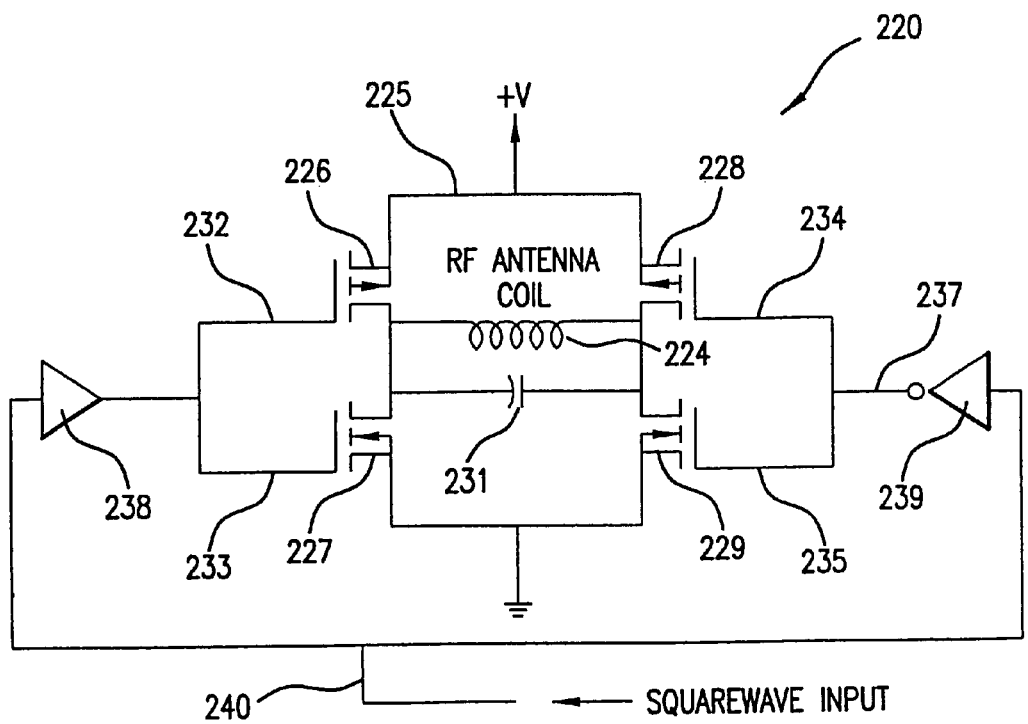
FIG. 19 is another alternative implementation of an H-bridge circuit for driving the antenna.

Shown in FIG. 19 is another implementation of the H-bridge configuration of the transistor circuitry 220 which is similar to the H-bridge configuration shown in FIG. 18

(with two independent inputs) having a non-inverting buffer amplifier 238 coupled to the input 236 and the inverting buffer amplifier 239 coupled to the input 237 of the H-bridge configuration of the transistor circuitry 220. The transistor circuitry 220 shown in FIG. 19 requires a substantially square wave input 240 (50% duty cycle) to reduce any DC component in the RF antenna coil 224.

It is believed that the most efficient approach of driving the antenna coil is shown in FIG. 17, although all other transistor circuitries 220, shown in FIGS. 16, and 18-19, provide sufficient drive for the antenna 27. The transistors in the transistor circuitries 220, shown in FIGS. 16-19, operate as switches and hence their operation is more efficient than the linear operation of transistors within the RF amplifier 50 shown in FIG. 5. This finding is to be taken into consideration when different levels of operation efficiency is needed in the neurostimulation system of the present invention.

Figure 15:
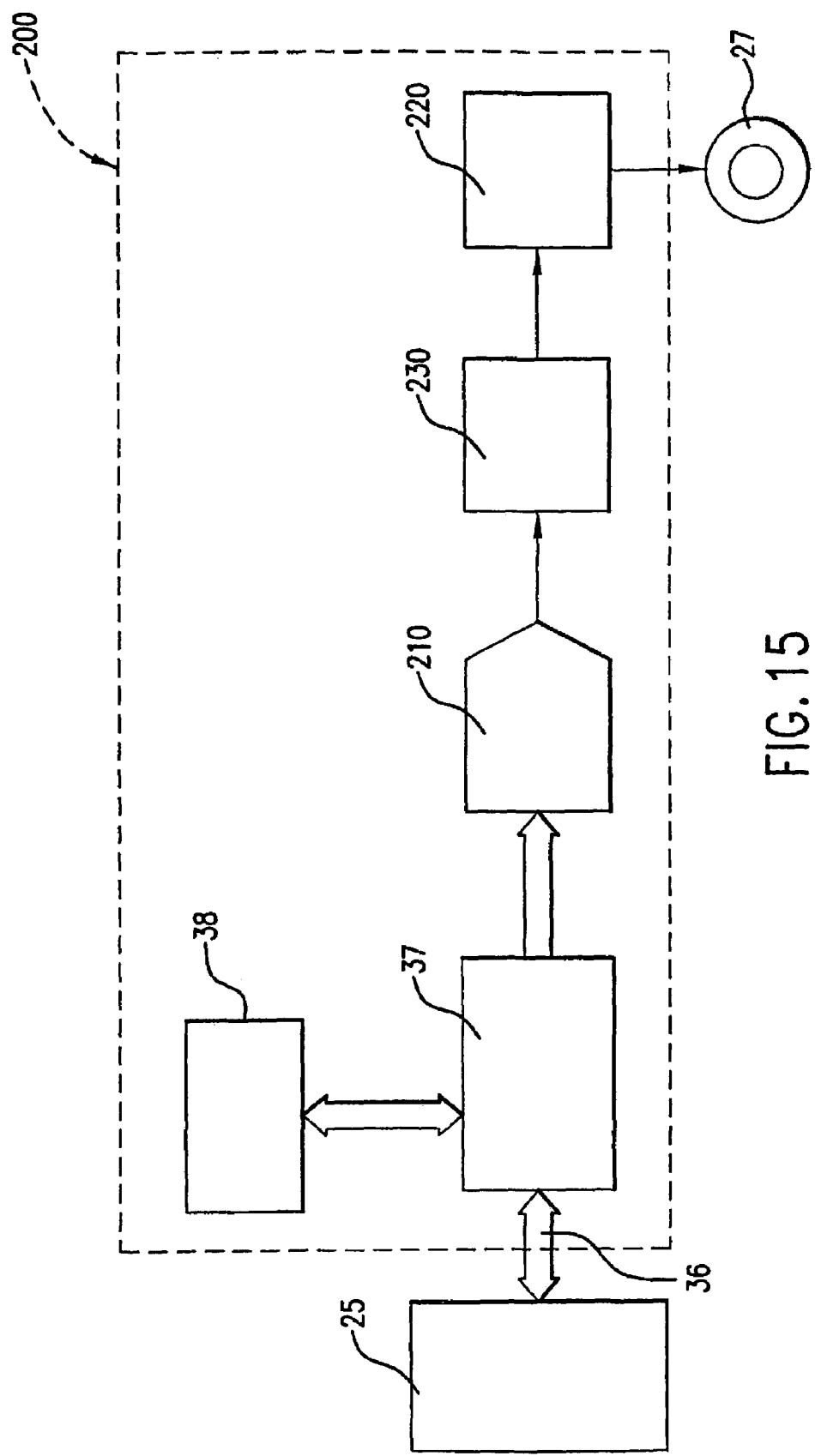
FIG. 15 is a block diagram of the universal transmitter interface unit in alternative embodiment thereof.
Figure 20:
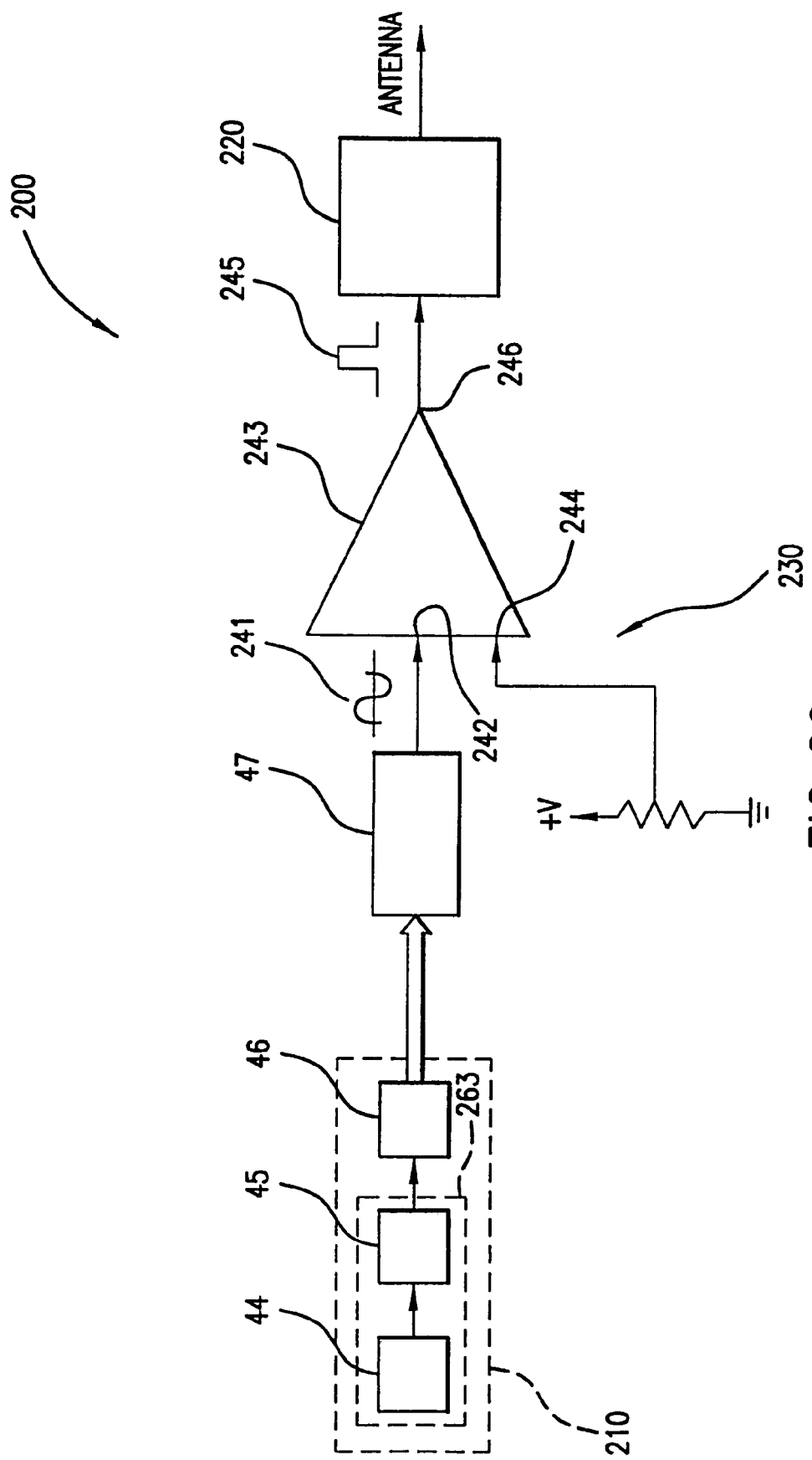
FIG. 20 is a block diagram of the driving unit for generating gating pulses for driving transistor circuits of FIGS. 16-19.

In order to drive either of the transistor circuits 220 shown in FIGS. 16-19, the following embodiments of the driving unit 230, FIG. 15, are envisioned within the scope of the present invention. As shown in FIG. 20, the driving unit 230, uses an analog signal 241 obtained on the output of the digital-to-analog converter (DAC) 47 coupled to the output of the direct digital synthesizer 210 which includes the phase accumulator 263 (binary adder 44 and D-type register 45) and the look-up table 46.

The analog signal 241 which is generated by the digital direct synthesizer 210 and converted into analog signal by the DAC 47 is supplied to an input 242 of an analog comparator 243. The reference signal, corresponding to a desired pulse width set point is supplied to a second input 244 of the analog comparator 243. The analog comparator 243 compares the incoming signal 241 and the reference signal at the input 244 and once the match is found, a digital pulse 245 of a predetermined width is output from the output 246 of the analog comparator 243 which is used as a gating digital pulse for driving transistor circuits 220 and associated buffer amplifiers 239 and 240.

Figure 21:
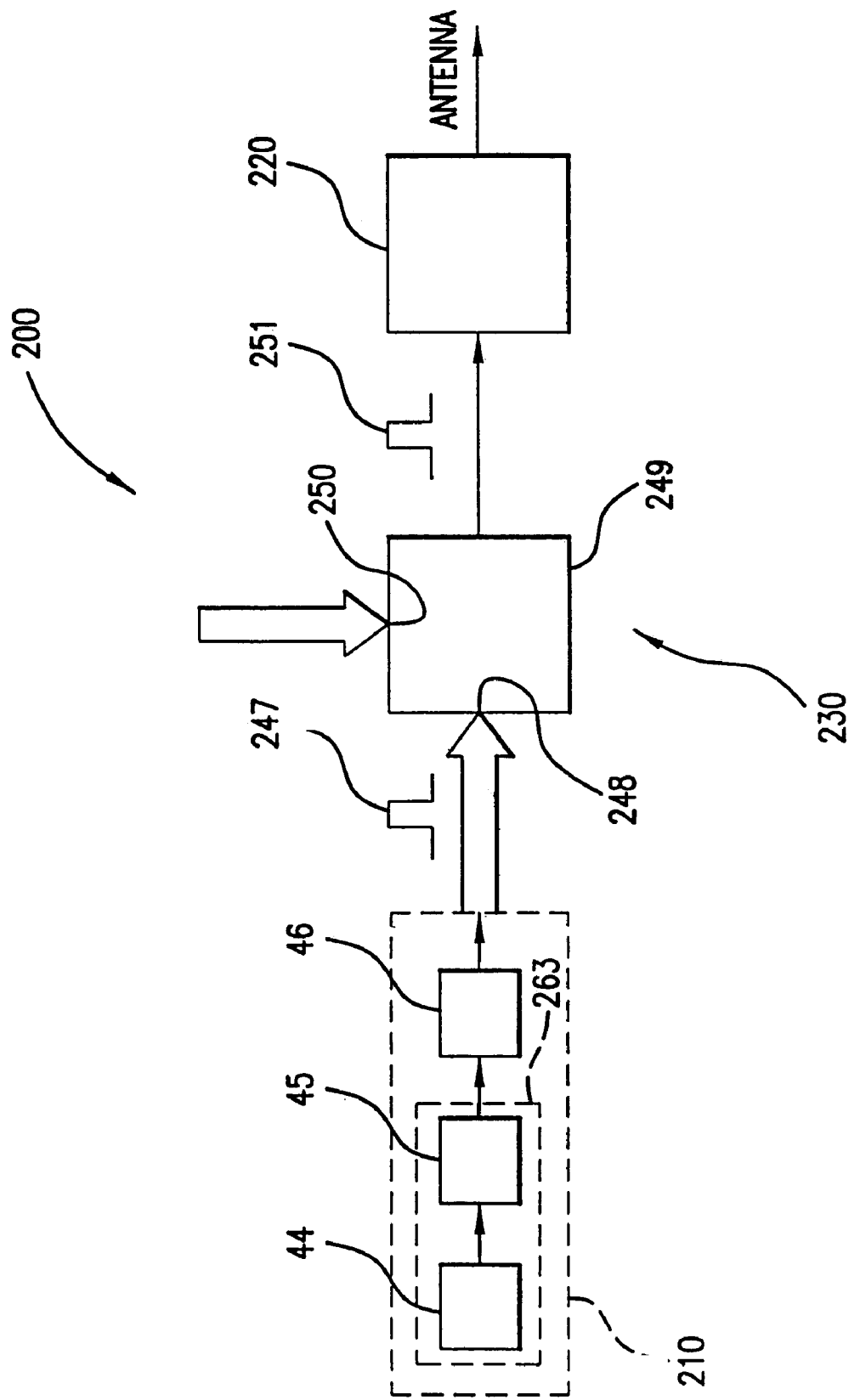
FIG. 21 is a block diagram of an alternative embodiment of the driving circuit for generating gating pulses for driving transistor circuits of FIGS. 16-19.

An alternative and preferred embodiment of the driving unit 230 is shown in FIG. 21 in which the digital signal 247 generated by the direct digital synthesizer 210 (which includes the phase accumulator 263 and the look-up table 46) which is supplied to the input 248 of a digital comparator 249. Another input 250 of the digital comparator 249 is coupled to a digital code representing the pulse width set point serving as a reference for comparison with the digital signals 247. When the match between the reference signal and the digital signal 247 is found, the digital comparator 249 generates a digital gating pulse 251 for driving transistor circuits 220 shown in FIGS. 16-19, and associated buffer amplifiers. The reference signals representing the pulse width set points in both digital and analog form, are supplied from the control interface circuitry 37 under control of the patient interactive computer 25.

Figure 22:
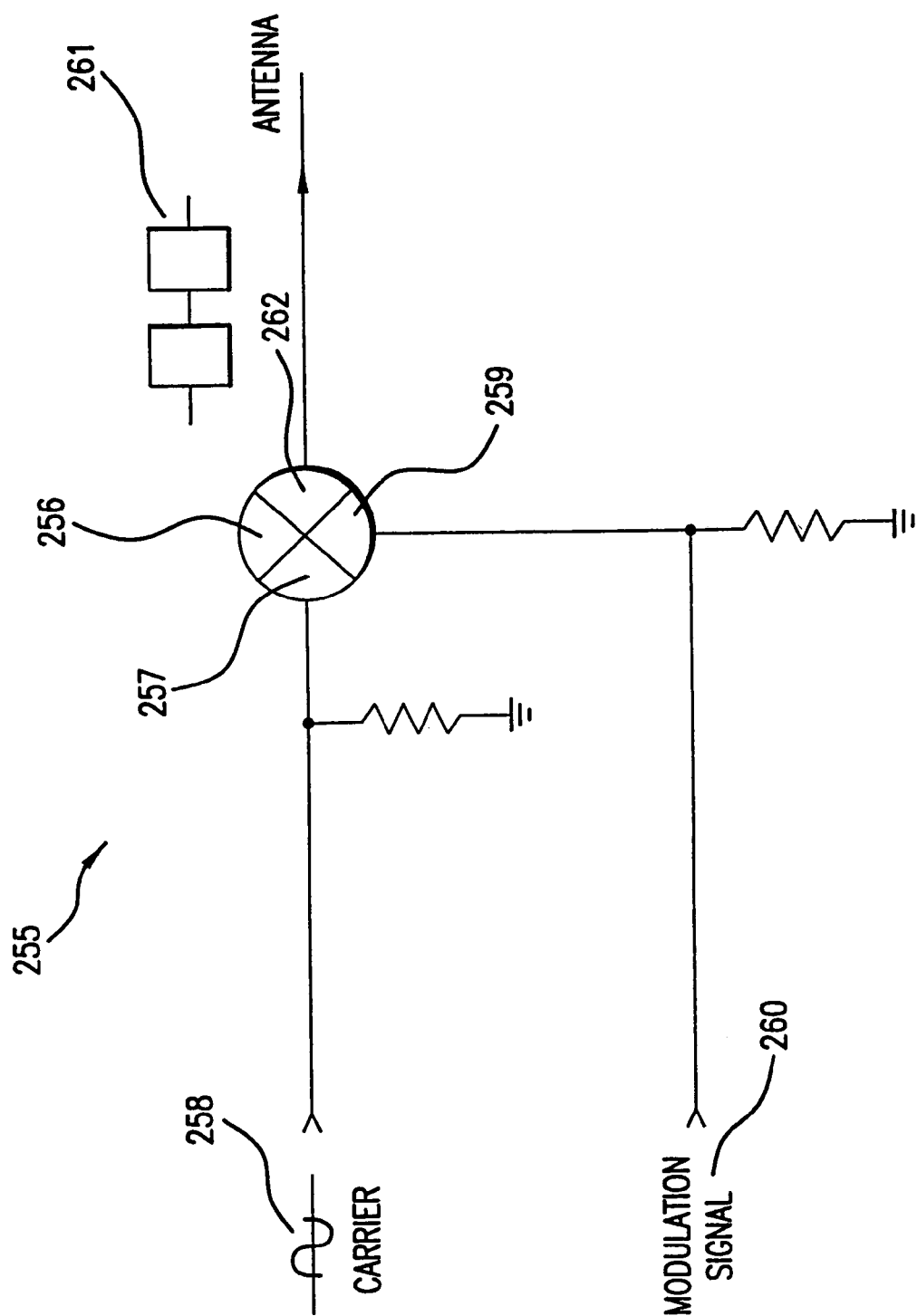
FIG. 22 is a simplified block diagram of a technique for modulation of the carrier signal.

In another alternative embodiment of the transmitter interface unit of the present invention, a combination of digital and analog techniques can be used for modulating a signal generated in the direct digital synthesizer 210 so that the neurological stimulation devices 29 can be electrically stimulated in accordance with uniquely prescribed protocol in a flexible and versatile manner. As shown in FIG. 22, an alternative transmitter interface unit 255 includes a balance modulator 256 where an analog carrier signal 258 is received at input 257 which is generated at the direct digital synthesizer 210. The input 259 receives a modulation signal 260 for modulating the carrier signal 258. The modulated signal 261 formed as the product of the analog signal 258 and modulation signal 260 is obtained at the output 262 of the balance modulator 256 and is supplied to the antenna 27.

Figure 23:
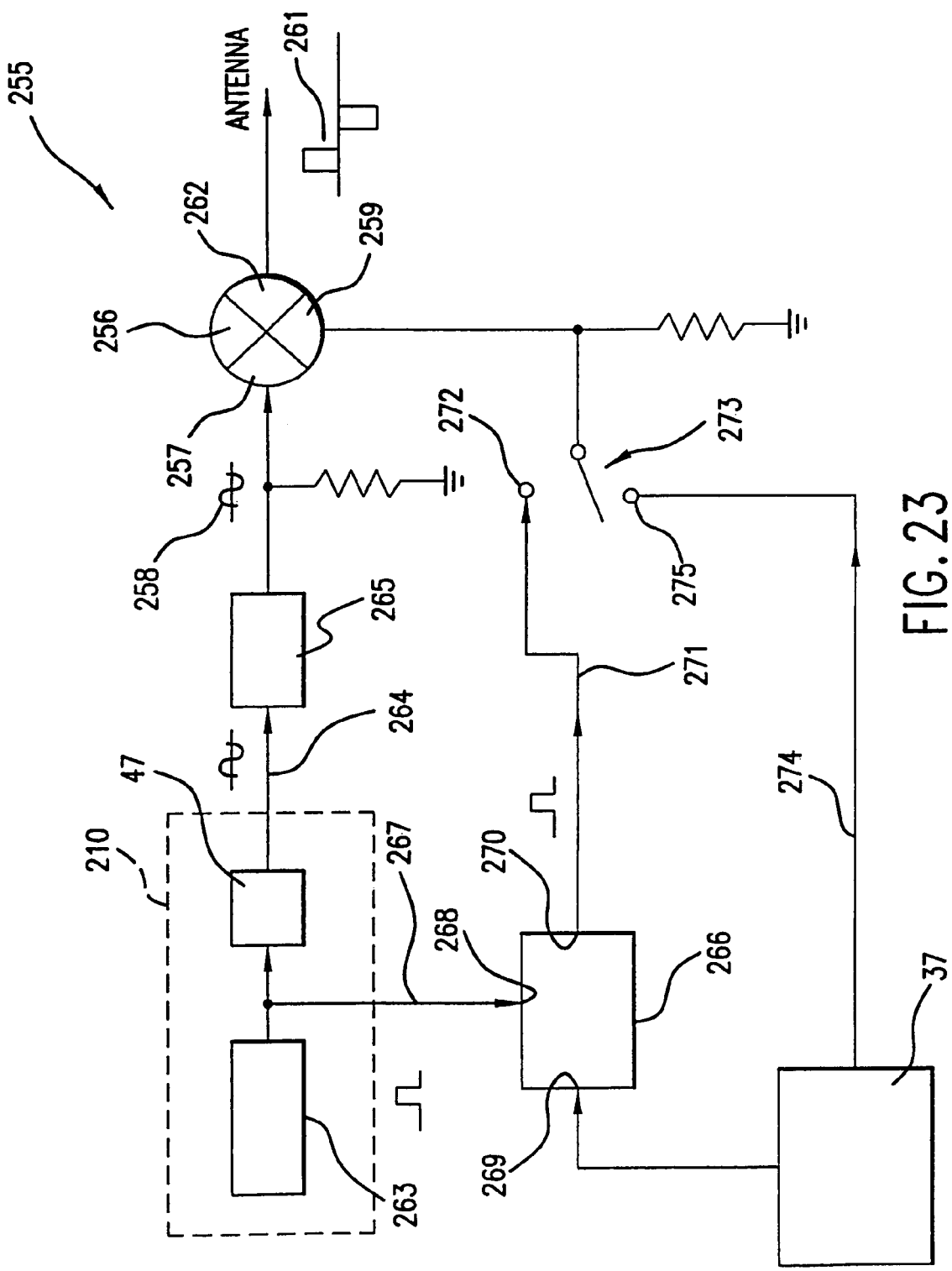
FIG. 23 is a more comprehensive block diagram of the combined analog and digital techniques for modulation of the carrier signal; and, FIG. 24 shows an electrical diagram of a balance modulator used in circuits shown in FIGS. 22 and 23.

FIG. 23 shows in comprehensive fashion the transmitter interface unit 255, the principles of operation of which are illustrated in FIG. 22. In FIG. 23, the transmitter interface unit 255 includes the direct digital synthesizer 210 which includes a phase accumulator 263 (which comprises the binary adder 44 and D-type register 45), a look-up table 46, and a digital-to-analog converter (DAC) 47 coupled to the phase accumulator 263 through the channel 264. A low pass filter 265 is connected to the output of the DAC 47. The carrier signal generated by the direct digital synthesizer 210 is output in analog form to the low pass filter 265 (serving to cut off the undesirable high frequencies) and is supplied to the input 259 of the balance modulator 256.

A digital comparator 266 is coupled through the communication channel 267 to the output of the phase accumulator 263 in order that the carrier signal in digital form generated at the direct digital synthesizer 210 is coupled to the input 268 of the digital comparator 266. Similar to the drive unit 230 shown in FIG. 21, a reference signal, i.e., digital code representing the pulse width set point, is supplied to the input 269 of the digital comparator 266 from the control interface circuitry 37.

Once a match is found between the reference digital code and the digital carrier signal, the digital comparator 266 outputs the gating digital pulse which further passes from the output 270 of the digital comparator 266 through the communication channel 271 to the terminal 272 of the switch 273. When the switch 273 couples the output of the digital comparator 266 to the input 259 of the balance modulator 256, the carrier signal is modulated in accordance with the width of the modulating pulse for driving the antenna in an ON/OFF fashion.

Simultaneously, the control interface circuitry 37 through the communication channel 274 supplies a modulation signal of different nature (for example, for amplitude, phase, and/or frequency modulation) to the terminal 275 of the switch 273. In this manner when the switch 273 couples the control interface circuitry 37 to the input 259 of the balance modulator 256, the carrier signal 258 is modulated within the balance modulator 256 in accordance with the modulation parameters supplied from the control interface circuitry 37. The modulated signal 261 is output at the output 262 of the balance modulator 256 and is supplied to the antenna 27. It is clear to those skilled in the art, that in the transmitter interface unit 255, shown in FIG. 23, a flexible and versatile modulation technique is presented allowing for control over the modulated output with a reduced number of distortion components and improved load matching.

The balanced modulator circuitry provides controlled modulation of signal envelope amplitude and/or waveshape. This function may be accomplished by a variety of means. For example, an analogous balanced modulator 256, shown in FIG. 24, is the model MC 1496, commercially available from Motorola, Inc., Schaumburg, Ill. 60196.

Figure 24:
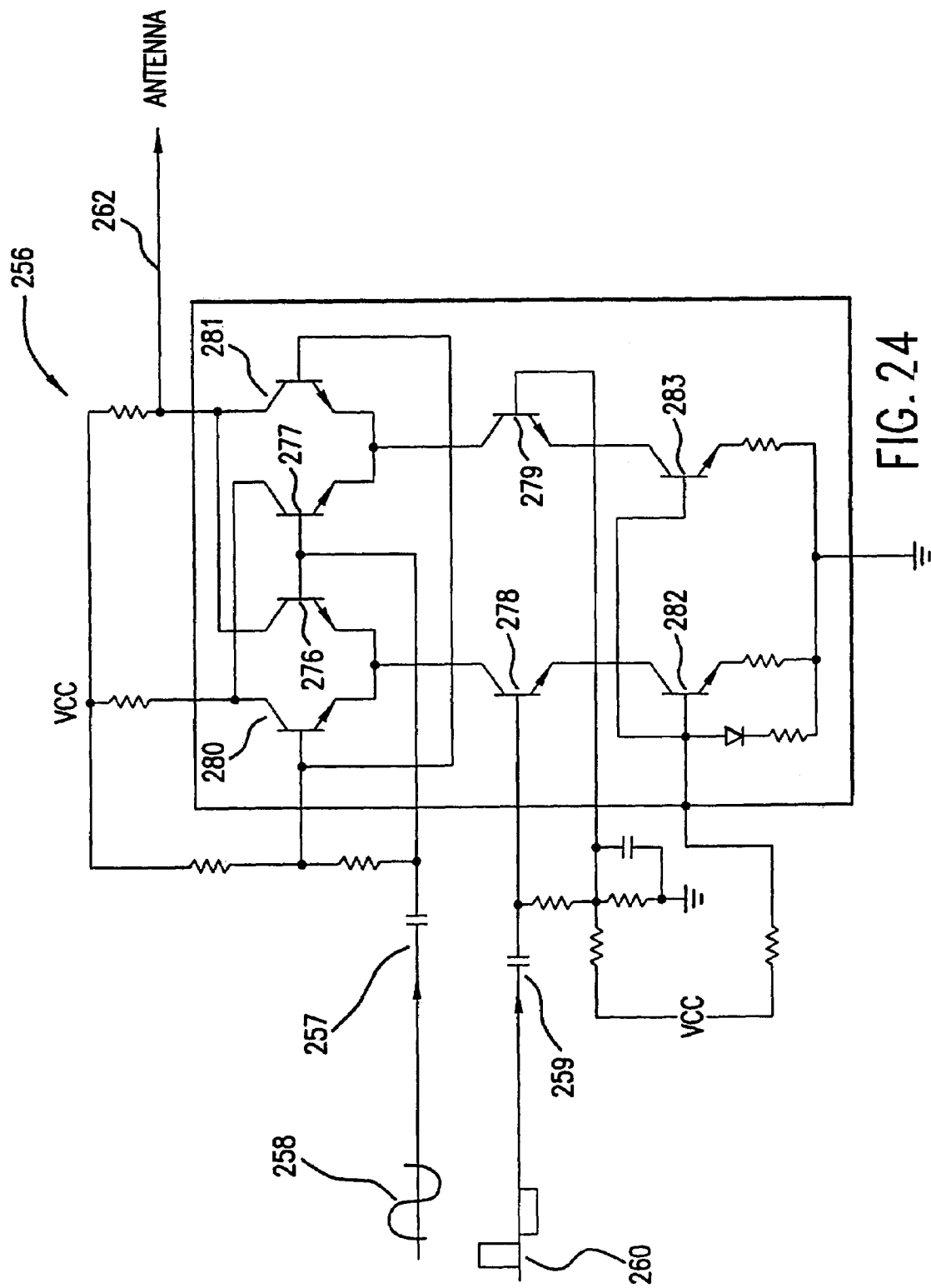

As shown in FIG. 24, the balanced modulator 256 includes transistors 276-283, and further has the input 257 through which the carrier signal 258 is coupled to the bases of the transistors 276 and 277. The modulation signal 260 is input into the port 259 of the balanced modulator 256 and is coupled to the base of the transistor 278.

Another important novel feature of the present invention is that the transmitter interface unit 26 is integrally built into the patient interactive computer 25 or the antenna 27, thus avoiding use of cable between various components of the system resulting in minimizing cable breakage potential.

Additionally, the pentop patient interactive computer 25 and its interface may be battery powered, thereby eliminating leakage passes and short circuit to ground.

As discussed above and as shown in FIGS. 3 and 4, the patient interactive computer 25 has a display 30 for displaying screen graphics and screen worded messages corresponding to the screen graphics for communicating with the patient. The touch screen of the display 30 also serves for receiving feedback from the patient in response to the worded screen messages by means of the stylus 31 or other means known to those skilled in the art.

The screen worded messages displayed on the display 30 along with the screen graphics describe to the patient an action expected from the patient to operate the stylus 31 for entry of the patient's response, which is considered by the patient interactive computer 25 as data to be further processed.

Since the screen graphics and screen worded messages requesting a certain action of the patient are displayed simultaneously on the same display 30, the system avoids hand-eye coordination problems found in the prior art neurostimulation systems. Intuitive operation with drawings made by the patient directly on the computer display 30 makes data collection easier and faster.

It is known to those skilled in the art, that each patient needs a distinguishing pattern of neurostimulation according to his/her health problem, body constitution, and level of body response to neurostimulation. Therefore, the parameters of neurostimulation must be adjusted to each particular patient before the treatment is initiated. To adjust the neurostimulation pattern, the system of the present invention allows a list of optimization protocols which are stored in the physician's desktop computer 34. Each optimization protocol consists of either predetermined or algorithmic operations, which allow collecting specific data needed for further analysis and optimization of the stimulation setting for each particular patient.

The physician selects a particular one of the optimization protocols either on the computer 25 or the physician's computer 34 (which is optional in the system), transmits the data corresponding to the selected protocol to the patient interactive computer 25 which initiates the process of interaction between the patient and the patient interactive computer 25. When the selected protocol is accomplished and all data are entered by the patient requested by the optimization protocol, the physician selects another optimization protocol, unless all necessary optimization protocols are completed. When the procedure is fulfilled, the data collected during each optimization protocol are processed, and the optimal parameters for the neurostimulation treatment are determined. These parameters constitute the optimized pattern of neurostimulation for the particular patient, his/her health problem, and body reaction to the neurostimulation for the most effective pain relief. Such optimal choices are presented for clinician review. The clinician may evaluate and re-sort, by "situationally preferred parameters" to select a prescription for treatment.

The optimization protocols are created from, but are not limited to, the following "building blocks" some of which are combined in a predetermined group for each particular protocol:

patient controlled amplitude adjustment procedure that allows the patient to adjust stimulation levels to meet a requested, medically significant criteria (amplitude threshold);

stimulus rating and pain region and the procedure in which significant regions are marked by the patient using a body-region;

patient rating procedure in which the degree of pain, degree of stimulation relief, or other rating is determined on a numeric scale;

a pause between setting changes to allow stimulation sensations to fade before presenting new settings;

multiple threshold determination in which different thresholds at identical settings are tested in expected order.

According to each particular optimization protocol, a relevant screen graphics and screen worded messages appear on the display 30. A stimulus rating and pain region allow the patient to enter a map of pain or paresthesia areas by drawing their sensation regions on a body image displayed on the screen of the display 30.

Figure 7A:
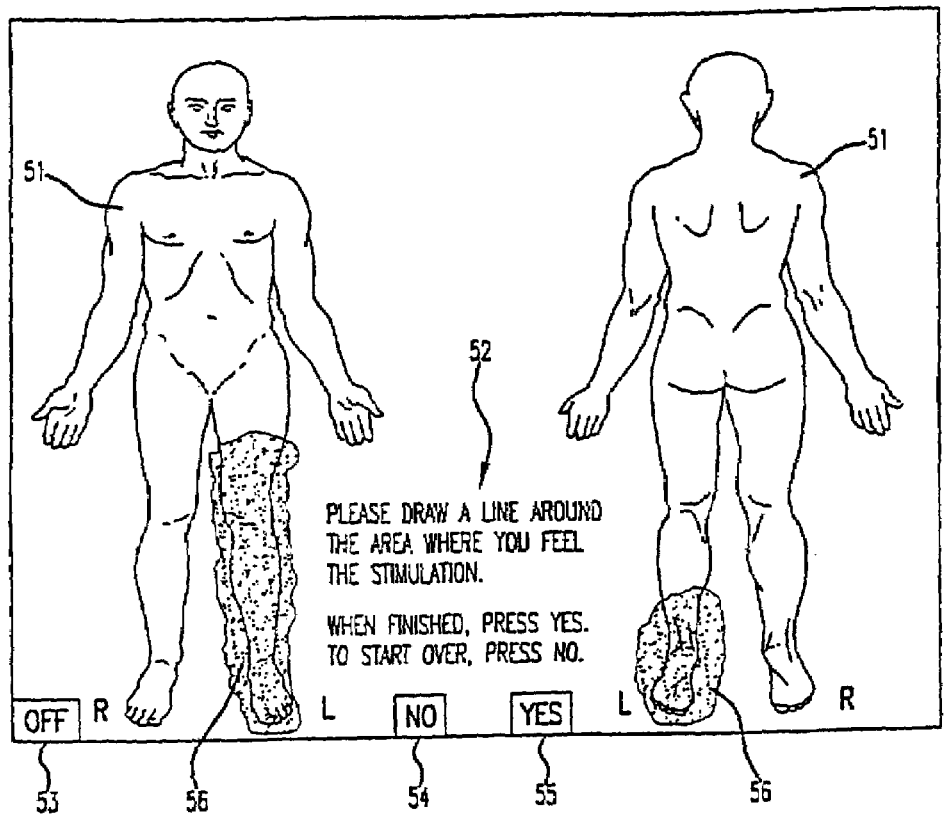
FIGS. 7A and 7B show body drawing screens, with the screen shown in FIG. 7B displaying the prototype neurostimulation system, and the screen shown in FIG. 7B is built using a Windows style control and text preferred for a commercial version.
Figure 7B:
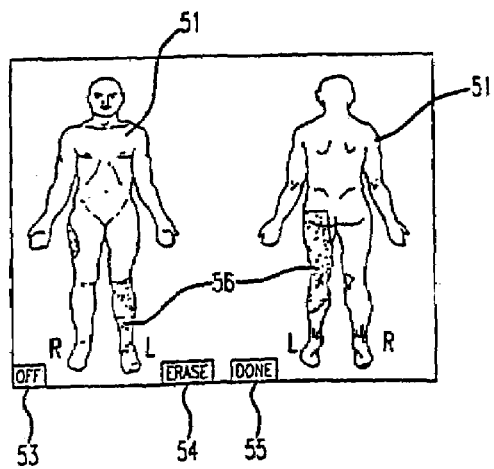

As shown in FIGS. 7A and 7B (with FIG. 7A drawn from NSS, while FIG. 7B shows a similar screen built using the Windows style controls and text preferred for a commercial version, front and back body images 51 allow the patient to draw regions of pain experienced or of paresthesia using a natural, body-based frame as a reference. The screen, shown in FIGS. 7A and 7B, is used for collecting patient pain maps during pain mapping and for collecting paresthesia mapping during stimulation testing. The screen message 52 in FIG. 7A, describes briefly what is expected of the patient. For example, for entering a map of pain experienced, the message 52 is worded as "Please draw a line around the area where you feel pain." In response to this message, the patient, by means of the stylus 31, outlines the area of pain experienced 56 on the area of the body image 51. When the outline is completed, the patient presses "Yes" to indicate the patient has completed the task or presses "No" to start over.

During stimulation, the patient may be requested to draw a line around the area where he/she feels the stimulation. The process is the same as discussed above for entry data for areas of pain experienced.

The "Off" button 53, readable only during stimulation testing, immediately turns stimulation off, and sends the patient back to the amplitude adjustment screen (to be discussed in further paragraphs) to reset amplitude levels.

No/erase button 54 allows the patient to erase the map and start over.

Yes/done button 55 allows the patient to respond positively to the displayed message signifying they have completed the map.

Figure 8B:
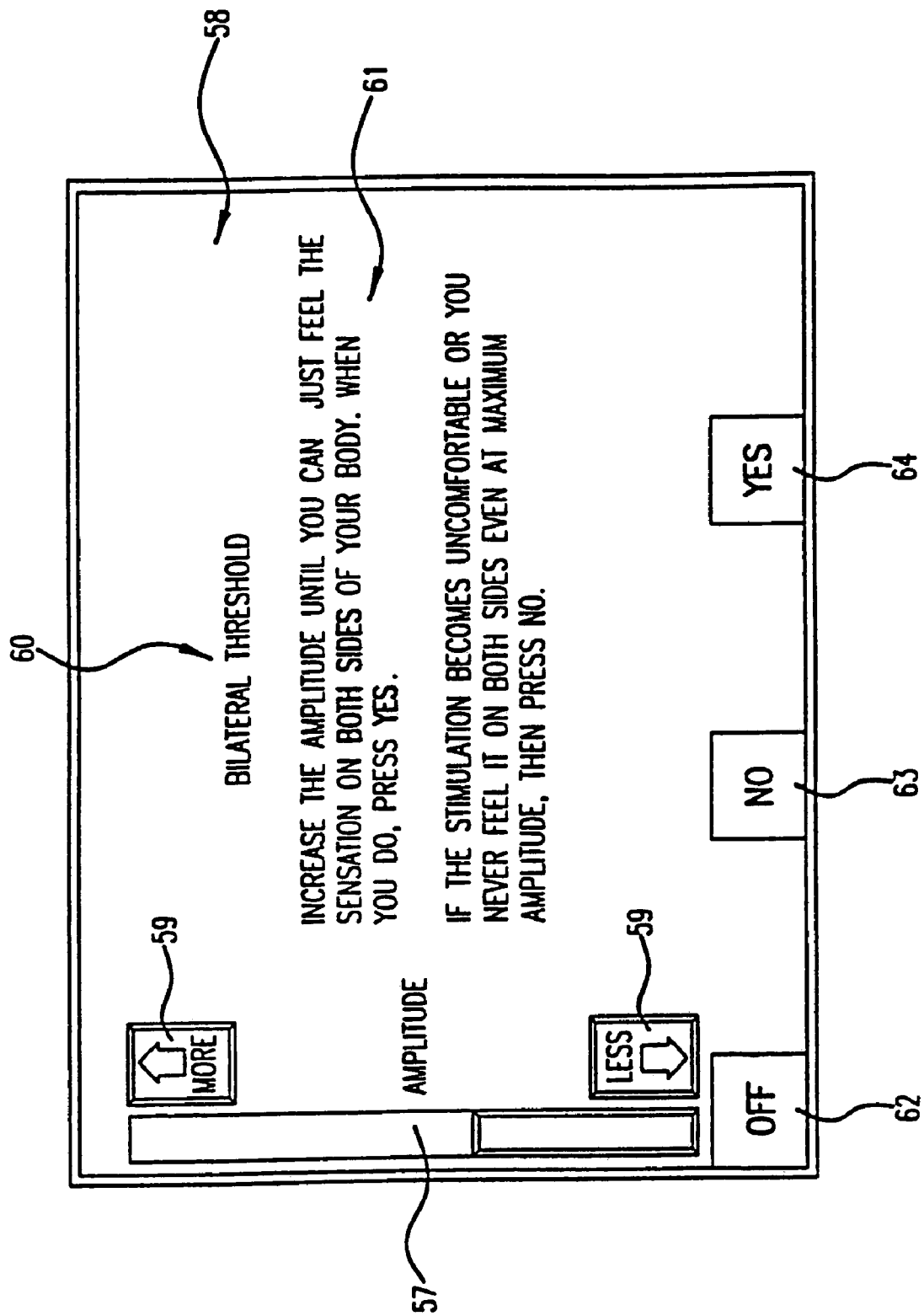

FIGS. 8A and 8B show the amplitude adjustment screen appearing on the display 30 when a patient controlled amplitude adjustment procedure protocol is run on the computer. The amplitude adjustment procedure allows the patient to adjust stimulation amplitude to meet stated criteria for each threshold.

The screen shown in FIG. 8A is drawn from NSS, while the screen shown in FIG. 8B shows a similar screen built using the Windows style controls and text generally preferred for commercial applications. An amplitude adjustment bar 57 of the amplitude adjustment screen 58 shows graphically the relative amplitude level, which the implanted device is currently generating, and allows the patient to adjust the amplitude in real time by pulling the bar up or down, by touching below or above the bar, or by using the "More" or "Less" arrow buttons. The "More" or "Less" arrow buttons 59 allow the patient to increment or decrement the amplitude in small steps. A threshold label 60 shows the name of a threshold being tested for quick reference by an observing clinician and as a shorthand memory jog for patients as they become familiar with testing.

A threshold message 61 displays a carefully worded message describing, for each particular threshold what the patient needs to accomplish by adjusting the amplitude bar 57. The "Off" button 62 immediately turns the stimulation off.

"No" button 63 allows the patient to respond under certain conditions when they are unable to satisfy the requested threshold criteria. This button is visible only when it is pertinent to the threshold message. "Yes" button 64 allows the patient to respond positively to the displayed message, signifying they have completed adjusting the amplitude to meet the stated criteria.

The amplitude adjustment bar 57 shown in FIGS. 8A and 8B, may be displayed as a vertical thermometer style graphic bar outline, which is partially filled to indicate the current parameter level, and which can be adjusted by moving the stylus 31 over the thermometer style bracket bar outline, in three modes: (1) by placing the stylus at the position of the edge of the filled portion, the level of the parameter may be moved freely up and down by the patient, provided it is not adjusted faster than a preset safe maximum rate of movement; (2) by placing the stylus at a position in the bar outline 57 away from the filled/unfilled edge, the level of the parameter will move toward the stylus position at a predetermined safe rate, typically asymmetrical so that the level may be decreased rapidly but increased only slowly; and, (3) by using external controls such as "Up" or "Down" arrows, "Off" button, etc., the level of the parameter may be changed at a predetermined rate, in small increments, turned off, or set to a predetermined level instantly.

Once the patient is satisfied that he/she met the criteria of a certain threshold, the patient hits the "Yes" button 64 and moves to the next screen which displace body overlays 51, as shown in FIGS. 7A and 7B. At this stage, the patient is requested to outline the area of the stimulation-coverage 56, as opposed to the pain experienced. When the patient is satisfied that he/she has completed this procedure, he/she hits "Yes" button 55 to continue. The computer 25 then goes through a confirmatory process by displaying the message, meaning "is this what you meant?". When the patient answers "yes", the computer 25 displays the subjective screen 65, shown in FIGS. 9A and 9B. The software adapts to the patient and offers the option of discontinuing the confirmation screen if responses are sufficiently consistent.

Figure 9A:
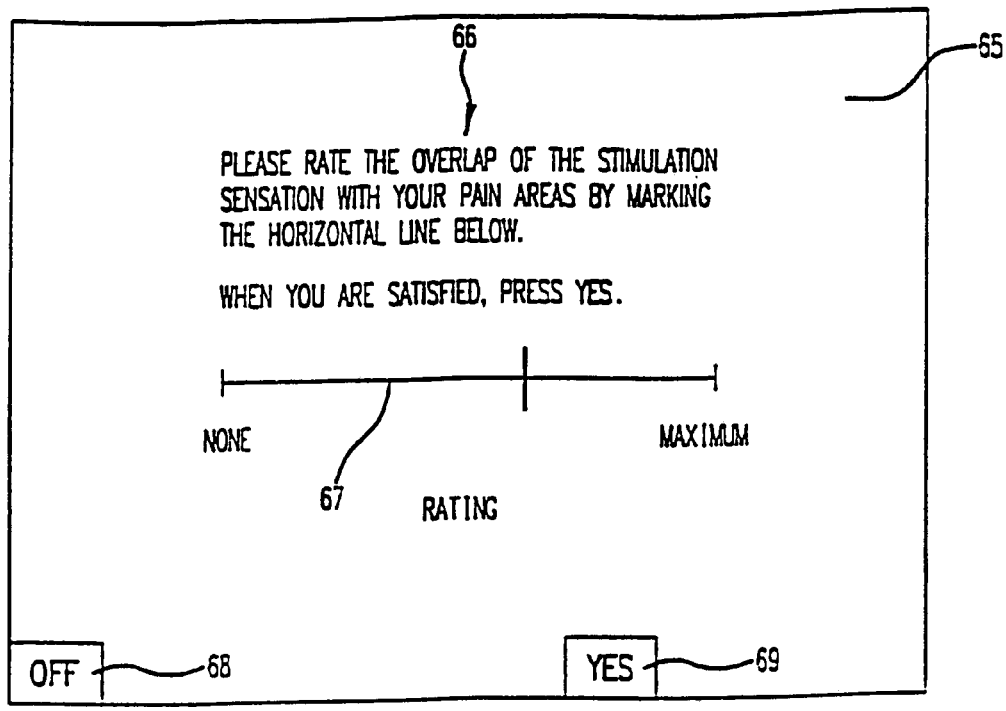
FIGS. 9A and 9B illustrate a subjective rating screen, with the screen shown in FIG. 9A drawn from prototype neurostimulation system (NSS), while the screen shown in FIG. 9B built using the Windows style controls and text preferred for a commercial version.
Figure 9B:
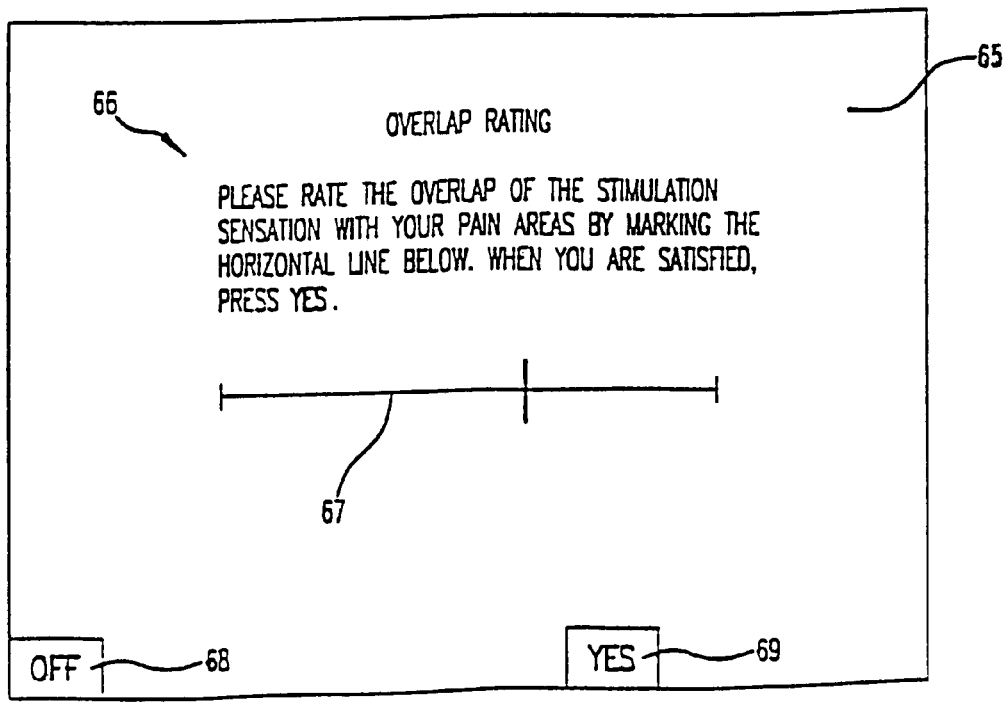

Subjective rating screen, shown in FIGS. 9A and 9B, allows the patient to enter a subjective rating of degree of pain during pain mapping and of overlap of pain by paresthesia during stimulation testing. The subjective rating screen 65, shown in FIG. 9A is drawn from NSS, while the subjective rating screen 65 shown in FIG. 9B is built using the Windows style controls and text preferred for commercial applications. The screen message 66 on rating screen 65 describes briefly what is expected of the patient.

An analog rating bar 67 allows the patient to indicate degree of pain or of overlap of pain by paresthesia by marking a vertical line on a horizontal bar. The patient may move the mark after its initial placement until the patient is satisfied with the region.

"Off" button 68, visible only during stimulation testing, immediately turns stimulation to the "off" mode and sends the patient back to the amplitude adjustment screen to reset the amplitude level. "Yes" button 69 allows the patient to respond positively to the displayed message, signifying they are satisfied with the entered region.

The subjective rating screen 65 allows the user to rate the level of relief from the pain by electrostimulation. After the step of subjective rating has been completed, the patient hits the "Yes" button 69 to continue, and the patient interactive computer 25 displays on the display 30, a stimulation clear screen (or message screen) 70, shown in FIGS. 10A and 10B. The stimulation clear screen 70 informs the patient and waits for his/her response. This screen is basically used to permit the patient a rest break between stimulation settings.

Figure 10A:
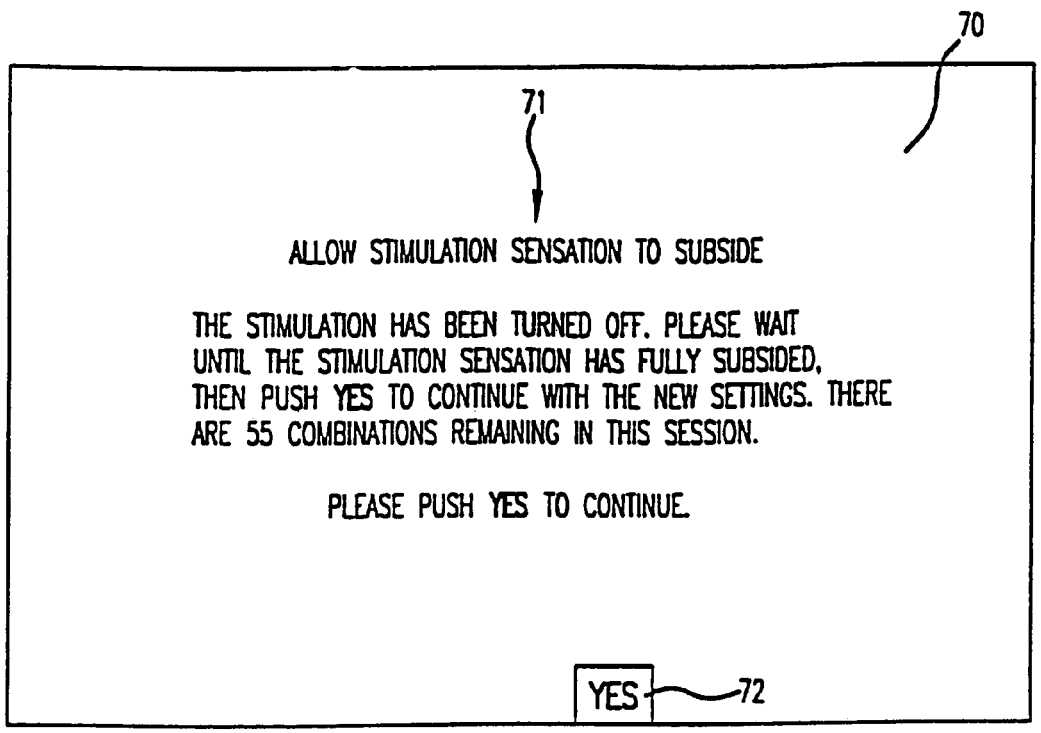
FIGS. 10A and 10B illustrate a message screen, with the screen shown in FIG. 10A drawn from prototype NSS while the screen shown in FIG. 10B is built using the Windows style controls and text preferred for a commercial version.
Figure 10B:
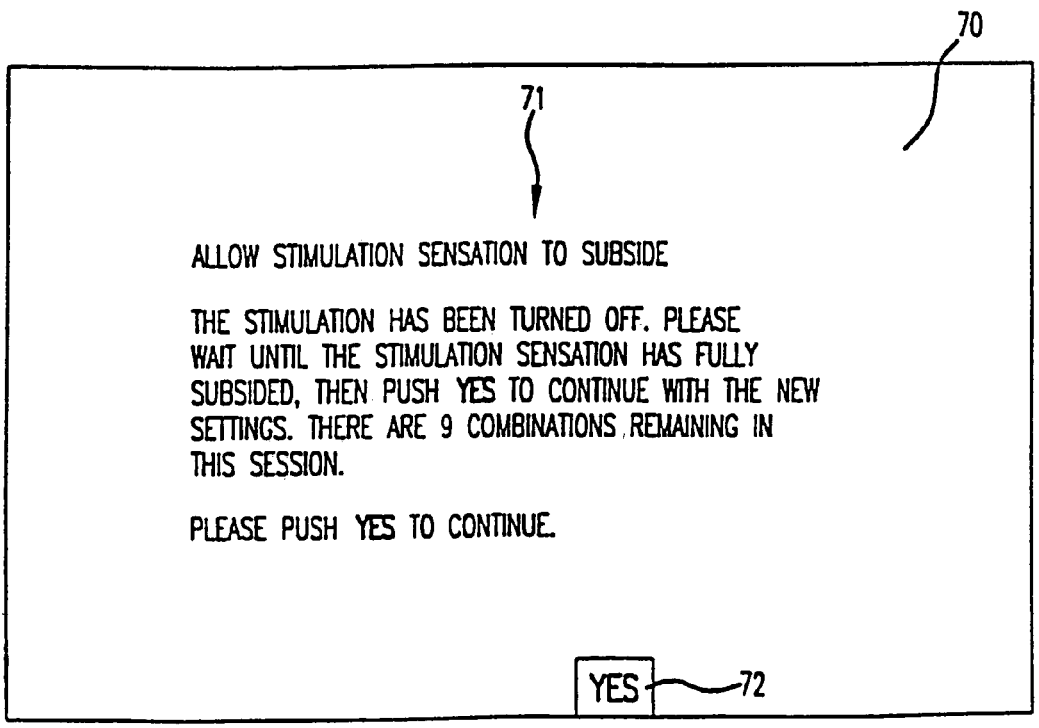

The screen shown in FIG. 10A is drawn from NSS, while the screen shown in FIG. 10B shows a similar screen built using the Windows style control and text preferred for commercial applications.

The screen message 71 describes a situation or what action is expected of the patient. It is also used to inform the patient of inconsistent data entries or other conditions that only require an acknowledgement before continuing. "Off" button, not shown, visible only during active stimulation, turns the stimulation off, and sends the patient back to the amplitude adjustment screen to reset amplitude levels. The "Yes" button 72 allows the patient to respond positively to the displayed message, signifying that the patient has read it and met the criteria or otherwise understands the situation.

Figure 11:
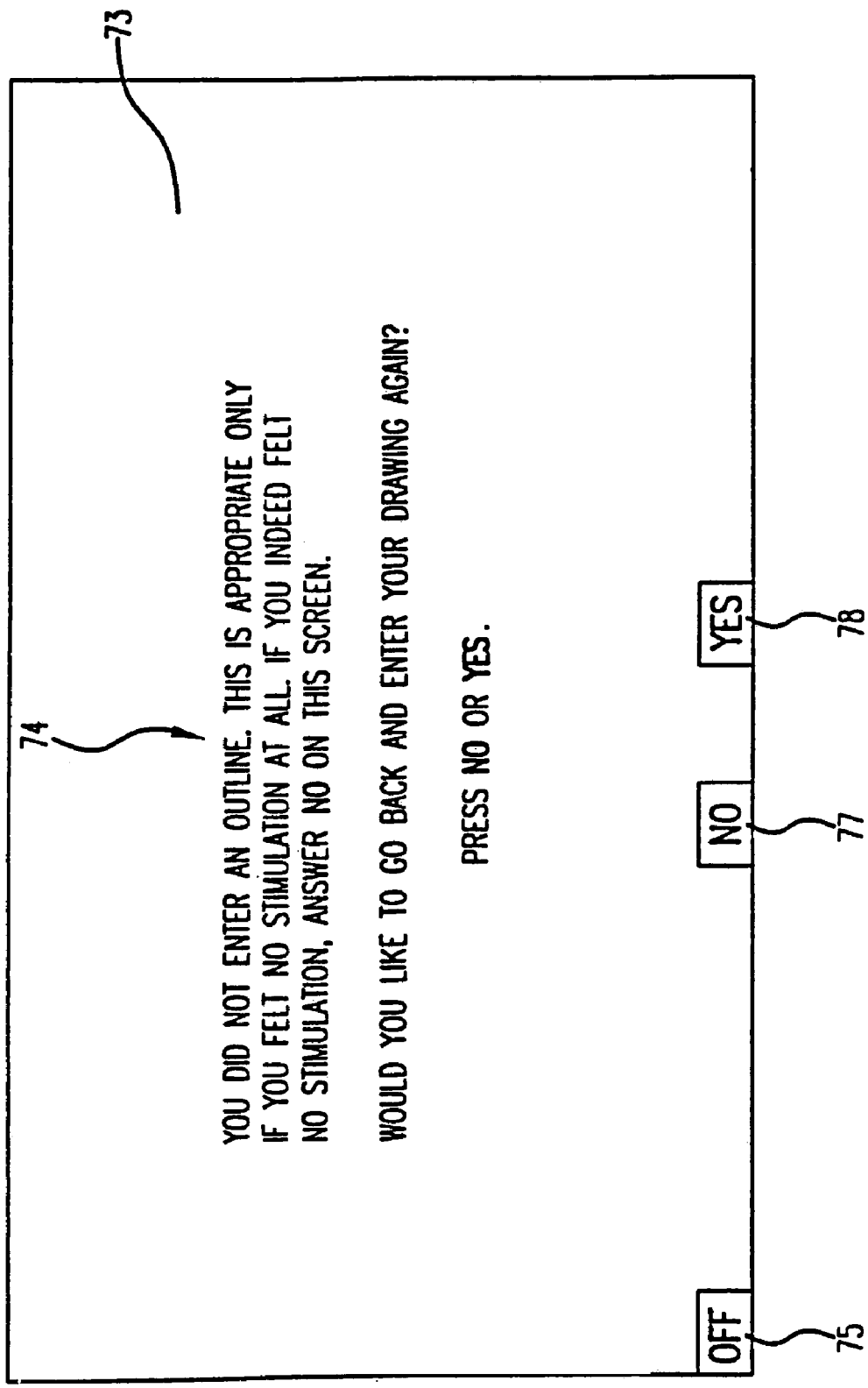
FIG. 11 illustrates a question screen drawn from NSS.

The question screen 73 shown in FIG. 11, informs or queries the patient and waits for response. The screen is used under any conditions that require a clarification or multiple choice response from the patient. It is used, for example, to inform the patient of an inconsistent data entry. The screen 73 is drawn from NSS and may be replaced by a screen using Windows style control and text in the commercial version.

The screen message 74 describes a situation or what is expected of patient, and a stated question that may be answered with a "Yes" or "No" response. The "Off" button 75 turns the stimulation off, and sends the patient back to the amplitude adjustment screen to reset amplitude levels. The "Off" button 75 is visible only during active stimulation. "No" button 76 allows the patient to respond negatively to the displayed message and continue with testing. "Yes" button 77 allows the patient to respond positively to the displayed message and continue with the testing.

A typical session corresponding to an optimization protocol chosen by the clinician from the available menu of the optimization protocol involves repeated cycles through the following steps: (1) computer automatically sets implant stimulation parameters; (2) patient adjusts amplitude to meet one or more predefined criteria threshold; (3) patient draws area of stimulation coverage on a body outline; (4) patient rates effectiveness of the setting on a 100 mm scale; (5) computer turns off stimulation and waits for stimulation sensation to clear; (6) process proceeds again with a new stimulation setting until the session is finished.

After data has been collected, the analysis stage is initiated. Data collected for each stimulation setting is compared against data for other settings and against the previously entered pain drawing. A list of best settings is produced, sorted in rank order by physician chosen criteria. The best setting may be pre-entered in report format or they may be programmed automatically into an advanced patient stimulation as. "presets".

As discussed above, the system of the present invention allows the determination of multiple thresholds including perceptual—the lowest detectable level of sensation; usage threshold—the preferred level of pain relief; bilateral—the lowest level of the lateral body stimulation; area of interest threshold—the lowest level to cover a specific target body area; motor threshold—the lowest level at which involuntary muscle twitching occurs; and discomfort threshold—the level at which stimulation becomes uncomfortable.

In order to define any of the above thresholds entered into the system by the patient, a method of limits may be used which is the verification of threshold which comprises an algorithm in which the amplitude of stimulation is varied systematically above and below an initial threshold estimate while asking the patient to verify the presence or absence of the threshold criteria in order to check for consistency of the threshold level.

With respect again to FIGS. 7A and 7B, the system of the present invention allows the patient use of the stylus to enter location information by motion relative to a body drawing by outlining the region or by coloring the region on the screen.

The system of the present invention provides a multi-level body region location wherein regions of different pain severity, stimulation level, or other measures are entered sequentially using the body region entry procedure, while the region previously drawn (at other levels) is displayed for reference. The comparison of the previously entered and successively entered information is further used for optimization of stimulation settings for the patient.

The system of the present invention allows for confirmation of body regions entered in which body regions are redisplayed as filled polygons over the body drawing where the polygons are consistent with the program's interpretation of the entered regions. The patient is asked "is this what you meant?" with an opportunity to re-enter the drawing should the display not appear as desired.

In order that sensations from the previous stimulation session not influence the perception of the next stimulation session, the system allows a patient a predetermined pause time between stimulation sessions in order that previous sensations will have faded before continuing with the next setting.

For the determination of the multiple thresholds, the system goes through the predetermined procedure and determines the multiple thresholds in the increasing order using the assumption that all thresholds go in a natural order, i.e., they tend to be higher than perceptual, for example, but below the discomfort which is the stage at which the patient cannot tolerate the stimulation and lowers the stimulation level.

By leaving the perceptual threshold as the minimal threshold, the patient begins from the perceptual amplitude by adjusting such on the adjustment screen shown in FIGS. 8A and 8B. Briefly, the sequential testing of medically significant amplitude thresholds at similar settings are met with stimulation held at the last patient set amplitude until readjusted. If the next threshold in sequence may be below the current one, then the next threshold at perceptual or lowest possible threshold is begun. After meeting the discomfort amplitude threshold, the patient may decrease amplitude to a more comfortable setting for meeting the requested medical criteria.

The system of the present invention allows provision of "absurdity checks" when the patient inputs data that is not consistent. The system then requests the patient to redo any threshold setting that is not consistent with reasonable expectations, including:
  (1) any threshold recorded as less than the perceptual amplitude;
  (2) stimulation region entered while amplitude is at zero;
  (3) no stimulation felt but amplitude is less than maximum;
  (4) specific criteria requested but not met, e.g., the bilateral threshold requested, but a non bi-lateral stimulation region entered, and amplitude less than maximum;
  (5) emergency off button used.

When entry of particular data is not consistent with reasonable expectations, the system requests re-entry of stimulation of this data, for example, where stimulation body regions are drawn, the re-entry is requested when:
  the entry of points is exclusively outside of the body interior,
  entry of non-bilateral drawing is for a bilateral threshold;
  entry of "no" points is followed by entry of a rating indicating that stimulation must be present.

The collected data is analyzed after collection of data entered by the patient in response to the requests displayed on the screen of the patient interactive computer 25 during the cyclically established protocol. The analysis includes a comparison between two body region entries by examining the overlap of filled polygon regions with each other but restricted to the body drawing interior, and determining proportions of overlapping and extraneous pixels.

The regions entered as outlined are treated as filled polygon regions, and this approach is used to compare different areas, such as comparison of stimulation with pain regions, comparison of stimulation with target areas of interest, comparison of stimulation to other stimulation, pain map to pain map, or any other collected drawings.

In the course of the analysis, the system sorts and displays stimulation settings in rank order by:
  order of presentation;
  threshold amplitude value;
  scale threshold amplitude value on the range from perceptual to discomfort;
  patient rating of pain relief at a chosen threshold; and
  overlap or extraneous pixel proportions as determined by analysis method.

In each protocol, the computer 25 goes through a pre-set or algorithmic procedure under the direction of the physician in order to find an optimal setting. This procedure for finding an optimal setting may include the following optimization protocols:
  (a) presentation of a sequence of stimulation settings under computer control for determination of various amplitude thresholds, stimulation regions, and patient ratings;
  (b) presentation as in the protocol (a) from a fixed list in either randomized or fixed order;
  (c) presentation as in the protocol (a) using combinations determined interactively by algorithm;
  (d) presentation of a set of electrode combinations in randomized or set order while fixing other stimulation parameters, for determination of various amplitude thresholds, stimulation regions, and patient ratings;
  (e) presentation as in the protocol (d) of a set of electrode combinations for the specific contact sets:
    all valid cathode-anode pairs from the array;
    in an array of N electrodes, all valid cathode/anode sets of size M, where M is less than or equal to N;
    all "guarded" cathode combinations in which a cathode is surrounded on two sides by anodes (the guarded cathode combination or the split anodes may give more focused stimulation for the neurostimulation treatment);
  (f) "Retest Best Settings". The system takes the optimal set from a previously completed session and retests that optimal set. Presentation is run as in the protocol (d) of a group of settings ranked as "best" by selected criteria in an analysis of a previous test session;

(g) "Bilateral optimization"—adjustment of stimulation sensations laterally (left-right) is run by adding or subtracting active electrode contact position from one of two arrays placed on either side of the spinal mid-line.

(h) "Paired Stimulation"—adjustment of stimulation sensations is run by changing the phase relationship between current pulses at two or more fixed stimulation settings.

(i) "Arbitrary pattern stimulation"—the stimulation with an arbitrary sequence of current pulses at various settings.

The list of best or optimal settings is produced which is sorted in rank order by physician chosen criteria. The best settings may be printed in report format, or they may be programmed automatically into an advanced patient stimulator as "presets".

The collected data may be transferred between NSS work stations and may be re-analyzed or used as the basis for further patient testing on other work stations. Alternatively, the data may be stored in a common data base. Patient data and implant information in all cases may be transferred to remote data servers.

The NSS system uses special messages to indicate certain conditions of note to the patient. In most cases, the listed conditions are generated by an inconsistency in patient data entry, such cross-checks are known collectively as "absurdity checks". Additional alerts are used for time saving measures, emergency "off" actions, and a few other conditions. Each condition has an associated audio cue to aid the patient in recognizing quickly that they have encountered a screen that doesn't fall within the usual sequence. Standard absurdity checks use a common audio cue labeled the "Bronx Cheer", while more unusual or severe conditions have their own unique sound.

The following conditions message sound an action expected from the patient are contemplated in the system of the present invention for pain map session absurdity check, stimulation session absurdity checks, stimulation session time saving conditions, stimulation session emergency off conditions, other stimulation sessions, alert conditions:

Pain Map Session Absurdity Checks

EXAMPLE 1

| | |
|---|---|
| Condition: | Patient indicated "done" pain drawing but entered no points |
| Message: | You did not enter an outline. Please draw an outline of your body pain areas as requested. Please push YES to continue. |
| Sound: | "Bronx Cheer" sound |
| Action: | Return to pain drawing screen and for another try. |

EXAMPLE 2

| | |
|---|---|
| Condition: | Patient indicated done pain rating but did not mark line. |
| Message: | You did, not enter a pain rating. Please mark the rating line as requested. Please push YES to continue. |
| Sound: | "Bronx Cheer" sound |
| Action: | Return to rating screen and for another try. |

EXAMPLE 3

| | |
|---|---|
| Condition: | Patient completed a dual level pain map but rated overall pain as more severe than worst pain. |
| Message: | You have rated your OVERALL pain as more intense than your WORST pain. Please reconsider and rate each pain intensity again on the following screens. Please push YES to continue. |
| Sound: | "Bronx Cheer" sound |
| Action: | Discard conflicting data. Repeat rating screens for both overall and worst pain. |

EXAMPLE 4

| | |
|---|---|
| Condition: | Patient failed to make a stylus entry within any two minute period. |
| Message: | DID YOU TAKE A BREAK? Over two minutes have elapsed since you last responded to the testing session. Stimulation has been turned off and will not continue until you respond. If you have taken a break, please make sure the antenna is connected before continuing. Please push YES to continue. |
| Action: | Return to drawing screen and begin again. |

Stimulation Session Absurdity Checks

EXAMPLE 5

| | |
|---|---|
| Condition: | Patient entered "Yes" on amplitude screen with amplitude at zero. |
| Message: | You have indicated that you felt stimulation when the stimulator was in fact turned off. The stimulator needs to be running for all the tests. Increase the amplitude as requested or to maximum if you feel nothing, and leave it at that setting for the subsequent testing. Please go back and set the amplitude as requested. Push YES to continue. |
| Sound: | "Bronx Cheer" sound |
| Action: | Return to amplitude screen for same threshold. |

EXAMPLE 6

| | |
|---|---|
| Condition: | Patient entered "Yes" on amplitude screen with amplitude at zero, after having run amplitude up close to maximum |
| Message: | You increased the amplitude to near maximum value, and then turned it off before pushing YES. You have thereby indicated that you felt stimulation when the stimulator was in fact turned off. To record your settings properly, the stimulator needs to be left running for all tests. If you feel nothing at all, then please leave the amplitude set at maximum. Please go back and set the amplitude as requested. Push YES to continue. |
| Sound: | "Bronx Cheers" sound |
| Action: | Return to amplitude screen for same threshold. |

EXAMPLE 7

| | |
|---|---|
| Condition: | Patient adjusted subsequent amplitude threshold below perceptual threshold for same settings (1st occurrence) |
| Message: | The stimulation amplitude for this threshold should be higher than the PERCEPTUAL level (where you could just feel the stimulation). Please raise the amplitude to a level that matches the description on the next screen. Please push YES to continue. |
| Sound: | "Bronx Cheer" sound |
| Action: | Return to amplitude screen for problem threshold. |

EXAMPLE 8

| | |
|---|---|
| Condition: | Patient adjusted subsequent amplitude threshold below perceptual threshold for same settings (2nd occurrence) |
| Message: | The stimulation amplitude for this threshold should be higher than the PERCEPTUAL level (where you could just feel the stimulation). Since you did not raise the amplitude above this level, we will try the PERCEPTUAL level again. Please push YES to continue. |
| Sound: | "Bronx Cheer" sound |
| Action: | Discard data for this setting as inconsistent. Return to amplitude screen for perceptual threshold. |

EXAMPLE 9

| | |
|---|---|
| Condition: | Patient entered a stimulation drawing, but declined to enter rating for same threshold |
| Message: | You have entered an outline indicating stimulated areas, but thereafter indicated you felt nothing by entering no overlap rating. Please consider each area carefully, and try to answer in a consistent manner. If you feel nothing, then enter nothing on the drawing screen. The last test will be repeated. Please push YES to continue. |
| Sound: | "Bronx Cheer" sound |
| Action: | Discard inconsistent threshold data. Return to amplitude screen and begin threshold again. |

EXAMPLE 10

| | |
|---|---|
| Condition: | Patient failed to make a stylus entry within any two minute period. |
| Message: | DID YOU TAKE A BREAK? Over two minutes has elapsed since you last responded to the testing session. Stimulation has been turned off and will not continue until you respond. If you have taken a break, then please make sure the antenna is connected before continuing. ## combinations remain in this session. Please push YES to continue. |
| Sound: | Unique Sound Generation |
| Action: | Amplitude to zero. If mid threshold, discard any incomplete data, return to amplitude screen and begin threshold again. If on wait-for-clear screen, continue with next threshold. If on amplitude screen, resume asking for threshold. |

EXAMPLE 11

| | |
|---|---|
| Condition: | Patient indicated no stimulation was felt but amplitude was less that maximum. (Indicated by entering either no drawing or no rating (in the case where drawing is turned off.)) |
| Message: | The stimulation amplitude is less than maximum. Please increase it until either you feel something or it is at the maximum level. Please push YES to continue. |
| Sound: | "Bronx Cheer" sound |
| Action: | Discard inconsistent threshold data. Return to amplitude screen and begin threshold again. In the case of discomfort or motor thresholds, set amplitude to zero before resuming. |

EXAMPLE 12

| | |
|---|---|
| Condition: | Patient indicated they were unable to obtain discomfort threshold on amplitude screen but did not raise amplitude to maximum. (Indicating by hitting No) |
| Message: | You have indicated that you felt no discomfort, but you did not raise the amplitude to the maximum level. You should raise the amplitude until you feel some discomfort, or to the maximum if you feel no discomfort. Please push YES to continue. |
| Sound: | "Bronx Cheer" sound |
| Action: | Return to amplitude screen, resume discomfort threshold. |

EXAMPLE 13

| | |
|---|---|
| Condition: | Patient entered a non-bilateral drawing for the bilateral threshold. (1st occurrence) |
| Message: | (In conjunction with filled body region display.) Your drawing is not on both sides of the body! Press YES to try again. |
| Sound: | "Bronx Cheer" sound |
| Action: | Discard drawing, return to drawing screen and collect new drawing. |

EXAMPLE 14

| | |
|---|---|
| Condition: | Patient entered a non-bilateral drawing for the bilateral threshold. (After 1st occurrence.) |
| Message: | IS STIMULATION BILATERAL? For this threshold you were asked to increase the amplitude until you felt stimulation on both sides of your body. Your drawing, however, indicates stimulation only on one side. If the amplitude is not adjusted correctly, then push NO. Do you feel stimulation on both sides of your body? Please press NO or YES. |

-continued

| | |
|---|---|
| Sound: | "Bronx Cheer" sound |
| Action: | If YES then discard drawing, return to drawing screen and collect new drawing. If NO then discard threshold data, zero amplitude, return to threshold screen and redo threshold. |

EXAMPLE 15

| | |
|---|---|
| Condition: | Patient indicated done stimulation drawing but entered no points. |
| Message: | You did not enter an outline. This is appropriate only if you felt no stimulation at all. If you indeed felt no stimulation, answer NO on this screen. Would you like to go back and enter your drawing? Please press NO or YES. |
| Sound: | "Bronx Cheer" sound |
| Action: | If NO then record "no stimulation sensation" (subject to other cross checks). If YES then discard missing drawing, return to drawing screen and collect new drawing. |

EXAMPLE 16

| | |
|---|---|
| Condition: | Patient indicated done stimulation rating but did not mark line. |
| Message: | You did not enter a rating. This is appropriate only if you felt no stimulation at all. If indeed you felt no stimulation, answer NO on this screen. Would you like to go back and enter your rating again? Please press NO or YES. |
| Sound: | "Bronx Cheers" sound |
| Action: | If NO then record "no stimulation sensation" (subject to cross checks that no drawing was entered previously). If YES then discard missing rating, return to rating screen and collect new rating. |

Stimulation Session Time Saving Conditions

EXAMPLE 17

| | |
|---|---|
| Condition: | Patient responds "yes" to what-you-meant screen a preset number of consecutive times. |
| Message: | You have consistently confirmed your entered outline as correct. Would you prefer to skip the question "Is this what you meant" after each drawing? Please press NO or YES. |
| Sound: | Unique Sound to this Condition |
| Action: | If YES then discontinue question for remainder of session. If NO then reset counter and ask again after a preset number of times. |

EXAMPLE 18

| | |
|---|---|
| Condition: | Patient entered a perceptual drawing with bilateral body overlap during a session in which bilateral thresholds are being collected. |
| Message: | YOUR PERCEPTUAL DRAWING IS BILATERAL. If you indeed feel stimulation on both sides of your body, please push YES, and we will save time by not asking you for a separate bilateral threshold. If you are not sure that you feel stimulation on both sides of your body then push NO. Do you feel stimulation on both sides of your body? Please press NO or YES. |
| Sound: | Unique Sound for this Condition |
| Action: | If NO then continue normally saving the perceptual drawing. If YES then save the identical threshold, drawing and rating information for bilateral thresholds as well as perceptual and skip collecting a separate bilateral threshold. |

Stimulation Session Emergency Off Conditions

EXAMPLE 19

| | |
|---|---|
| Condition: | Patient used OFF box on any stimulation screen other than amplitude adjustment. |
| Message: | PLEASE SET THE AMPLITUDE AGAIN. Because the emergency OFF function was used during the last test, we must ask you to begin again with setting the amplitude of stimulation. Please push YES to continue. |
| Sound: | None (follows OFF button sound). |
| Action: | Amplitude to zero. Discard threshold data. Return to amplitude screen and begin threshold again. |

EXAMPLE 20

| | |
|---|---|
| Condition: | Patient used physical emergency off switch during stimulation session. |
| Message: | EMERGENCY OFF SWITCH ACTIVATED. The emergency off switch on the stimulation interface unit has been activated. If you wish to continue the stimulation testing, push YES when you are ready. If you are concerned about continuing the session then please call for assistance now. Please push YES when you are ready to continue. |
| Sound: | Repeated alarms beeps |
| Action: | Amplitude to zero. Discard threshold data. Return to amplitude scren and begin threshold again. |

Other Stimulation Session Alert Conditions

EXAMPLE 21

| | |
|---|---|
| Condition: | Uncorrectable problem with system. |
| Message: | TESTING SUSPENDED. Please call for assistance now. |
| Sound: | Unique Sound for this Condition |
| Action: | Discard any partially complete threshold data and end session. Wait for clinician to release the system and confirm abort. |

EXAMPLE 22

| Condition: | Antenna disconnected from transmitter interface. |
|---|---|
| Message: | STIMULATOR ANTENNA NOT CONNECTED! Stimulation has been suspended because there is no antenna connected to the stimulation interface unit. Please connect your antenna to the proper unit and then push YES to restart stimulation. Please push YES when you are ready to continue. |
| Sound: | "Bronx Cheer" sound |
| Action: | Once recovered, discard any partially complete threshold data. Set amplitude to zero. Return to amplitude screen and begin current threshold again. |

EXAMPLE 23

| Condition: | Interface communication error. |
|---|---|
| Message: | PLEASE STAND BY . . . |
| Sound: | "Three short blips" |
| Action: | If communication recovered, discard any partially complete threshold data. Amplitude to zero. Return to amplitude screen and begin current threshold again. If not recovered go to uncorrectable problem screen above. |

EXAMPLE 24

| Condition: | Testing is completed. |
|---|---|
| Message: | TESTING COMPLETED. You have successfully completed the stimulation session. Unless you were otherwise instructed, you may now disconnect yourself from the system. Please wait for assistance before doing any further with the computer. |
| Sound: | "Rising congratulations pattern" sound |
| Action: | If communication recovered, discard any partially complete threshold data. Amplitude to zero. Return to amplitude screen and begin current threshold again. If not recovered go to uncorrectable problem screen above. |

EXAMPLE 24

| Condition: | Testing is completed and automatic post session analysis is set to run. |
|---|---|
| Message: | ANALYSIS STARTING. You have successfully completed the stimulation session. Unless you were otherwise instructed, you may now disconnect yourself from the test system. When you press YES, the computer will analyze the data you have entered and print out a summary of the results. Please push YES now. |
| Sound: | Unique Sound to Indicate Testing Completed |
| Action: | Wait for up to one minute for patient response. Run analysis. Wait for clinician to release the system and confirm return to physician interface. |

Figure 12:
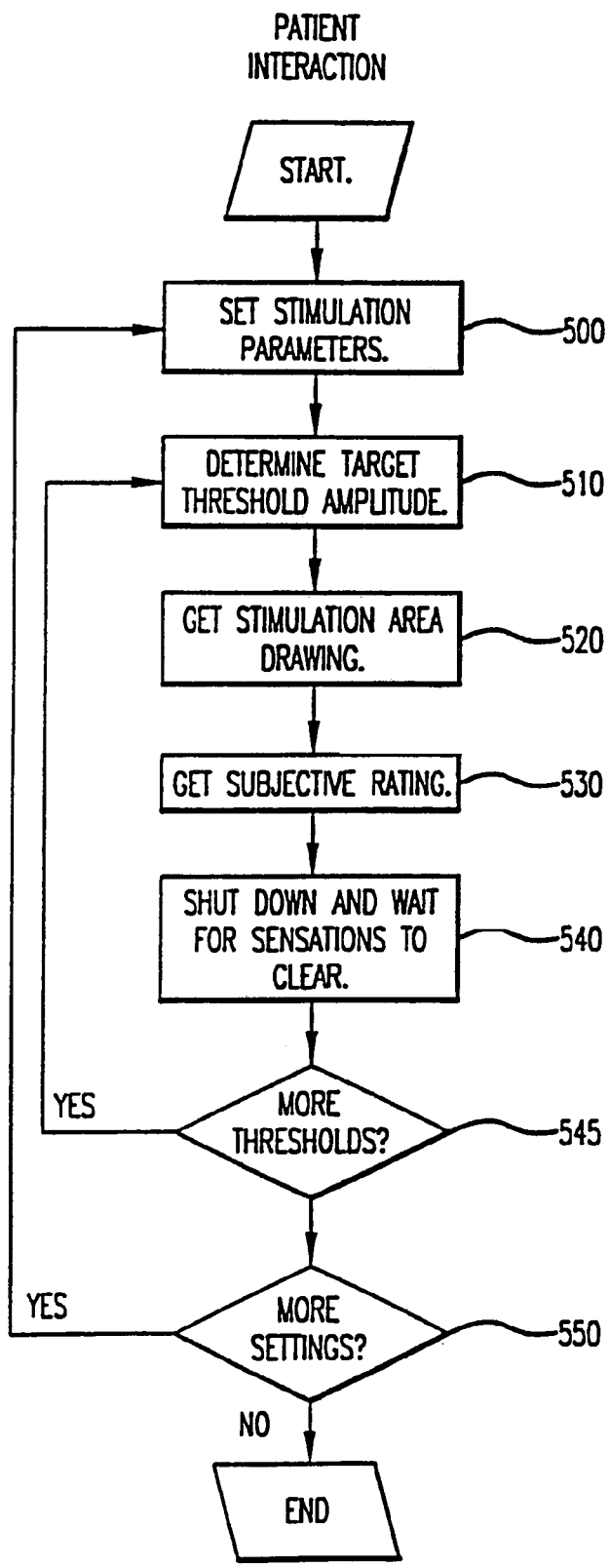
FIG. 12 is a flow chart diagram of a patient interaction procedure.

The flow chart diagram of the patient interaction procedure, shown in FIG. 12, is used to test the various stimulation settings with the patient or with the computer. Flow block 500 sets the stimulation parameters by sending information to the stimulation universal transmitter 26 as described previously. Subsequent to setting the parameters, the system determines a set of threshold amplitudes by going through them sequentially. The first one generally determined is the perceptual threshold, which is the amplitude at which the patient first feels a stimulation.

As discussed above, there are several other thresholds: bilateral threshold, the lowest amplitude at which the patient feels stimulation on both sides of the body; the usage which corresponds to the patient's preferred threshold which relieves the pain, etc. Thus, in block 510, the system provides a stimulus to the patient to determine when the patient begins to feel sensations starting with the lowest possible threshold and amplitude in increasing order, beginning with the perceptual threshold up to the discomfort threshold, as discussed in previous paragraphs. The set of the determined thresholds are then stored in the computer.

The program system then collects a stimulation drawing as shown by the block 520. At this stage, the patient is asked, with the stimulation remaining on at the amplitude the patient set in the previous box 510, to draw or otherwise indicate regions of the body in which they feel the stimulation. The drawing is completed by the patient using the stylus 31 moving over a pair of body images 51, best shown in FIGS. 7A and 7B. Once the patient has entered a drawing recording the stimulation area, the system program enters block 530 to obtain a subjective rating. The patient is asked to indicate the subjective level of relief with the setting of the stimulation parameters at the amplitude they had adjusted, as shown in FIGS. 9A and 9B which is automatically recorded.

All data received from the patient are recorded indicating the regions that were filled, how they were stimulated, and, the subjective rating. At this point, the system shuts down the stimulation and waits for sensations to clear so as not to bias the patient in a subsequent loop which is shown in block 540. It is necessary to make sure that the sensations have completely faded before the next setting is started. The wait period is determined by the patient in response to the request asking the patient to respond when the sensation has cleared.

Flow block 545 asks whether there are more thresholds to be determined. If "yes", the algorithm returns to block 510, if "no", the algorithm enters block 550—"More settings?" As discussed above, the thresholds are tested in natural sequence. Once the set of thresholds that the physician has requested has been completed for a particular setting, the entire procedure is re-entered. If no more settings are to be tested, the patient interaction ends.

FIG. 13 shows the flow chart diagram of the stimulation setting test procedure for determining the particular set of stimulation settings: the target amplitude, the stimulation drawing, the rating, and reporting values. The obtained data is also screened as much as possible for consistency and other features, to make sure that the patient operating on his/her own can generate this data in the best fashion. FIGS. 13A-13D represent an extended flow chart diagram of FIG. 12, showing in more detail what is covered in flow blocks 510-540 of FIG. 12. It is assumed that in FIGS. 13A-13D, stimulation parameters have already been set by operations within flow block 500 of FIG. 12. In block 560, the system sets amplitude to zero. In the block 570, the perceptual threshold is requested. The physician as discussed above has the option of selecting amongst multiple thresholds. The actual testing of thresholds is expanded in FIGS. 14A-14B (to be discussed in detail further). If the perceptual threshold is requested in flow block 570 in FIG. 13A, the system then proceeds according to the threshold test procedure shown in FIGS. 14A-14B.

Figure 13A:
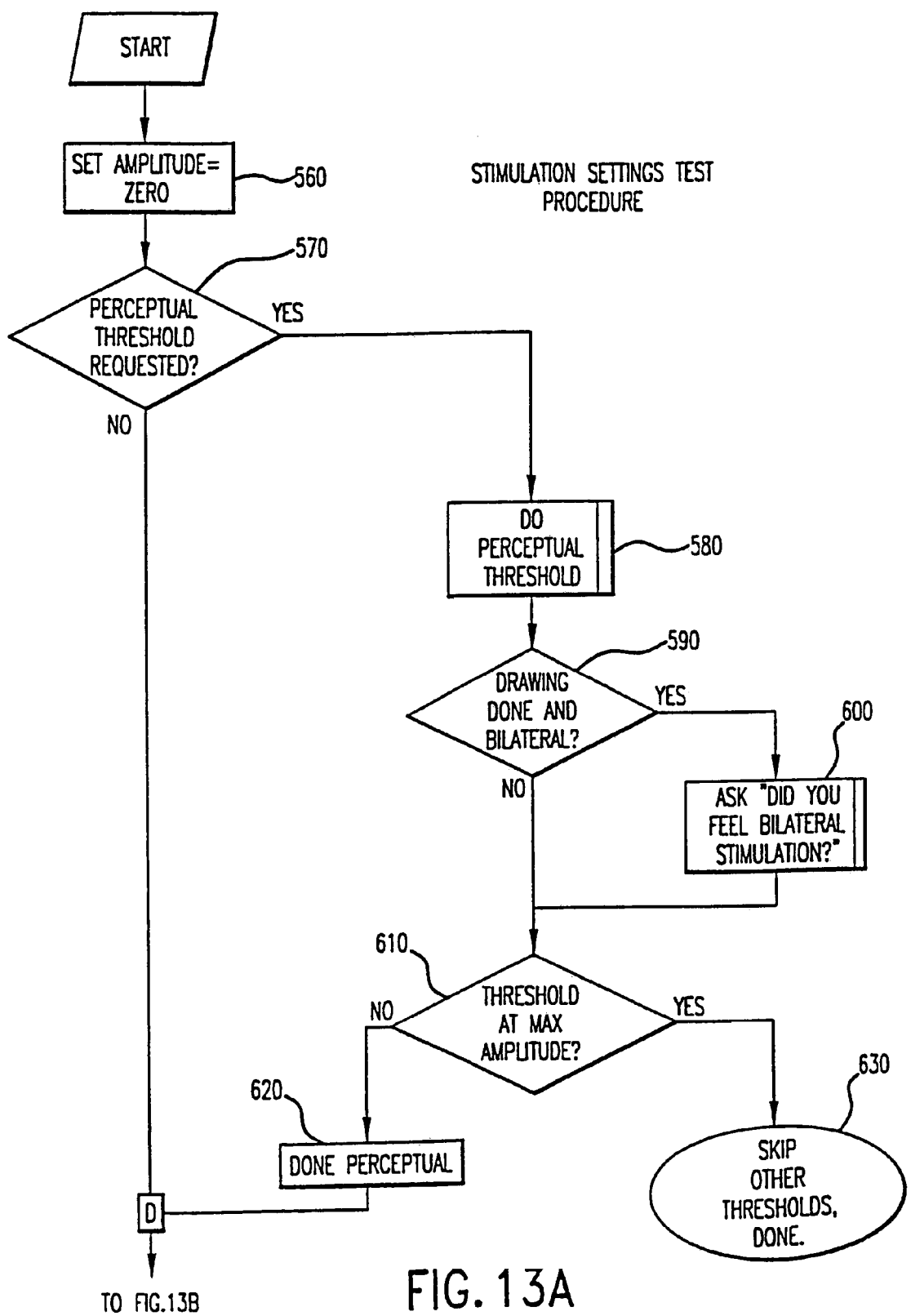
FIGS. 13A-13D represent a flow chart diagram of the stimulation setting test procedure algorithm.
Figure 13B:
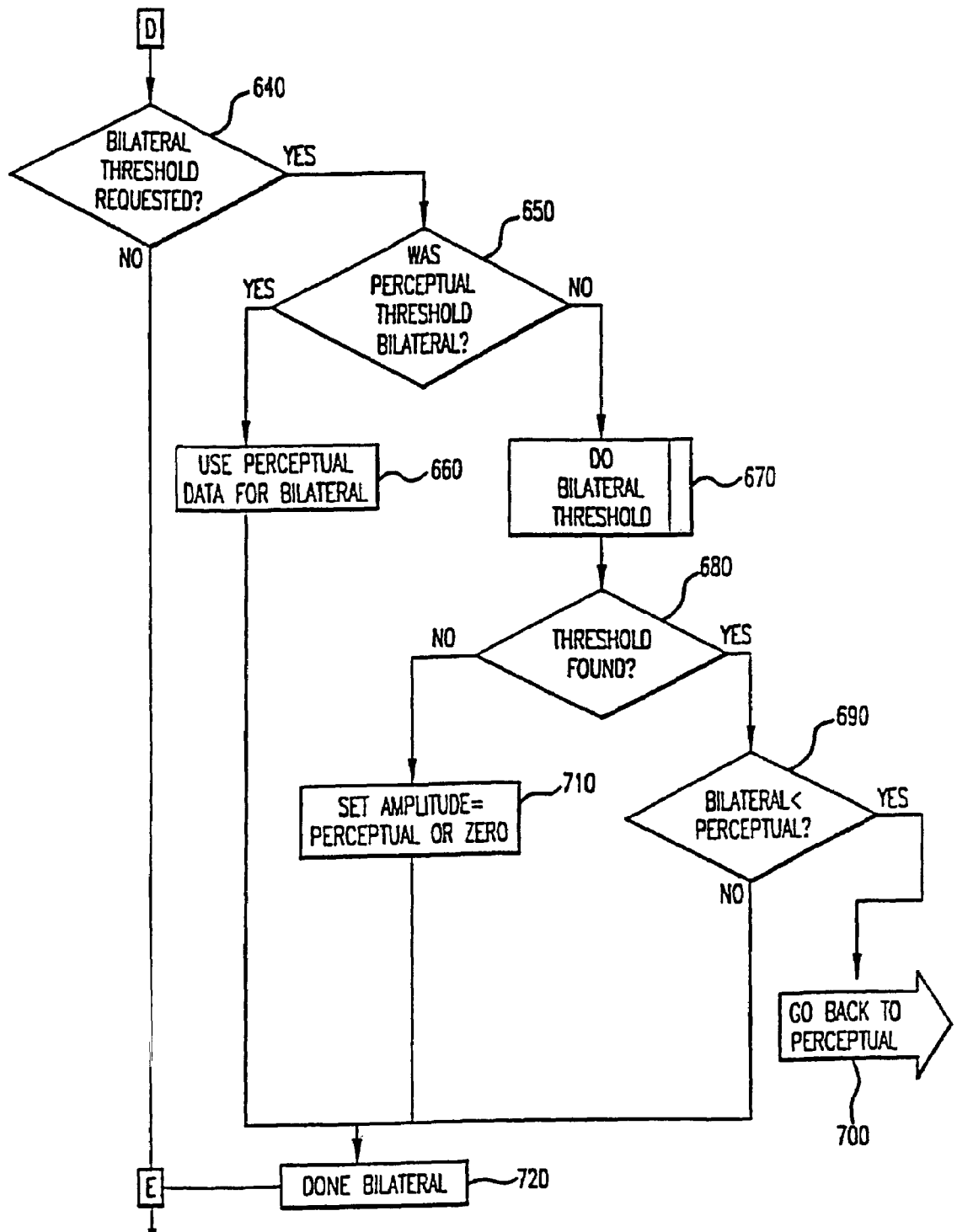
Figure 13C:
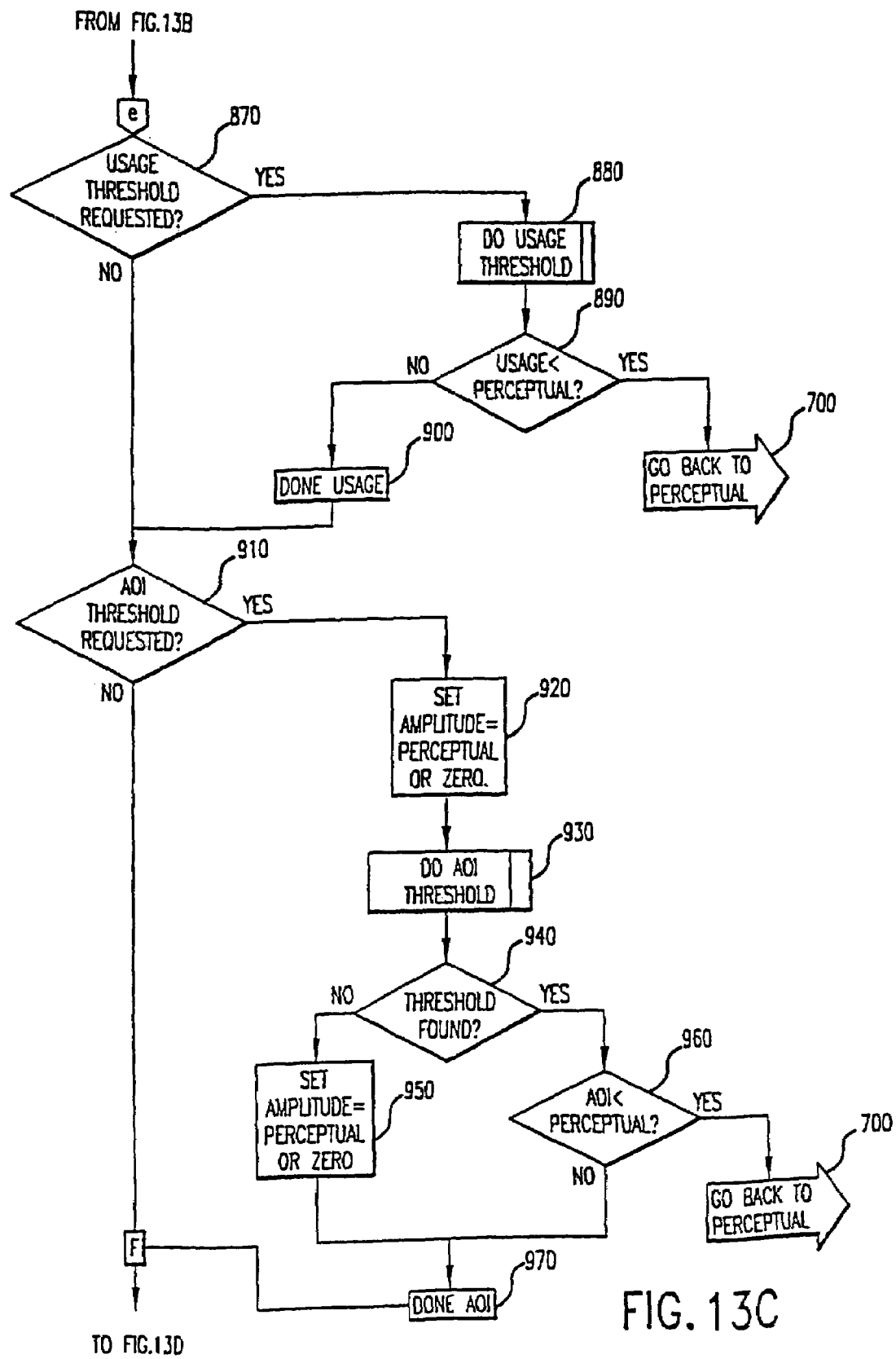
Figure 13D:
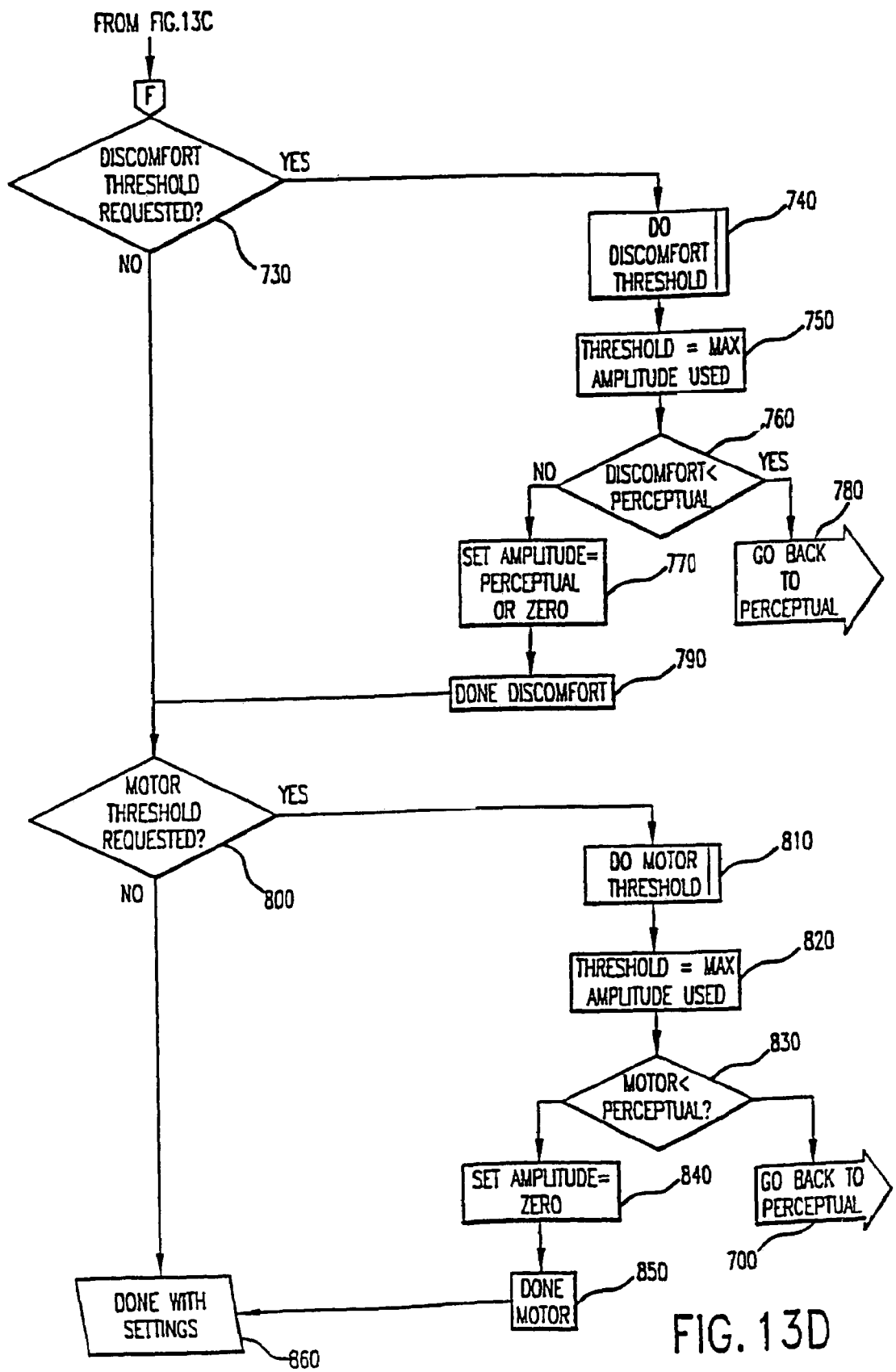
Figure 14A:
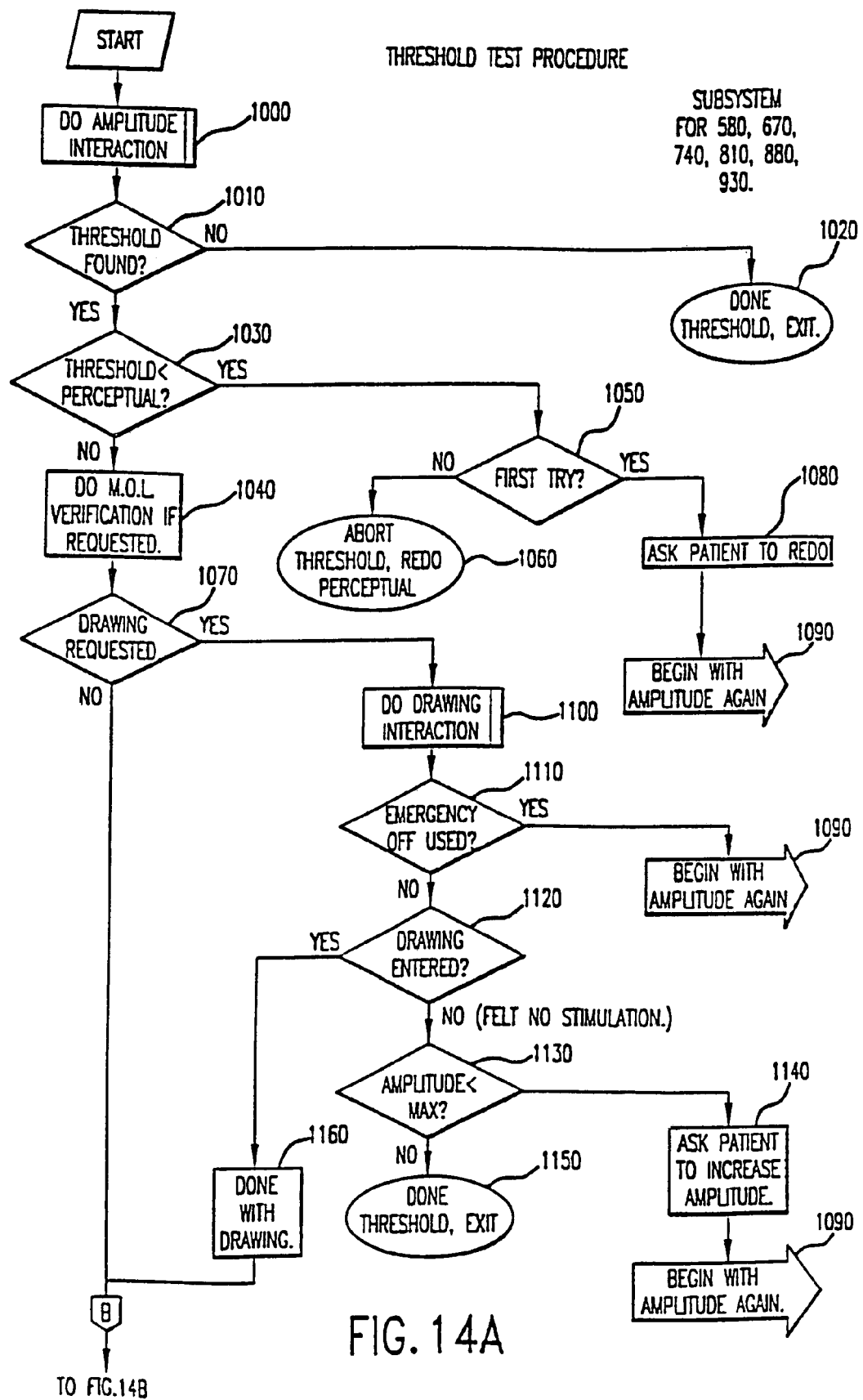
FIGS. 14A-14B represent a flow chart diagram of the threshold task procedure algorithm.
Figure 14B:
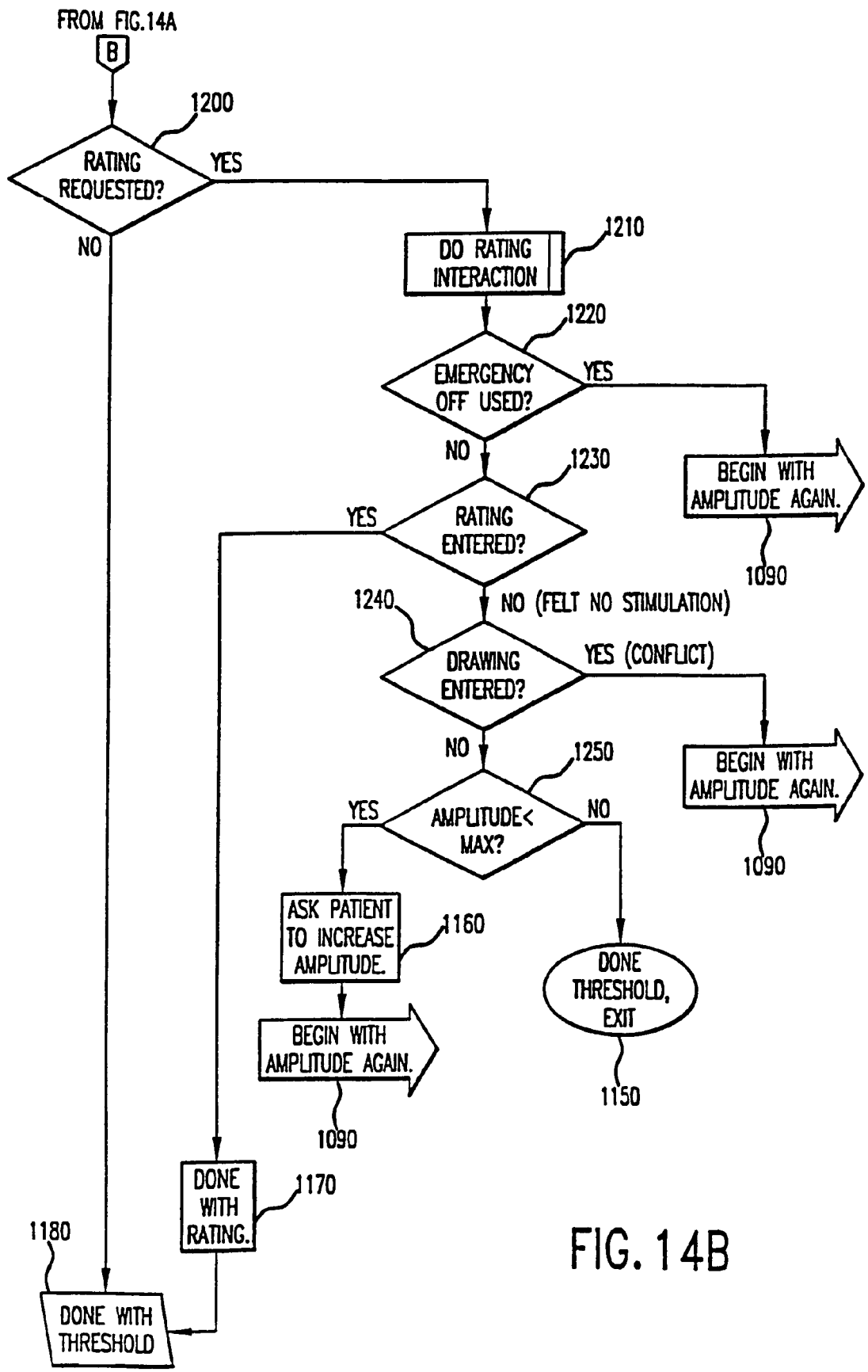

FIGS. 14A-14B illustrate a subsystem for flow blocks 580, 670, 740, 810, 880, and 930 of the FIGS. 13A-13D. As a part of the procedure, the system determines whether the perceptual threshold drawing was bilateral, and if this criteria has been met, the threshold is skipped in future operations. If the drawing was bilateral, as asked in the block 590, and a bilateral threshold is to be collected in this particular session, then the system confirms with the patient that they did in fact feel stimulation bilaterally, as is questioned in the flow block 600 which is stored for future use.

With reference to flow block 610, the system asks the question whether the patient needed to use maximum amplitude to get a perceptual threshold which is directed to whether the patient first felt the perceptual threshold at the absolute maximum setting of amplitude or did not feel it at all. In either case, there is no reason for further testing thresholds because they would increase from the perceptual threshold. In this case, the system skips the remainder of the threshold testing, as shown in block 630 with the remainder of this routine being skipped.

If the answer to the block 610 question is "no" the system goes to flow block 620, i.e., complete perceptual, and stores this data. The system program moves on to the bilateral threshold block 640 in a similar manner to entry into block 570. In flow block 640, the system tests whether the physician has requested a bilateral threshold to be determined. If the answer is "yes", the system moves on to the block 650 where it is determined whether the perceptual threshold was bilateral. If the answer is "yes", this data is used as the bilateral threshold in block 660. If the perceptual is not bilateral (answer "no"), or the perceptual stimulation data has not been collected, the system initiates and completes a bilateral threshold test in flow block 670.

Once this has been completed, the procedure enters the block 680 where the question of whether the threshold was found is asked. If the threshold was determined, that is to say, if it was possible for the patient to increase amplitude without discomfort to the point where they felt stimulation on both sides of the body, the procedure then proceeds to the block 690. In block 690, the question is asked "was the bilateral threshold less than perceptual?" This section of the program is a consistency check to ensure that the patient is following directions on the screen and answering consistently.

If in fact bilateral is determined to be less than perceptual threshold, this is considered to be erroneous data and the logic flow proceeds to block 570 for a retest associated with perceptual.

If the threshold for bilateral is greater than perceptual in block 690, the program passes through to block 720. At block 720, the bilateral threshold testing is completed. Returning to block 680, if the threshold was not determined, that is, the patient was unable to increase the amplitude to the point where they had stimulation on both sides of the body, the program passes to the flow block 710. In this case, the amplitude is reset to either the perceptual level, or to zero to indicate that the perceptual was not actually collected during this session. This is done so that the starting point in any further threshold in this logic chain is logically consistent. In this manner, the program starts below whatever threshold is to be achieved. When this is completed, the program passes to block 720 and "finish" bilateral threshold.

Moving down to the block 870 in FIG. 13C, the "usage threshold request", if this particular threshold has been requested by the physician, the program then is directed to flow block 880. Subsequent to completion of the usage threshold collection entry is made into block 890. The question is asked whether the usage threshold is less than the perceptual? This block is also an "absurdity check" similar to the previous block described in the bilateral case. If the usage was in fact less than perceptual, the program proceeds back and checks perceptual again in block 570. If usage is not-less than perceptual the program goes to flow block 900. From block 900, the logic proceeds to interest threshold in block 910.

If the threshold has been requested by the physician, the logic moves to flow block 920 for insuring that the starting amplitude is either perceptual or zero which would be the case where the perceptual has not been collected. The program then proceeds to and enters flow block 930 where the threshold data is accumulated.

From flow block 930, the program logic enters flow block 940 where it is determined whether the threshold has been found. If the threshold has not been found as requested in flow block 940, the amplitude in block 950 is reset back to perceptual or zero in the case where the perceptual has not been collected. Once this is completed, the logic passes to flow block 970 which completes the AOI procedure.

If the threshold has been found in flow block 940, the system then proceeds to decision flow block 960 which checks whether the area of interest (AOI) is less than the perceptual. If the answer is "no", the program then moves to block 970, however, if the answer is "yes", the logic moves to block 700 and then from this point returns to flow block 570 for a repeat of the test for the perceptual.

Once completed, the area of interest (AOI) threshold procedure has been completed and the program logic enters flow block 730 which is the discomfort threshold decision block. If the discomfort threshold has been requested, the next procedure is entry into flow block 740 which then leads to flow block 750 where the threshold is set to the maximum amplitude used. The patient is asked to reduce the setting back to a comfortable level after achieving the discomfort level. From block 750, the logic passes to decision block 760 where a decision is made by the patient as to whether discomfort is less than perceptual.

In this case, rather than storing the lower setting exiting out of the threshold test procedure, the maximum amplitude used during that setting is stored as the discomfort threshold.

In flow block 760, the question is asked of whether the discomfort threshold is less than the perceptual threshold and if this is answered "yes", the program proceeds to the beginning of the overall process in flow block 570. If the discomfort is less than the perceptual, the amplitude is then set either to zero or to the perceptual in block 770 which then completes the discomfort threshold level settings and data and the program moves to flow block 790.

Subsequent to the discomfort threshold procedure, decision block 800 is entered and requests whether the motor threshold has been requested. This block is very similar to the discomfort threshold block 730, however, it differs psycho-physically in that in this block it is determined at which point a muscle begins to spasm as opposed to a simple discomfort feeling by the patient. The point at which the muscles begin to spasm may be either higher or lower than the discomfort level and this dictates that the amplitude is set back to a lower value as requested in flow block 770.

If a motor threshold has been requested in flow block 800, the program then goes through block 810 for collection of the data. Leaving flow block 810, the logic moves to flow block 820 where the threshold is equal to the maximum amplitude used and assumed not to be comfortable to the patient. The patient is then requested to reduce the level to a more comfortable setting with the threshold as the maximum level being recorded.

The next step in the process is to proceed to decision flow block 830 where it is checked whether the motor threshold was less than or greater than the perceptual threshold. If the motor threshold is greater than the perceptual threshold there is an inconsistency in the data and we enter block 700 for passage to flow block 570.

If the motor threshold is less than the perceptual threshold, the flow logic moves to flow block 840 where the amplitude is set to zero and the motor threshold procedure has been completed with the logic flow passing to flow block 850.

Referring now to FIGS. 14A-14B, such represent essentially a subset of the flow blocks in FIGS. 13A-13D and namely expand on the blocks 580, 670, 740, 810, 880, and 930 directing itself to the overall threshold test procedure concept. The threshold test procedure is used to collect from the patient certain key pieces of information for some particular type of setting. The thresholds have been previously addressed in this Specification.

One example is the perceptual threshold setting and as is the case of any of the thresholds, the thresholds are all amplitude levels which correspond to psycho-physical conditions. Initially, the threshold is determined by stating appropriate criteria and having the patient adjust the amplitude to meet those criteria.

In FIGS. 14A-14B, the overall concept is to collect a "drawing" of the stimulation areas and collect subjective ratings as to the amount of pain relief or coverage of the pain areas which are achieved with a particular stimulation setting at a particular amplitude threshold. Thus, FIGS. 14A-14B are a procedure of interview with the patient to determine specific parameters.

The threshold procedure assumes that the patient transmitter has been set with a particular configuration of settings of interest to be explored and that the clinician has selected a particular threshold which is perceptual, usage, bilateral, area of interest, discomfort, or motor threshold dependent upon which is to be determined.

Initially, flow block 1000 is entered which is an amplitude interaction screen seen in FIGS. 8A-8B in which the patient is presented a brief set of criteria and requested to raise the amplitude of their stimulation to meet this criteria.

If the patient is able to meet the criteria, the logic flow moves to block 1010 and this is a decision block which requests whether the threshold has been found.

If the particular threshold requested was not able to be met, the program is directed to block 1020 and exits this procedure.

If the criteria has been met in decision block 1010, the flow moves to flow block 1030 which is a decision flow block to determine whether the threshold is less than the perceptual. Where the threshold is less than the perceptual, then the process moves to decision flow block 1050. As part of the overall program, the patient is generally given two tries and if the patient cannot correct the problem on the second try, the flow moves to block 1060 where the threshold procedure is aborted and passes to a re-input of the perceptual.

On the patient's first try in block 1050, the logic process moves to flow block 1080 where the patient is asked to reduce the threshold and then into block 1090 to begin with the amplitude once again which then passes back to flow block 1000.

If in fact after the patient has tried a second time to correct the signal in block 1050, everything is aborted in flow block 1060 and the program moves back to the flow blocks of FIGS. 13A-13D to handle the condition in the overall logic loop.

Assuming that in block 1030 the threshold is greater than the perceptual which results in a "no" answer for the decision block 1030, the program is then working with the perceptual threshold and the logic moves to flow block 1040 where an option is provided for completing a method of limit (M.O.L.) verification routine where the patient is asked in sequential fashion to precisely determine the actual threshold.

From flow block 1040, the logic moves to flow block 1070 after the amplitude has been set and a drawing is then pulled up. Flow block 1070 is a decision flow block asking whether the drawing has been requested. If the drawing has been requested, the process moves to flow block 1100 and a drawing is collected.

Drawings for this portion of the procedure are shown in FIGS. 7A-7B and the patient is essentially asked to draw or otherwise indicate the regions on the body where stimulation is felt. This step is completed by moving the stylus 31 over a body map.

Once the patient has completed the drawing, a test is initiated in block 1110 to determine whether at any point in this interaction the patient has used the emergency "off" feature. The patient has several options for turning off stimulation rapidly should the patient become uncomfortable during the procedure.

The "off" is a physical hardware switch and an onscreen button as described with reference to FIGS. 7A-11.

If the emergency "off" feature has been used, the threshold is not a reliable piece of data. Generally, once the emergency "off" feature has been used, the program proceeds back to amplitude and begins once again. After having set the amplitude to zero, the patient then brings up the level to meet the criteria in block 1090.

Assuming that the stimulation has not been turned "off", the logic proceeds from block 1110 to the decision block 1120 which asks whether the drawing has been entered. If the drawing has been entered by the patient, block 1160 is entered for completion of the drawing.

If the drawing has not been entered as answered from decision block 1120, decision block 1130 is entered to determine whether the amplitude is less than the maximum. If the amplitude is greater than the maximum, the process moves to block 1150 where a conclusion is made that the patient feels no stimulation and would feel none at maximum amplitude which completes the testing of the threshold and the system exits back to the flow blocks shown in FIGS. 13A-13D.

However, if the patient has not used the maximum amplitude threshold, the logic proceeds to flow block 1140 where the patient is asked to increase the amplitude and then the logic flows to block 1090 and ultimately back to block 1000 as previously noted to determine the amplitude once again.

If a proper drawing has been entered in flow block 1120, there is a completion of the collecting of the drawing and the logic flows to FIG. 14B to the rating screen shown in flow block 1200. The physician has the option in decision flow block 1200 of collecting or not collecting a reading. Additionally, the physician has the option of collecting ratings from predetermined thresholds. If this particular threshold has a requested rating associated with it, then the logic flows from flow block 1200 to flow block 1210.

In flow block 1210, there is a rating interaction performed. In this block, the patient is asked to rate their subjective overlap of the pain areas with the stimulations. The patient is asked to mark a linear 100 MM scale (amplitude adjustment bar 57 of FIGS. 8A and 8B) which indicates what the coverage is subjected to.

After collection of the data, the process information proceeds to flow block 1220 to again test whether the patient used the emergency "off" feature. If the emergency "off" feature has been used, all threshold data is not used and the program proceeds back to the amplitude interaction and a restart.

If in fact, the patient has successfully completed a rating and has not used any of the "off" features, the flow moves to flow block 1230 where a decision is made whether the rating has been entered. If the rating has not been entered, there is an assumption made that no stimulation has been felt by the patient. However, since a rating generally follows the drawing, there must be a check as to possible conflicts.

If the drawing was entered as determined by flow block 1240 and the rating had not been entered, there is a conflict of end responses and the program proceeds to the data in block 1090 for return to flow block 1000 to begin the threshold testing procedure once again.

If no drawing was entered as determined in the decision block 1240 or no drawing was requested, at the option of the physician, then there is an assumption made that the patient has indicated by not entering a rating and that no stimulation was felt.

Under these conditions, the logic passes to a decision flow block 1250 where a test is made of whether the maximum amplitude was used. If the maximum amplitude was used, the information flow passes to block 1150.

If the amplitude was less than the maximum and no stimulation was found then in block 1160 the patient is asked to increase the amplitude and after increasing the amplitude, you begin the amplitude process again in block 1090.

Returning to flow block 1230 which is a decision flow block determining whether the rating was entered, if the answer is "yes", the logic flow of the program brings the program to flow block 1170 which is a completion with the rating and interaction test, and this then proceeds to flow block 1180 which is a completion of the threshold procedure.

As previously described, the patient interactive system of the subject invention provides for a plurality of advantages generally not seen in combination in prior stations which includes:

(a) a fully automated compact, self-contained system for easy transport and comfortable patient use;
(b) a pen-on-screen entry system for simplified patient understanding;
(c) transparent programming of multiple implant types provided by one singular unit;
(d) a robust, patient interactive protocol minimizing professional time and costs;
(e) a rapid computer testing system which allows practical screening of numerous stimulation settings;
(f) computer analysis and digitized maps of pain and paresthesia providing precise detailed information to a physician and pertinent documentation of the outcome;
(g) enhanced and optimized patient interaction and analysis software, allowing consistency check and adaptation to a particular patient;
(h) remote computer server connection capabilities allowing comparison between centers and tracking of implants usage.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described. Certain features may be used independently of other features, and in certain cases, particular locations of elements may be reversed or interposed, all without departing from the spirit or scope of the invention as defined in the appended claims.

What is claimed is:

1. A method comprising:
controlling an implantable neurostimulator to deliver neurostimulation to a patient according to a plurality of stimulation settings during a programming session;
displaying a list of the stimulation settings;
collecting information for each of the stimulation settings, wherein the collected information comprises:
rating information comprising:
a numeric rating for the stimulation setting; and
a degree of overlap between a paresthesia map for the stimulation setting and a pain map; and
a threshold amplitude value for the stimulation setting;
receiving input from a user choosing at least one criteria selected from the collected information; and
ordering the list according to the at least one user-chosen criteria selected from the collected information.

2. The method of claim 1, wherein each of the stimulation settings includes a pulse width, a pulse frequency, an identification of activated electrodes, and an identification of polarities of activated electrodes.

3. The method of claim 1, wherein the user-chosen criteria comprises the numeric ratings, and ordering the list comprises ordering the list according to the numeric ratings.

4. The method of claim 1, wherein the numeric ratings indicate a degree of pain-relief.

5. The method of claim 1, wherein the user-chosen criteria comprises tho degrees of overlap and ordering the list comprises ordering the list according to the degrees of overlap.

6. The method of claim 1, wherein collecting rating information comprises collecting rating information from the patient.

7. The method of claim 1, further comprising selecting at least one stimulation setting from the plurality for retesting based on the user-chosen criteria.

8. The method of claim 1, further comprising automatically programming the neurostimulator with at least one of the stimulation settings based on the user-chosen criteria.

9. The method of claim 1, wherein controlling the implantable neurostimulator to deliver neurostimulation to the patient according to the plurality of stimulation settings during the programming session comprises:
storing a plurality of predetermined programming codes;
identifying a type of an implantable neurostimulator;
selecting one of the plurality of programming codes based on the identified type; and
transmitting the selected programming code to the implantable neurostimulator to enable programming of the implantable neurostimulator.

10. The method of claim 9, wherein transmitting the selected programming code comprises modulating a carrier signal.

11. The method of claim 10, further comprising retrieving parameters for modulation of the carrier signal from a memory based on the identified type of the implantable neurostimulator.

12. The method of claim 1, further comprising receiving input from the patient indicative of a stimulation amplitude of the neurostimulation, wherein controlling the implantable neurostimulator to deliver neurostimulation to the patient comprises controlling the implantable neurostimulator to deliver neurostimulation to the patient at the stimulation amplitude indicated by the user.

13. The method of claim 1, further comprising determining the threshold amplitude value for each of the stimulation settings.

14. The method of claim 1, wherein collecting the threshold amplitude value for each of the stimulation settings comprises determining at least one of a perceptual threshold, a usage threshold, an area of interest threshold, a motor threshold or a discomfort threshold for each of the stimulation settings.

15. The method of claim 1, further comprising, for each stimulation setting, determining whether the rating information falls within boundaries based on the threshold amplitude value.

16. The method of claim 1, further comprising:
providing the collected information to at least one of a server or a database.

17. A device for programming an implantable neurostimulator comprising a display, wherein the device is adapted to control the implantable neurostimulator to deliver neurostimulation to a patient according to a plurality of stimulation settings during a programming session, display a list of the stimulation settings via the display, collect information for each of the stimulation settings, receive input from a user choosing at least one criteria selected from the collected information, and order the list according to the at least one user-chosen criteria, wherein the collected information comprises:
rating information comprising:
a numeric rating for each of the stimulation settings; and
a degree of overlap between a paresthesia map for the stimulation setting and a pain map; and
a threshold amplitude value for the stimulation setting.

18. The device of claim 17, wherein each of the stimulation settings includes a pulse width, a pulse frequency, an identification of activated electrodes, and an identification of polarities of activated electrodes.

19. The device of claim 17, wherein the user-chosen criteria comprises the numeric ratings, and the device orders the list according to the numeric ratings.

20. The device of claim 17, wherein the numeric rating indicates a degree of pain-relief.

21. The device of claim 17, wherein the display is a touch screen display, and the device collects the numeric rating via the display.

22. The device of claim 17, wherein the display is a touch screen display, and
wherein the user-chosen criteria comprises the degrees of overlap, and the device orders the list according to the degrees of overlap.

23. The device of claim 17, wherein the device selects at least one stimulation setting from the plurality for retesting based on the user-chosen criteria.

24. The device of claim 17, wherein the device is adapted to automatically program the neurostimulator with at least one of the stimulation settings based on the user-chosen criteria.

25. The device of claim 17, wherein the device comprises a portable computer.

26. The device of claim 17, wherein the device comprises a tablet computer.

27. The device of claim 17, wherein the device further comprises:
an antenna that identifies a type of the implantable neurostimulator; and
a transmitter interface that includes a memory to store a plurality of predetermined programming codes, wherein the transmitter interface is adapted to receive an indication of the identified type of the implantable neurostimulator, select one of the plurality of programming codes based on the identified type, and transmit the selected programming code to the implantable neurostimulator via the antenna to enable programming of the implantable neurostimulator to deliver neurostimulation to the patient.

28. The device of claim 27, wherein the transmitter interface transmits the selected programming code by modulating a carrier wave.

29. The device of claim 28, wherein the memory stores parameters for modulation of the carrier wave associated with each of the programming codes, and the transmitter interface further includes control interface circuitry that retrieves parameters from the memory based on the identified type of the implantable neurostimulator and controls modulation of the carrier wave according to the retrieved parameters.

30. The device of claim 28, wherein the transmitter interface includes at least one of a direct digital synthesizer, programmable gain/amplitude circuitry or a transistor circuit to modulate the carrier wave.

31. The device of claim 17, wherein the device presents an amplitude adjustment screen and receives input from the user adjusting a stimulation amplitude of the neurostimulation via the amplitude adjustment screen.

32. The device of claim 17, wherein the device determines the threshold amplitude value for each of the stimulation settings.

33. The device of claim 17, wherein the device provides the collected information to at least one of a server or a database.

34. A system for programming an implantable neurostimulator comprising:
means for controlling the implantable neurostimulator to deliver neurostimulation to a patient according to a plurality of stimulation settings during a programming session;
means for displaying a list of the stimulation settings;
means for collecting information for each of the stimulation settings, wherein the collected information comprises:
rating information comprising:
a numeric rating for the stimulation setting; and
a degree of overlap between a paresthesia map for the stimulation setting and a pain map;
a threshold amplitude value for the stimulation setting; and means for receiving input from a user choosing at least one criteria from the collected information; and means for ordering the list according to a least one user-chosen criteria selected from the collected information.

35. The system of claim 34, wherein the user-chosen criteria comprises the rating information, and the means for ordering the list comprises means for ordering the list according to the numeric ratings.

36. The system of claim 34, wherein the user-chosen criteria comprises the degrees of overlap, and the means for ordering the list comprises means for ordering the list according to the degrees of overlap.

37. The system of claim 34, further comprising means for selecting at least one stimulation setting from the plurality for retesting based on the user-chosen criteria.

38. The system of claim 34, further comprising means for automatically programming the neurostimulator with at least one of the stimulation settings based on the user-chosen criteria.

39. The system of claim 34, further comprising means for providing the collected information to at least one of a server or a database.

* * * * *

UNITED STATES PATENT AND TRADEMARK OFFICE
CERTIFICATE OF CORRECTION

PATENT NO. : 7,386,348 B2  Page 1 of 1
APPLICATION NO. : 10/669392
DATED : June 10, 2008
INVENTOR(S) : Richard B. North et al.

It is certified that error appears in the above-identified patent and that said Letters Patent is hereby corrected as shown below:

Column 39, line 3, "to a least" should read -- to at least --.

Signed and Sealed this

Seventeenth Day of February, 2009

JOHN DOLL
*Acting Director of the United States Patent and Trademark Office*